(12) United States Patent
Florman et al.

(10) Patent No.: US 6,991,909 B2
(45) Date of Patent: Jan. 31, 2006

(54) ENKURIN AND USES THEREOF

(75) Inventors: Harvey Florman, Northborough, MA (US); Melissa Jungnickel, Worcester, MA (US); Keith Sutton, Worcester, MA (US)

(73) Assignee: University of Massachusetts, Boston, MA (US)

( * ) Notice: Subject to any disclaimer, the term of this patent is extended or adjusted under 35 U.S.C. 154(b) by 145 days.

(21) Appl. No.: 10/375,693

(22) Filed: Feb. 25, 2003

(65) Prior Publication Data

US 2004/0023873 A1 Feb. 5, 2004

Related U.S. Application Data

(60) Provisional application No. 60/359,870, filed on Feb. 25, 2002.

(51) Int. Cl.
*G01N 33/53* (2006.01)
*G01N 33/537* (2006.01)

(52) U.S. Cl. ................ 435/7.1; 435/7.95; 435/176; 436/514; 436/536; 436/15

(58) Field of Classification Search ............... 435/7.1, 435/7.95, 176; 436/514, 536, 15
See application file for complete search history.

(56) References Cited

PUBLICATIONS

Brann et al., "Type–specific inositol 1,4,5–trisphosphate receptor localization in the vomeronasal organ and its interaction with a transient receptor potential channel, TRPC2," *J. Neurochem.* 83(6):1452–60 (2002).
Ives et al., "Characterization of chromosomal DNA amplifications with associated tetracycline resistance in *Bacillus subtilis,*" *J. Bacteriol.* 172(9):4936–44 (1990).
Yidirim et al., "The mouse C–Type transient receptor potential 2 (TRPC2) channel: alternative splicing and calmodulin binding to its N terminus," *Proc. Natl. Acad. Sci U S A.* 100(5):2220–2225 (2003).
Arnoult et al., "ZP3–dependent Activation of Sperm Cation Channels Regulates Acrosomal Secretion During Mammalian Fertilization," *J. Cell Biol.* 134:637–645 (1996).
Arnoult et al., "Activation of mouse sperm T–type $Ca^{2+}$ channels by adhesion to the egg zona pellucida," *Proc. Nat. Acad. Sci. USA* 93:13004–13009 (1996).
Arnoult et al., "Control of the low voltage–activated calcium channel of mouse sperm by egg ZP3 and by membrane hyperpolarization during capacitation," *Proc. Natl. Acad. Sci. USA* 96:6757–6762 (1999).
Clapham et al., "The TRP Ion Channel Family," *Nature Rev. Neurosci.* 2:387–396 (2001).
Clark et al., "Caltrin, the Calcium Transport Regulatory Peptide of Spermatozoa, Modulates Acrosomal Exocytosis in Response to the Egg's Zona Pellucida," *J. Biol. Chem.* 268:5309–5316 (1993).

Florman et al., "An Adhesion–Associated Agonist from the Zona Pellucida Activites G Protein–Promoted Elevations of Internal $Ca^{2+}$ and Ph that Mediate Mammalian Sperm Acrosomal Exocytosis," *Dev. Biol.* 135:133–146 (1989).
Florman et al., "Activation of Voltage–Dependent Calcium Channels of Mammalian Sperm Is Required for Zona Pellucida–Induced Acrosomal Exocytosis," *Dev. Biol.* 152:304–314 (1992).
Florman et al., "Sequential Focal and Global Elevations of Sperm Intracellular $Ca^{2+}$ Are Initiated by the Zona Pellucida during Acrosomal Exocytosis," *Dev. Biol.* 165:152–164 (1994).
Gallouzi et al., "Delineation of mRNA Export Pathways by the Use of Cell–Permeable Peptides," *Science* 294:1895–1901 (2001).
Genebank Accession No. AF111107.
Genebank Accession No. AF111108.
Genebank Accession No. NM_145010.
Hofmann et al., "Cloning, expression and subcellular localization of two novel splice variant of mouse transient receptor potential channel 2," *Biochem. J.* 351:115–122 (2000).
Jungnickel et al., "Trp2 regulates entry of $Ca^{2+}$ into mouse sperm triggered by egg ZP3," *Nature Cell Biology* 3:449–502 (2001).
Kirkman–Brown et al., "Biphasic Elevation of $[Ca^{2+}]_i$ in Individual Human Spermatozoa Exposed to Progesterone," *Dev. Biol.,* 222:326–335 (2000).
Liman et al., "TRP2: A candidate transduction channel for mammalian pheromone sensory signaling," *Poc. Natl. Acad Sci. USA* 96:5791–5796 (1999).
O'Toole et al., "$Ca^{2+}$ Entry through Store–operated Channels in Mouse Sperm is Initiated by Egg ZP3 and Drive the Acrosome Reaction," *Molecular Biol. Of Cell* 11:1571–1584 (2000).
Son et al., "Acrosome reaction of human spermatozoa is mainly mediated by α1H T–type calcium channels," *Mol. Human Reprod.* 6:893–897 (2000).
Vannier et al., "Mouse trp2, the homologue of the human trpc2 pseudogene, encodes mTrp2, a store depletion–activated capacitative $Ca^{2+}$ entry channel," *Proc. Natl. Acad. Sci. USA* 96:2060–2064 (1999).
Wes et al., "TRPCI, a human homolog of a *Drosophila* store–operated channel," *Proc. Natl. Acad. Sci. USA* 92:9652–9656 (1995).
Wissenbach et al., "Structure and mRNA expression of a bovine trp homologue related to mammalian trp2 transcripts," *FEBS Lett.* 429:61–66 (1998).

*Primary Examiner*—Long V. Le
*Assistant Examiner*—Jacob Cheu
(74) *Attorney, Agent, or Firm*—Fish & Richardson P.C.

(57) ABSTRACT

A novel protein, enkurin, that is preferentially expressed in sperm has been discovered. Enkurin binds to TRPCs including TRPC2-S, a protein encoded by TRPC2 that is not predicted to be a calcium channel subunit. The invention includes methods of identifying compounds that affect enkurin expression or activity, and are useful, e.g., for contraception and treatment of infertility.

16 Claims, 23 Drawing Sheets

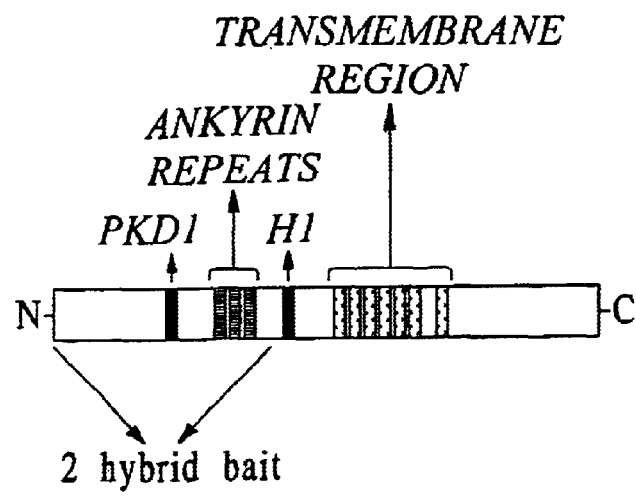
FIG. 1
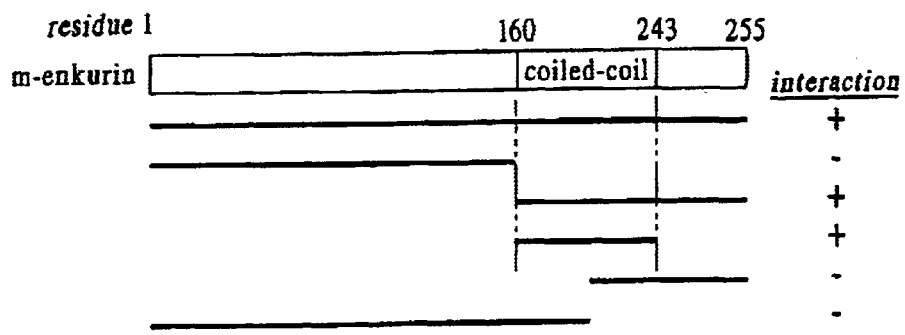
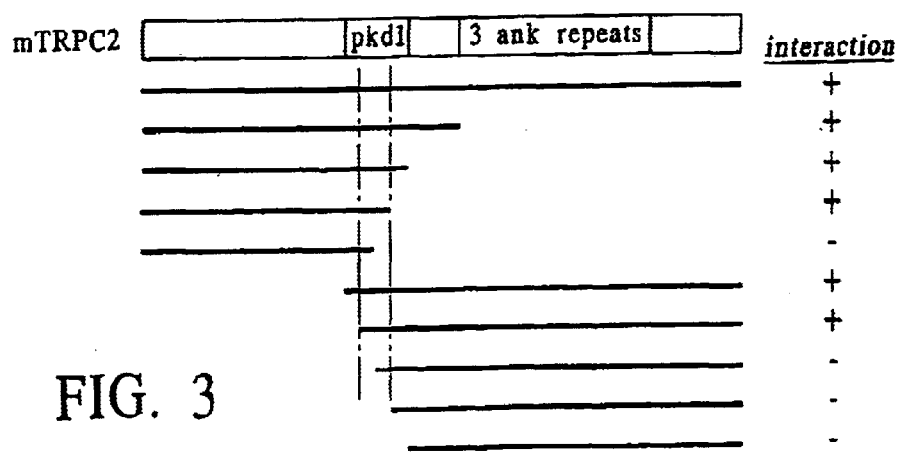
FIG. 3

```
   1
Mus    MDSPCTSESI YNLIPSDLKE PPQHPRYTSL FRATIKNDMK KFKTAMKTMG      50
Homo   --PT-S-C-- ---------- ---P----I-I -K--V-D--Q -A--------

51
Mus    PAKVEIPSPK DFLKKHSKEK TLPPKKKFNR CSPKKPAVPL RTDHPVMGIQ     100
Homo   -----V---- ---------- ------N-D- ------NV-- ------K---

101
Mus    SGKNFINTNA ADVIMGVAKK PKPIYVDKRT GDKHDLETSG LFPKYINKKD     150
Homo   ---------- ----I----- ---------- ---------- ----P---V-

151
Mus    YGITPEYICK RNEDVKKAQE EYDNYIQENL KKAAMKRLSD EEREAVLQGL     200
Homo   --V------- -------EI- ---D--R--- ---------- ----------

201
Mus    KKNWEEVHKE FQSLSVFIDS VPKKIRKQKL EKEMKQLEHD ISVIEKHKII     250
Homo   ---------- ---------- -----I---- ----R----E --------GI 251
Mus    YIANK (SEQ ID NO:1)
Homo   ----A (SEQ ID NO:2)
```

FIG. 2

```
            Exon 3b                          Exon 4
mus   1   MGTKTHPVVPWSTKEISELKGMLKQLQPGPLGRAARMVLS
homo      ---YSLF-CRD-------RNI-T----T---S-H---

Exon 4                           Exon 5
mus  41   AARKAPPASVVSPNNSHGEPGPSRAESAEPRAEEPNRKTA
homo      --HRV--V-A--K-N-A----     (SEQ ID NO: 15)

Exon 5                           Exon 6
mus  81   VGRRKRRKVQEPRRSLSNSSSQPNRRTGRTRQRQHRPQTK
homo                                      KKK-----AQ Exon 6                           Exon 7
mus 121   SDDGGVQATGQCPICAGFFSIETLPQHAATCGESPPPQPA
homo      -SGG    -DS--------G-R--I------TS--H---

Exon 7                          Intron 7
mus 161   SPASLSSS ESVLWVSSPESSPPPSWVQCPICELQFSARE
homo      --S-S---SQ---------------------V---P---Q-R---

Intron 7
mus 201   IEEHASVCGEVLPA      (SEQ ID NO: 3)
homo      V-----I--D.         (SEQ ID NO: 4)
```

FIG. 6

TRPC2A mus    LPQHAATCG ESPPPQPASPASLSSS  (SEQ ID NO: 5)
TRPC2-S mus   ----------G------------------  (SEQ ID NO: 6)
TRPC2-S homo  ----------TS--H----S-S---  (SEQ ID NO: 7)

(SEQ ID NO: 12)

```
   1 gaccacgtgg tcaacaacgc taaacagact cggagcagaa ttatttctt cctgaaaaag
  61 ggactgttac gaaagggtca aagggaaatt acacgaaaga gaaatttag ttctttgata
 121 agaaagtaag aaaagaaaaa ggcggtgaga gaaggagttg agacagtggg aaagtgagcc
 181 aaaaagctga gtacttgtta aggaattcct tggtggccat ggactcaccc tgcacttccg
 241 agagtattta taacctcata cccagtgact tgaaggagcc gccccagcat cctaggtata
 301 catcactgtt tagagcaact ataaaaaatg acatgaagaa atttaaaacg gcaatgaaaa
 361 ccatgggacc tgcaaaagta gagataccct cccccaagga ttttctaaag aagcattcca
 421 aggaaaaaac actaccacca aaaaaaaagt ttaataggtg ctctcccaag aagcctgcag
 481 tgcccttgag aaccgatcat ccagttatgg gaatacagag tggaaaaaac ttcataaaca
 541 caaatgcagc tgacgtcatc atgggcgtgg ccaaaaagcc caagccgatt tatgttgaca
 601 aaagaactgg agataagcat gacctttgaaa cttcagggct attcccccaag tacatcaaca
 661 aaaaggatta tggcatcacg cctgagtaca tatgcaagcg aaatgaggat gtgaagaaag
 721 cacaagaaga gtatgacaat tacatccagg agaacctcaa gaaagcggcc atgaagagac
 781 tctctgacga agaaagggag gcagttctgc agggactgaa gaagaactgg gaagaggtgc
 841 acaaagagtt ccaatccctc tcggtcttca ttgattctgt accaaagaag attcgcaagc
 901 agaagctgga aaaagagatg aagcagctgg aacacgacat cagtgtcatt gagaagcaca
 961 agatcatcta catcgctaac aagtgagcca actgttgcag gacagaaaaa agccacatgg
1021 ccatcacact aaacccactc ttctcaaaga ggactatgaa gagaataaag ttttcaccga
1081 aaatgtaggg gcagtgttga aagaatagtt gaattatttg cttgctctag agaaaattt
1141 ctcctccact gtcagagttc tacttataaa caaaccatta aagtcagaag ctgcaccttg
```

FIG. 9A

```
  1 gactgctaag aggggttaa aggggacga tgtgaaggag agaacctgtg gtcctcaga
 61 aggcgaagaa gaaagaaagg ggaagcagtg aagaaaggga cggagatact gggacaggga
121 gaaaaagtt gtggagagta gcttttaagg agtcatttgg tggccatgga tccaacgtgc
181 tcttctgagt gcatttataa cctcatacc agtgacttga aggagcctcc ccagcctcct
241 agtacatat ccatttttaa ggcaactgta aaagatgaca tgcaaaaagc taaaactgca
301 atgaaaacta tgggaccagc aaaagttgaa gtacctctc caaggatt cctaaagaaa
361 cattcaaagg agaaaactct accacccaaa aaaaactttg atcggaacgt gcccaaaaag
421 cctgctgtgc cattgaagac tgatcatcct gtcatgggaa tacagagtgg aaaaaatttt
481 ataatacaa atgcagctga tatcatcatg ggagtggcta aaaagcctaa accaatttat
541 gttgataaaa gaactggaga caagcatgat cttgagcctt caggactagt tccaaagtac
601 atcaataaaa aggattatgg tgtcacacct gaatacatat atccaggaaa cgaggaaata
661 aagaaagccc aagaagacta tgatcgttat atccaggaaa acttaagaa agcagctatg
721 aaaagctct ccgatgaaga aagggaggca gttttgcagg ggctgaaaaa gaactgggaa
781 gaggtgcata aagaattcca gtcccctctcg gtctttatag attctatacc aaagaagatc
841 cgcaagcaga ggctggaaga agaaatgaaa caactagaac acgacattgg cataattgaa
901 aagcacaaga ttattatat tgccaataac gcatga       (SEQ ID NO:20)     FIG. 9B
```

FIG. 12A

5'-
ATGGCTCCTGTGAAGATCAGCCATGTGGTGTCATTTTCCTCTCAGGATCCCAAATATCCTGTGAGAA
CTTGCTGAACCCAGACAGTCACAGGGACCCTGCTCAGCTGCCCTCAGGACAAGACTGGACAACTGA
AAGTGGAGTTTCAGCTGGAGAGGGCAGTGCCCATAAGCTATATTGATGTTGGAAACTGGCTGTGCT
TTCCTACAGATTGATGTGGGTCGTTCTTCCTGGCCCCTGGACAGACCTTTCGTCACCCTGCTCCCTgc
caccatg - 3' (SEQ ID NO:21)

FIG. 12B

MAPVKISHVV SFSSQDPKYP VENLLNPDSH RGPWLSCPQD KTGQLKVEFQ LERAVPISYI
DVGNCGCAFL QIDVGRSSWP LDRPFVTLLP ATM (SEQ ID NO:22)

FIG. 13A

5'-
ATGGCTCCTGTGAAGATCAGCCATGTGGTGTCATTTTCCTCTCAGGATCCCAAATAT
CCTGTGGAGAACTTGCTGAACCCAGACAGTCACAGGGGACCCTGGCTCAGCTGCCCT
CAGGACAAGAACTGGACAACTGAAAGTGGAGTTTCAGCTGGAGAGGGCAGTGCCCATA
AGCTATATTGATGTTGGTGATTTCCTGACTCCAGCCTCATCAGTCCTTTGGCCTGGCCTTC
CTTCGATTGACCTGCGTTCCCAACCTTTCACACTGTCTCTGGCTGACCCTGAGCCTTC
CTACGAGTGCGTTCCTCTCTGGCTGCTCCTGACCCTGTAGTAGATCCCTCAGCC
CCTGGGAGCTCTGGGCTTAACCAG - 3' (SEQ ID NO:23)

FIG. 13B

MAPVKISHVV SFSSQDPKYP VENLLNPDSH RGPWLSCPQD KTGQLKVEFQ
LERAVPISYI DVGDFLTPAS GESWDRLRLT CSQPFTRHQS FGLAFLRVRS
SLGSLADPVV DPSAPGSSGL NQ (SEQ ID NO:24)

FIG. 14A

5'-
ATGGCTCCTGTGAAGATCAGCCATGTGGTGTCATTTTCCTCTCAGGATCCCAAATATCCTGTGGAGAACTTGC
TGAACCCAGACAGTCACAGGGACCCCTGGCTCAGCTGCCCTCAGGACACAAGACTGGACAACTGAAAGTGAGTT
TCAGCTGGAGGGCAGTGCCCATAAGCTATATTGATGTTGGAAACTGTGGTGCTTTCCTACAGATTGAT
GTGGGTCGTTCTTCCTGCCCCTGACAGACCTTTCGTCTCCCTGCTCCCTGCCACCATGCTAATGTCCCGCA
CTGACTCCAAGTCGGGGAAGAACCGCTCAGGGTCCGGATGTTAAAGATGTGATTTCCTGACTCCAGCCTC
AGGAGAGTCCTGGATCGACTTCGATTGACCTGCTCCCAACCTTTCACAGTCATCAGTCCTTTGGCCTGGCC
TTCCTACGAGTGCGTTCCTCTCGGGCTCTCTGGAGTCTGATCCTAGCCCCTGACTAATCCTTCTATCCGGAG
GGCTTAACCAGAACTCTACAGATGTGCTGAGAGCACCAAGAGCTCAAGGTATGTTGAAGCAGTTGCAG
GACATTTTCCCGATCCCCCAGAGCAGCCCGCATGGTGCTTTCTGCTGCCCAGCCGTGGTAA
CCAGGGCCTCTGGGCGGGCACGGAGAACCAGGTCCCGTGCAGAGTGCAGAGCAGAGAAGAACCAAA
GCCCAAACAACAGCCAAGGACGTCAGGGAAGAGAGGAAAGTGCAGGAGATCGTTGTCCAACTCGAGT
CAGGAAGACGCGTGTGGGCAGAGGACAGGAGAAGACAAGACACCGACCTCAGACCGACTCTTCCCAGCATGCGTG
TCTCAGCCAAATAGGAGGACAGGAGTGTCCTATTTGTGCAGGTTTCTCCTGCCTTCTCCTCAGTATTGAGACTCTTCCCGGAGTCCGTGTTGG
AACTTGGCAGGCTGCTGAGAGCCCCACCAGCTTCTCCTGCCTTCTCCTGGGTCCAGTGCCCTATCTGTGAATTACAGTTCTCAGCAA
GTCTCCCCAGAGAAGAACATGCCAGAGCCGCCGCAGCGTGTGTGGGGAAGTTTGCCAGCCTGA -3' (SEQ ID NO:25)

FIG. 14B

MAPVKISHVVSFSSQDPKYPVENLLNPDSHRGPWLSCPQDKTGQLKVEFQLERAVPISYIDVGNCGCAFL
QIDVGRSSWPLDRPFVTLLPATMLMSRTDSKSGKNRSGVRMFKDGDFLTPASGESWDRLRLTCSQPFTRH
QSFGLAFLRVRSSLGSLADPVVDPSAPGSSGLNQNSTDVLESDPRPWLTNPSIRRTFFPDPQTSTKEISE
LKGMLKQLQPGPLGRAARMVLSAARKAPPASVVSPNNSHGEPGPSRAESAEPRAEPNRKTVGRRKRRKV
QEPRRSLSNSSQPNRRTGRTRQHRPQTKSDDGGVQAAGQCPICAGFFSIETLPQHAATCGESPPPQP
ASPASLSSSESVLWVSSPESSPPPSWVQCPICELQFSAREIEEHASVCGEVLPA (SEQ ID NO:26)

FIG. 15A

5'-
ATGGCTCCTGTGAAGATCAGCCATGTGGTGTCATTTTCCTCTCAGGATCCCAAATATCCTGTGGAGAAC
TTGCTGAACCCAGACAGTCACAGGGGACCCTGGCTCAGCTGCCCTCAGGACAAGACTGGACAACTGAAA
GTGGAGTTTCAGCTGGAGAGGGCAGTGCCCATAAGCTATATTGATGTTGGAAACTGTGGCTGTGCTTTC
CTACAGATTGATGTGGGTCGTTCTTCCTGGCCCCTGGACAGACCTTTCGTCACCCTGCTCCCTGCCACC
ATGCTAATGTCCCGCACTGACTCCAAGTCCAAGGAGAGAACCGCTGACTTCAGGGTCCGGATGTTTAAAGATGGT
GATTTCCTGACTCCAGCTGCTTGGGATCGACTTCGACTTGATTGACCTGCTCCAACCTTTCACA
CGTCATCAGTCCTTTGGCCTGGCCTTCCTACGAGTGGTTCCTCTCTGGCTGTGGAGTCTGATCCT
GTAGATCCCTGACTAATTCTCAAGGCCCCTGGGAGCTCTGGGAGACGTTCTGGAGTCTACTGCT
AGGCCCTGGCTGACTAATTCTCAAGGACAAGGCCATATGCTCATGGGCACAAAAAACCATCCCGTGTCCCCTGAG
GTTGATATTTCTCAAGGACAAGGCCATATGCTCATGGGCACAAAAAACCATCCCGTGTCCCCTGAG
CACCAAGGAAATTTCAGAGTCTCAAGGGTATGTTGAAGCAGTTGCAGCCAGGGCCTCTGGGGGCAGC
CCGCATGGTGCTTTCTGCTGCCCGTAA - 3' (SEQ ID NO:27)

FIG. 15B

MAPVKISHVVSFSSQDPKYPVENLLNPDSHRGPWLSCPQDKTGQLKVEFQLERAVPISYIDVGNCGCA
FLQIDVGRSSWPLDRPFVTLLPATMLMSRTDSKSGKNRSGVRMFKDGDFLTPASGESWDRLRLTCSQP
FTRHQSFGLAFLRVRSSLGSLADPVVDPSAPGSSGLNQNSTDVLESDPRPWLTNPSIRRTFFPDPQTY
VPAVDISQGQHIAHGHKNPSRGPLEHQGNFRAQGYVEAVAARASGAGSPHGAFCCP
(SEQ ID NO:28)

FIG. 16A

```
5'-
ATGGCTCCTGTGAAGATCAGCCATGTGGTGTCATTTTCCTCTCAGGATCCCAAATATCC
TGTGGAGAACTTGCTGAACCCAGACAGTCACAGGGGACCCTGGCTCAGCTGCCCTCAGG
ACAAGACTGGACAACTGAAAGTGGAGTTTCAGCTGGAGAGGGCAGTGCCCATAAGCTAT
ATTGATGTTGGAAACTGTGGCTGTGCTTTCCTACAGATTGATGTGGGTCGTTCTTCCTG
GCCCCTGGACAGACCTTTCGTCACCCTGCTCCCTGCCACCATGCTAATGTCCCGCACTG
ACTCCAAGTCGGGGAAGAACCGCTCAGGGGTCCGGATGTTTAAAGATGGTGATTTCCTG
ACTCCAGCCTCAGGAGAGTCCTGGGATCGACTTCGATTGACCTGCTCCCAACCTTTCAC
ACGTCATCAGTCCTTTGGCCTGGCCTTCCTACGAGTGCGTTCCTCTCTGGGCTCTCTGG
CTGACCCTGTAGTAGATCCCTCAGCCCTGGGAGCTCTGGGCTTAACCAGAACTCTACA
GATGTGCTGGAGTCTGATCCTAGGCCCTGGCTGACTAATCCTTCTATCCGGAGGACATT
CTTCCCCGATCCCCAGACGAGCACCAAGGAAATTTCAGAGCTCAAGGGTATGTTGAAGC
AGTTGCAGCCAGGGCCTCTGGGCGGGCAGCCCGCATGGTGCTTTCTGCTGCCCGTAAG
GCCCCTCCAGCCAGTGTGGTAAGCCCAAACAACAGCCACGGAGAACCAGGTCCCAGCCG
TGCAGAGAGTGCAGAGCCCAGAGCAGAAGAACCAAACAGGAAGACGGCTGTGGGCAGAA
GGAAGAGGAGGAAAGTGCAGGAGCCAAGGAGATCGTTGTCCAACTCGAGTTCTCAGCCA
AATAGGAGGACAGGAAGGACAAGACAAAGACAGCACCGACCTCAGACCAAAAGTGATGA
CGGTGGTGTGCAGGCTGCTGGACAGTGTCCTATTTGTGCAGGTTTCTTCAGTATTGAGA
CTCTTCCCCAGCATGCTGCAACTTGTGGAGAGAGCCCCCCACCCCAGCCAGCTTCTCCT
GCCTCCTTGTCTTCCTCGGAGTCCGTGCTGAGACGTCATCATGTGGCACTAACACCCGT
TCCCCTTGTCCCCAAGCCACAGCCCAACTGGACTGAGATTGTGAACAAAAAGCTCAAAT
TCCCCCCCACACTCCTGCGTGCCATCCAGGAGGGCCAGCTGGGTCTTGTGCAGCAGCTG
CTGGAATCCAGTTCCGATGCCTCGGGTGCTGGGCCAGGTGGTCCTCTGCGGAATGTGGA
AGAGTCTGAGGACCGCTCCTGGAGGGAAGCCCTCAACCTGGCCATCCGCCTGGGCCACG
AGGTCATCACTGATGTTCTGCTGGCCAATGTCAAATTCGACTTTCGGCAGATCCACGAA
GCCCTGCTAGTGGCTGTGGACACAAACCAGCCAGCAGTGGTGCGTCGCCTGCTAGCGCG
GCTGGAGCGGGAGAAAGGTCGAAAAGTAGACACCAAGTCTTTCTCTCTAGCCTTCTTTG
ACTCATCGATTGATGGCTCCCGCTTTGCCCCTGGTGTCACTCCACTCACACTGGCCTGC
CAGAAGGACCTGTATGAGATTGCCCAGCTGCTTATGGACCAGGGCCATACCATTGCTCG
GCCCCACCCAGTTTCCTGTGCCTGCCTCGAGTGCAGCAATGCCCGCCGATACGACCTGC
TGAAGTTCTCACTATCCCGAATCAACACCTACCGAGGCATTGCAAGCCGGGCTCACCTC
TCGCTGGCCAGTGAGGATGCCATGCTGGCCGCTTTTCAGCTCAGCCGGGAGCTCAGGCG
CCTTGCACGAAAGGAGCCTGAGTTTAAGCCTCAGTACATTGCCCTGGAGTCTCTCTGCC
AGGACTATGGCTTCGAGTTGCTGGGCATGTGCCGAAATCAGAGTGAGGTCACCGCAGTG
CTCAATGACCTGGGTGAGGATAGTGAGACTGAGCCTGAGGCTGAGGGCCTGGGTCAGGC
CTTTGAGGAGGGCATCCCCAACCTGGCAAGACTGCGGTTGGCTGTCAACTACAACCAGA
AACAGTTTGTAGCACATCCCATCTGCCAGCAAGTTCTGTCTTCCATCTGGTGTGGGAAC
CTGGCTGGCTGGCGTGGAAGCACCACCATCTGGAGGCTCTTTGTTGCCTCCCTCATCTT
CCTCACCATGCCCTTCCTCTGCATTGGCTACTGGCTGGCGCCCAAGTCCCAGCTGGGCC
GCCTGCTGAAGATCCCGGTGCTGAAGTTCCTGCTGCATTCTGCCTCCTACCTGTGGTTC
CTTATCTTCTTGCTGGGAGAGTCTCTGGTCATGGAGACCCAGCTGAGCACCTTCAAGG
CCGCAGCCAGAGTGTCTGGGAGACTTCACTACATATGATCTGGGTCACAGGCTTCCTAT
GGTTTGAATGCAAGGAGGTGTGGATCGAGGGCTTGCGGAGCTACCTCCTGGACTGGTGG
AACTTCCTGGACGTG
```

FIG. 16B

```
GTCATCCTGTCCCTGTACTTGGCATCCTTTGCACTGCGCCTCCTCCTGGCTGGGCTTGC
CTACATGCACTGCCGTGATGCCTCAGACAGCACCACCTGCCGCTGTTTCACCACAGCTG
AGAGAAGTGAGTGGCGTACAGAGGACCCCCAGTTTCTGGCTGAGGTGCTCTTTACTGTC
ACCAGCATGCTCAGCTTCACCCGACTGGCATATATTCTGCCAGCTCACGAATCGCTGGG
CACACTGCAGATCTCCATCGGCAAGATGATTGACGACATGATCCGGTTCATGTTCATCC
TCATGATCATCCTGACTGCCTTCCTCTGTGGCCTCAACAACATCTATGTGCCCTACCAG
GAATCCGAGAAGCTAGGCAATTTCAACGAAACGTTCCAGTTTCTCTTTTGGACCATGTT
CGGCATGGAAGAGCACACAGTGGTGGACATGCCTCAGTTCCTGGTGCCTGAGTTCGTGG
GCAGGGCCATGTACGGCATCTTTACCATCGTCATGGTCATTGTGCTACTTAACATGCTT
ATTGCCATGATCACCAACTCCTTCCAGAAGATCGAGGATGATGCTGATGTGGAGTGGAA
GTTTGCTCGCTCCAAGCTCTACCTGTCCTACTTCCGAGAGGGTCTGACGCTGCCTGTGC
CCTTTAACATCCTGCCATCCCCAAAGGCCGCCTTCTACCTCGTCAGGAGAATTTTCCG
GTTCCTTTGCTGTGGCTCCTCCTGCTGCAAAGCCAAGAAGTCGGACTACCCGCCCATCG
GGACCTTTACCAACCCCGGGGCAAGGGCGGGCTCCGCCGGGGAAGGAGAACGCGTGTCC
TACCGCCTTCGAGTCATCAAGGCTCTGGTGCAGCGCTACATAGAGACTGCCCGGCGCGA
GTTCGAGGAGACCCGTCGGAAAGACCTGGGCAACAGACTGACAGAGCTGACCAAGACTG
TGTCTCGACTGCAAAGCGAGGTGGCCAGTGTGCAGAAGAACCTGGCGGCGGGAGGGGCA
CCACGGCCTCCGGATGGTGCCAGCATCCTCAGTAGATACATCACCCGAGTGCGCAACAG
CTTCCAGAACCTGGGCCCCCTACCTCTGACACCCCAGCAGAGCTGACTATGCCTGGGA
TTGTGGAGACCGAAGTCTCTTTAGGAGATGGCCTTGATGGCACAGGTGAAGCTGGAGCT
CCCGCTCCTGGAGAGCCCGGCTCTTCCTCCTCTGCCCATGTGCTGGTTCACAGGGAGCA
AGAAGCAGAGGGGTCAGGGACTTGCTCCTGGAAGGAGATCTGGAGACCAAGGGCGAGT
CCTAA-3' (SEQ ID NO:29)
```

FIG. 16C

```
MAPVKISHVVSFSSQDPKYPVENLLNPDSHRGPWLSCPQDKTGQLKVEFQLERAVPISY
IDVGNCGCAFLQIDVGRSSWPLDRPFVTLLPATMLMSRTDSKSGKNRSGVRMFKDGDFL
TPASGESWDRLRLTCSQPFTRHQSFGLAFLRVRSSLGSLADPVVDPSAPGSSGLNQNST
DVLESDPRPWLTNPSIRRTFFPDPQTSTKEISELKGMLKQLQPGPLGRAARMVLSAARK
APPASVVSPNNSHGEPGPSRAESAEPRAEEPNRKTAVGRRKRRKVQEPRRSLSNSSSQP
NRRTGRTRQRQHRPQTKSDDGGVQAAGQCPICAGFFSIETLPQHAATCGESPPPQPASP
ASLSSSESVLRRHHVALTPVPLVPKPQPNWTEIVNKKLKFPPTLLRAIQEGQLGLVQQL
LESSSDASGAPGGPLRNVEESEDRSWREALNLAIRLGHEVITDVLLANVKFDFRQIHE
ALLVAVDTNQPAVVRRLLARLEREKGRKVDTKSFSLAFFDSSIDGSRFAPGVTPLTLAC
QKDLYEIAQLLMDQGHTIARPHPVSCACLECSNARRYDLLKFSLSRINTYRGIASRAHL
SLASEDAMLAAFQLSRELRRLARKEPEFKPQYIALESLCQDYGFELLGMCRNQSEVTAV
LNDLGEDSETEPEAEGLGQAFEEGIPNLARLRLAVNYNQKQFVAHPICQQVLSSIWCGN
LAGWRGSTTIWRLFVASLIFLTMPFLCIGYWLAPKSQLGRLLKIPVLKFLLHSASYLWF
LIFLLGESLVMETQLSTFKGRSQSVWETSLHMIWVTGFLWFECKEVWIEGLRSYLLDWW
NFLDVVILSLYLASFALRLLLAGLAYMHCRDASDSTTCRCFTTAERSEWRTEDPQFLAE
VLFTVTSMLSFTRLAYILPAHESLGTLQISIGKMIDDMIRFMFILMIILTAFLCGLNNI
YVPYQESEKLGNFNETFQFLFWTMFGMEEHTVVDMPQFLVPEFVGRAMYGIFTIVMVIV
LLNMLIAMITNSFQKIEDDADVEWKFARSKLYLSYFREGLTLPVPFNILPSPKAAFYLV
RRIFRFLCCGSSCCKAKKSDYPPIGTFTNPGARAGSAGEGERVSYRLRVIKALVQRYI
ETARREFEETRRKDLGNRLTELTKTVSRLQSEVASVQKNLAAGGAPRPPDGASILSRYI
TRVRNSFQNLGPPTSDTPAELTMPGIVETEVSLGDGLDGTGEAGAPAPGEPGSSSSAHV
LVHREQEAEGSGDLLLEGDLETKGES (SEQ ID NO:30)
```

FIG. 17A

5'-
ATGGCTCCTGTGAAGATCAGCCATGTGGTATCATTTCTTCTCAGATCCCAAGTATCCTGTAGAGAA
CTTGCTAAACCCAGATAGTCCAAGGAGACCTTGGCTGCCTCGGCTGCCCTCAGGACAAGAGTGGGCAATTGA
AAGTAGAACTACAGCTGGAGAGGGCAGTGCCCACTGGTAACTGTGGCTGTGCG
TTCCTGCAAATTGATGTGGGCCATTCTTCCTGGACAGACCTTTCATAACCCTGCTCCCTGC
AACCACGTCAAATGTCTCTAACTGATTCAAAGCAGGAGAAGAACCGCTCCGGGGTCCGCATGTTAAAG
ATGTTGATTCCTGGCTCCAGCTCCAGGAGAGTTATGGGATGACTTCGCCTGACCTGCTCCCGACCC
TTCACGGGTCATCAGTCCTTTGGCCTGAGCCCTTCTGAGCTCTGAGCTCTGAGCTCTGAGCTCTGACTCCTTAGATGA
CTCTGTGGGTCCCCTCAGCCTTCTGACTTCTGACTTCTGAAGAAGATAAGAGAGTTAAGACATGTT
TTTTCTCCTGGAGTCTGAAGAAGATGCTGAAGTCAGCAGATCTCTTTTGTCCATCAATTTGAAT
GATCTTCAGTTTGCAGCAGATGCTGAAGTCAGCAGATCTAATTGCATGTTCATCAGCATTGCACT
TCAGTCTGCAATGATATAATTCTGA - 3' (SEQ ID NO:31)

FIG. 17B

MAPVKISHVV SFSSQDPKYP VENLLNPDSP RRPWLGCPQD KSGQLKVELQ
LERAVPTGYI DVGNCGCAFL QIDVGHSSWP LDRPFITLLP ATTLMSLTDS
KQGKNRSGVR MFKDVDFLAP ASGELWDRLR LTCSRPFTRH QSFGLAFLRV
CSSLDSLDDS VVGPSALLSS VLNKIREFKT CFFSWSLKKM ELEFSPLLLS
INLNDLQFAA DAEVSTVSNC MFISIALQSA MIIF (SEQ ID NO:32)

FIG. 18

5'-
ATGGCTCCTGTGAAGATCAGCAGCCATGTGGTGTCATTTCCTCTCAGGATCCCAAATATCCTGTGGAGAACTTGCTG
AACCCAGACAGTCACAGGGGACCCTGGCTGCCCTCAGCTGCCTCAGGACAAGAAGACTGACAACTGAAAGTGGAGTTTCAG
CTGGAGAGGGCAGTGCCCATAAGCTATATTGATGTTGGAAACTGTGGCTGTGCTTCCTACAGATTGATGTGGGT
CGTTCTTCCTGGCCCCTGGACAGACCTTTCGTCGTCCCTGCTCCCTGCCACCATGTCTAATGTCCCCACTGACTCC
AAGTCGGGGAAGAACCGCTCAGGGGTCCGGATGTTTAAAGATGTTGATTTCCTGACTCCAGCCTCAGGAGAGTCC
TGGGATCGACTTCGATTGACCTGCTCCCAACCTTTCACACGTCATCAGTCTTGCCTGGCCTTCCTACGAGTG
CGTTCCTCTCTGGGTCTGGAGTCTGATCCTGACTAATCCTTCTATCCGGAGACATTCTTCCCGAT
TCTACAGATGTGCTGAGCACCAAGAGAAATTTCAGACTCAAGGTATGTTGAAGCAGTTGCAGCCAGGCCTCTGGGGCGG
CCCCAGACGAGCAGCCATGGTGCTTCTGCTGCCCGTAAGGCCCCTCCAGTGTGGTAAGCCAAACAACAGCCACGGA
GCAGCCCGCATGGTGCTTCTGCTGCCCGTAAGGCCCCTCCAGTGTGGTAAGCCAAACAACAGCCACGGA
GAACCAGGTCCCAGCCGTGCAGAGAGTGCAGAGCCAAGGAGATCGTTGTCCAACTCGAGTTCTCAGCCAAATAGGAGGACAGGA
AGGAAGAAGAAAGAGCAAGACCACGACCTCAGACCAAAAGTGATGACGGTGGTGTGCAACTGTCTGTGACAGTGTCCT
AGGACAAGAAAGACAGCACCGACCTCAGACCAAAAGTGATGACGGTGGTGTGCAACTGTCTGTGACAGTGTCCT
ATTTGTGCAGTTTCTTCAGTATTGAGACTCTTCCTGGAGTCCGTGCTGTGGGTCTCCTCCCCAGCATGCTGAGAGCCCCACCCAG
CCAGCTTCCTGCCTCCTTGTCTTCCTCCGGAGTCCGTGCTGTGGGTCTCCTCCCCAGCATGCTGAGAGCCCCACCCAG
TCCTGGGTCCAGTGCCCTATCTGTGAATTACAGTTCTCAGCAAGAGAAATAGAAGAACATGCCGCCACCT
GAAGTTTGCCAGCCTGA -3' (SEQ ID NO:33)

```
  1  M A P V K I S H V V S F S S Q D P K Y P V E N L L N P D S H   mouse
  1  - - - - - - - - - - - - - - - - - - - - - - - - - - - - - -   human 31  R G P W L S C P Q D K T G Q L K V E F Q L E R A V P I S Y I   mouse
 31  - R - - - G - - - - - S - - - - - - L - - - - - - - T G - -   human 61  D V G N C G C A F L Q I D V G R S S W P L D R P F V T L L P   mouse
 61  - - - - - - - - - - - - - - H - - - - - - - - - I - - - -   human 91  A T M L M S R T D S K S G K N R S G V R M F K D G D F L T P   mouse
 91  - - T - - - L - - - - Q - - - - - - - - - - - - V - - - A -   human 121  A S G E S W D R L R L T C S Q P F T R H Q S F G L A F L R V   mouse
121  - - - - L - - - - - - - R - - - - - - - - - - - - - - - -   human 151  R S S L G S L A D P V V D P S A P G S S G L N Q N S T D V L   mouse
151  C - - - D - - D - S - - G - - - L L - - V - - K I R E F K T   human 181  E S D P R P W L T N P S I R R T F F P D P Q T S T K E I S E   mouse
181  C F F S W S L K K M E L E F S P L L L S I N L N D L Q F A A   human 211  L K G M L K Q L Q P G P L G R A A R M V L S A A R K A P P A   mouse
211  D A E V S T V S N C M F I S I - L Q S A M I I F . (SEQ ID NO:35)  human 241  S V V S P N N S H G E P G P S R A E S A E P R A E E P N R K   mouse
234                                                                 human 271  T A V G R R K R R K V Q E P R R S L S N S S S Q P N R R T G   mouse
234                                                                 human 301  R T R Q R Q H R P Q T K S D D G G V Q A A G Q C P I C A G F   mouse
234                                                                 human 331  F S I E T L P Q H A A T C G E S P P P Q P A S P A S L S S S   mouse
234                                                                 human 361  E S V L W V S S P E S S P P P S W S Q C P I C E L Q F S A R   mouse
234                                                                 human 391  E I E E H A S V C G E V L P A . (SEQ ID NO:34)                .mouse
234                                                                 human
```

FIG. 19

RT-PCR of new 5' coding sequence of mouse trpc2 from testis

A= transcript with coding exon
B= transcript lacking coding exon

SEQUENCE LISTING

<160> NUMBER OF SEQ ID NOS: 39

<210> SEQ ID NO 1
<211> LENGTH: 255
<212> TYPE: PRT
<213> ORGANISM: Mus musculus

<400> SEQUENCE: 1

Met Asp Ser Pro Cys Thr Ser Glu Ser Ile Tyr Asn Leu Ile Pro Ser
1               5                   10                  15

Asp Leu Lys Glu Pro Pro Gln His Pro Arg Tyr Thr Ser Leu Phe Arg
            20                  25                  30

Ala Thr Ile Lys Asn Asp Met Lys Lys Phe Lys Thr Ala Met Lys Thr
        35                  40                  45

Met Gly Pro Ala Lys Val Glu Ile Pro Ser Pro Lys Asp Phe Leu Lys
    50                  55                  60

Lys His Ser Lys Glu Lys Thr Leu Pro Pro Lys Lys Lys Phe Asn Arg
65                  70                  75                  80

Cys Ser Pro Lys Lys Pro Ala Val Pro Leu Arg Thr Asp His Pro Val
                85                  90                  95

Met Gly Ile Gln Ser Gly Lys Asn Phe Ile Asn Thr Asn Ala Ala Asp
            100                 105                 110

Val Ile Met Gly Val Ala Lys Lys Pro Lys Pro Ile Tyr Val Asp Lys
        115                 120                 125

```
Arg Thr Gly Asp Lys His Asp Leu Glu Thr Ser Gly Leu Phe Pro Lys
        130                 135                 140

Tyr Ile Asn Lys Lys Asp Tyr Gly Ile Thr Pro Glu Tyr Ile Cys Lys
145                 150                 155                 160

Arg Asn Glu Asp Val Lys Lys Ala Gln Glu Glu Tyr Asp Asn Tyr Ile
                165                 170                 175

Gln Glu Asn Leu Lys Lys Ala Ala Met Lys Arg Leu Ser Asp Glu Glu
                180                 185                 190

Arg Glu Ala Val Leu Gln Gly Leu Lys Lys Asn Trp Glu Glu Val His
                195                 200                 205

Lys Glu Phe Gln Ser Leu Ser Val Phe Ile Asp Ser Val Pro Lys Lys
        210                 215                 220

Ile Arg Lys Gln Lys Leu Glu Lys Glu Met Lys Gln Leu Glu His Asp
225                 230                 235                 240

Ile Ser Val Ile Glu Lys His Lys Ile Ile Tyr Ile Ala Asn Lys
                245                 250                 255

<210> SEQ ID NO 2
<211> LENGTH: 255
<212> TYPE: PRT
<213> ORGANISM: Homo sapiens

<400> SEQUENCE: 2

Met Asp Pro Thr Cys Ser Ser Cys Ser Ile Tyr Asn Leu Ile Pro Ser
1               5                   10                  15

Asp Leu Lys Glu Pro Pro Gln Pro Pro Arg Tyr Ile Ser Ile Phe Lys
                20                  25                  30

Ala Thr Val Lys Asp Asp Met Gln Lys Ala Lys Thr Ala Met Lys Thr
                35                  40                  45

Met Gly Pro Ala Lys Val Glu Val Pro Ser Pro Lys Asp Phe Leu Lys
        50                  55                  60

Lys His Ser Lys Glu Lys Thr Leu Pro Pro Lys Lys Asn Phe Asp Arg
65                  70                  75                  80

Asn Val Pro Lys Lys Pro Ala Val Pro Leu Lys Thr Asp His Pro Val
                85                  90                  95

Met Gly Ile Gln Ser Gly Lys Asn Phe Ile Asn Thr Asn Ala Ala Asp
                100                 105                 110

Ile Ile Met Gly Val Ala Lys Lys Pro Lys Pro Ile Tyr Val Asp Lys
        115                 120                 125

Arg Thr Gly Asp Lys His Asp Leu Glu Pro Ser Gly Leu Val Pro Lys
        130                 135                 140

Tyr Ile Asn Lys Lys Asp Tyr Gly Val Thr Pro Glu Tyr Ile Cys Lys
145                 150                 155                 160

Arg Asn Glu Glu Ile Lys Lys Ala Gln Glu Asp Tyr Asp Arg Tyr Ile
                165                 170                 175

Gln Glu Asn Leu Lys Lys Ala Ala Met Lys Arg Leu Ser Asp Glu Glu
                180                 185                 190

Arg Glu Ala Val Leu Gln Gly Leu Lys Lys Asn Trp Glu Glu Val His
                195                 200                 205

Lys Glu Phe Gln Ser Leu Ser Val Phe Ile Asp Ser Ile Pro Lys Lys
        210                 215                 220

Ile Arg Lys Gln Arg Leu Glu Glu Met Lys Gln Leu Glu His Asp
225                 230                 235                 240

Ile Gly Ile Ile Glu Lys His Lys Ile Ile Tyr Ile Ala Asn Ala
                245                 250                 255
```

<210> SEQ ID NO 3
<211> LENGTH: 213
<212> TYPE: PRT
<213> ORGANISM: Mus musculus

<400> SEQUENCE: 3

```
Met Gly Thr Lys Thr His Pro Val Pro Trp Ser Thr Lys Glu Ile
 1               5                  10                  15

Ser Glu Leu Lys Gly Met Leu Lys Gln Leu Gln Pro Gly Pro Leu Gly
            20                  25                  30

Arg Ala Ala Arg Met Val Leu Ser Ala Ala Arg Lys Ala Pro Pro Ala
        35                  40                  45

Ser Val Val Ser Pro Asn Asn Ser His Gly Glu Pro Gly Pro Ser Arg
 50                  55                  60

Ala Glu Ser Ala Glu Pro Arg Ala Glu Glu Pro Asn Arg Lys Thr Ala
 65                  70                  75                  80

Val Gly Arg Arg Lys Arg Arg Lys Val Gln Glu Pro Arg Arg Ser Leu
                85                  90                  95

Ser Asn Ser Ser Ser Gln Pro Asn Arg Arg Thr Gly Arg Thr Arg Gln
            100                 105                 110

Arg Gln His Arg Pro Gln Thr Lys Ser Asp Asp Gly Gly Val Gln Ala
        115                 120                 125

Thr Gly Gln Cys Pro Ile Cys Ala Gly Phe Phe Ser Ile Glu Thr Leu
130                 135                 140

Pro Gln His Ala Ala Thr Cys Gly Glu Ser Pro Pro Gln Pro Ala
145                 150                 155                 160

Ser Pro Ala Ser Leu Ser Ser Glu Ser Val Leu Trp Val Ser Ser
                165                 170                 175

Pro Glu Ser Ser Pro Pro Ser Trp Val Gln Cys Pro Ile Cys Glu
            180                 185                 190

Leu Gln Phe Ser Ala Arg Glu Ile Glu Glu His Ala Ser Val Cys Gly
        195                 200                 205

Glu Val Leu Pro Ala
    210
```

<210> SEQ ID NO 4
<211> LENGTH: 156
<212> TYPE: PRT
<213> ORGANISM: Homo sapiens

<400> SEQUENCE: 4

```
Gly Thr Lys Tyr Ser Leu Phe Pro Cys Arg Asp Lys Glu Ile Ser Glu
 1               5                  10                  15

Leu Lys Arg Asn Ile Lys Thr Leu Gln Pro Gly Pro Thr Gly Arg Ala
            20                  25                  30

Ser Arg His Val Leu Ser Ala Ala His Arg Val Pro Val Ser Val
        35                  40                  45

Ala Ser Pro Lys Asn Asn His Ala Glu Pro Gly Lys Lys Lys Gln Arg
 50                  55                  60

Gln His Arg Ala Gln Ser Ser Gly Gln Asp Ser Gly Gln Cys Pro
 65                  70                  75                  80

Ile Cys Ala Gly Gly Phe Arg Ile Glu Ile Leu Pro Gln His Ala Ala
                85                  90                  95

Thr Cys Gly Glu Thr Ser Pro Pro His Pro Ala Ser Pro Ser Ser Ser
            100                 105                 110
```

```
Ser Ser Ser Ser Gln Ser Val Leu Trp Val Ser Ser Pro Glu Ser Ser
        115                 120                 125

Pro Pro Val Ser Trp Val Pro Cys Pro Ile Cys Gln Leu Arg Phe Ser
        130                 135                 140

Ala Arg Val Glu Glu His Ala Ser Ile Cys Gly Asp
145                 150                 155

<210> SEQ ID NO 5
<211> LENGTH: 25
<212> TYPE: PRT
<213> ORGANISM: Mus musculus

<400> SEQUENCE: 5

Leu Pro Gln His Ala Ala Thr Cys Gly Glu Ser Pro Pro Gln Pro
1               5                   10                  15

Ala Ser Pro Ala Ser Leu Ser Ser Ser
            20                  25

<210> SEQ ID NO 6
<211> LENGTH: 26
<212> TYPE: PRT
<213> ORGANISM: Mus musculus

<400> SEQUENCE: 6

Leu Pro Gln His Ala Ala Thr Cys Gly Gly Glu Ser Pro Pro Pro Gln
1               5                   10                  15

Pro Ala Ser Pro Ala Ser Leu Ser Ser Ser
            20                  25

<210> SEQ ID NO 7
<211> LENGTH: 25
<212> TYPE: PRT
<213> ORGANISM: Homo sapiens

<400> SEQUENCE: 7

Leu Pro Gln His Ala Ala Thr Cys Gly Glu Thr Ser Pro Pro His Pro
1               5                   10                  15

Ala Ser Pro Ser Ser Ser Ser Ser Ser
            20                  25

<210> SEQ ID NO 8
<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 8

Leu Pro Gln His Ala Ala Thr Cys Gly Glu Ser Pro Pro Gln Pro
1               5                   10                  15

Ala Ser Pro Ala Ser Leu Ser Ser Ser
            20                  25

<210> SEQ ID NO 9
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 9

Ile Pro Ser Asp Leu Lys Glu Pro Pro Gln His Pro Arg Tyr
```

<210> SEQ ID NO 10
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 10

Ser Val Pro Lys Lys Ile Arg Lys Gln Lys Leu Glu Lys Glu Met Lys
 1               5                  10                  15
Gln

<210> SEQ ID NO 11
<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 11

Gln Ser Ala Pro Leu Pro Ser His Pro Leu Pro Gly Ser Cys Pro Glu
 1               5                  10                  15
Ser Pro Thr Gln Ala Ala Ser Ser Ala
            20                  25

<210> SEQ ID NO 12
<211> LENGTH: 1200
<212> TYPE: DNA
<213> ORGANISM: Mus musculus

<400> SEQUENCE: 12

```
gaccacgtgg tcaacaacgc taaacagact cggagcagaa ttattttctt cctgaaaaag    60
ggactgttac gaaagggtca aagggaaatt acacgaaaga gaaattttag ttctttgata   120
agaaagtaag aaaagaaaaa ggcggtgaga gaaggagttg agacagtggg aaagtgagcc   180
aaaaagctga gtacttgtta aggaattcct tggtggccat ggactcaccc tgcacttccg   240
agagtattta acctcata cccagtgact tgaaggagcc gccccagcat cctaggtata   300
catcactgtt tagagcaact ataaaaaatg acatgaagaa attaaaacg gcaatgaaaa   360
ccatgggacc tgcaaaagta gagatacctt cccccaagga ttttctaaag aagcattcca   420
aggaaaaaac actaccacca aaaaaaagt ttaataggtg ctctcccaag aagcctgcag   480
tgcccttgag aaccgatcat ccagttatgg aatacagag tggaaaaaac ttcataaaca   540
caaatgcagc tgacgtcatc atgggcgtgg ccaaaaagcc caagccgatt tatgttgaca   600
aagaactgg agataagcat gaccttgaaa cttcagggct attccccaag tacatcaaca   660
aaaggatta tggcatcacg cctgagtaca tatgcaagcg aaatgaggat gtgaagaaag   720
cacaagaaga gtatgacaat tacatccagg agaacctcaa gaaagcggcc atgaagagac   780
tctctgacga agaaagggag gcagttctgc agggactgaa gaagaactgg gaagaggtgc   840
acaaagagtt ccaatccctc tcggtcttca ttgattctgt accaagaag attcgcaagc   900
agaagctgga aaaagagatg aagcagctgg aacacgacat cagtgtcatt gagaagcaca   960
agatcatcta catcgctaac aagtgagcca actgttgcag acagaaaaa agccacatgg   1020
ccatcacact aaacccactc ttctcaaaga ggactatgaa gagaataaag ttttcaccga   1080
aaatgtaggg gcagtgttga agaatagtt gaattatttg cttgctctag agaaaatttt   1140
```
ctcctccact gtcagagttc tacttataaa caaaccatta aagtcagaag ctgcaccttg    1200

<210> SEQ ID NO 13
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 13

Met Tyr Pro Tyr Asp Val Pro Asp Tyr Ala
1               5                  10

<210> SEQ ID NO 14
<211> LENGTH: 30
<212> TYPE: PRT
<213> ORGANISM: Artificial Sequence
<220> FEATURE:
<223> OTHER INFORMATION: Synthetically generated peptide

<400> SEQUENCE: 14

Arg Gln Ile Lys Ile Trp Phe Gln Asn Arg Arg Met Lys Trp Lys Lys
1               5                  10                  15

Leu Gly Cys Gly Met Tyr Pro Tyr Asp Val Pro Asp Tyr Ala
            20                  25                  30

<210> SEQ ID NO 15
<211> LENGTH: 59
<212> TYPE: PRT
<213> ORGANISM: Homo sapiens

<400> SEQUENCE: 15

Gly Thr Lys Tyr Ser Leu Phe Pro Cys Arg Asp Lys Glu Ile Ser Glu
1               5                  10                  15

Leu Lys Arg Asn Ile Lys Thr Leu Gln Pro Gly Pro Thr Gly Arg Ala
            20                  25                  30

Ser Arg His Val Leu Ser Ala Ala His Arg Val Pro Val Ser Val
        35                  40                  45

Ala Ser Pro Lys Asn Asn His Ala Glu Pro Gly
    50                  55

<210> SEQ ID NO 16
<211> LENGTH: 16
<212> TYPE: PRT
<213> ORGANISM: Mus musculus

<400> SEQUENCE: 16

Gly Phe Phe Ser Ile Glu Thr Leu Pro Gln His Ala Ala Thr Cys Gly
1               5                  10                  15

<210> SEQ ID NO 17
<211> LENGTH: 20
<212> TYPE: PRT
<213> ORGANISM: Homo sapiens

<400> SEQUENCE: 17

Pro Ile Cys Gln Leu Arg Phe Ser Ala Arg Glu Val Glu Glu His Ala
1               5                  10                  15

Ser Ile Cys Gly
            20

<210> SEQ ID NO 18
<211> LENGTH: 51

<212> TYPE: PRT
<213> ORGANISM: Artificial Sequence
<220> FEATURE:
<223> OTHER INFORMATION: Synthetically generated peptide

<400> SEQUENCE: 18

Arg Gln Ile Lys Ile Trp Phe Gln Asn Arg Arg Met Lys Trp Lys Lys
1               5                   10                  15
Leu Pro Gln His Ala Ala Thr Cys Gly Glu Thr Ser Pro Pro His Pro
            20                  25                  30
Ala Ser Pro Ser Ser Ser Ser Ser Met Tyr Pro Tyr Asp Val Pro
        35                  40                  45
Asp Tyr Ala
    50

<210> SEQ ID NO 19
<211> LENGTH: 21
<212> TYPE: PRT
<213> ORGANISM: Artificial Sequence
<220> FEATURE:
<223> OTHER INFORMATION: Synthetically generated peptide

<400> SEQUENCE: 19

Lys Val Val Ala His Asn Lys Phe His Asp Phe Ala Asp Arg Lys Asp
1               5                   10                  15
Trp Asp Ala Phe His
            20

<210> SEQ ID NO 20
<211> LENGTH: 936
<212> TYPE: DNA
<213> ORGANISM: Homo sapiens

<400> SEQUENCE: 20
gactgctaag aggggttaa  aggggacga  tgtgaaggag agaacctgtg gtccttcaga      60
aggcgaagaa gaaagaaagg ggaagcagtg aagaaaggga cggagatact gggacaggga     120
gaaaaaagtt gtggagagta gcttttaagg agtcatttgg tggccatgga tccaacgtgc     180
tcttctgagt gcatttataa cctcataccc agtgacttga aggagcctcc ccagcctcct     240
aggtacatat ccattttaa  ggcaactgta aagatgaca  tgcaaaaagc taaaactgca     300
atgaaaacta tgggaccagc aaaagttgaa gtaccttctc caaggatttt cctaaagaaa     360
cattcaaagg agaaaactct accacccaaa aaaactttg  atcggaacgt gcccaaaaag     420
cctgctgtgc cattgaagac tgatcatcct gtcatgggaa tacagagtgg aaaaaatttt     480
ataaatacaa atgcagctga tatcatcatg ggagtggcta aaaagcctaa accaattat      540
gttgataaaa gaactggaga caagcatgat cttgagcctt caggactagt tccaaagtac     600
atcaataaaa aggattatgg tgtcacacct gaatacatat gtaagcgaaa cgaggaaata     660
aagaaagccc aagaagacta tgatcgttat atccaggaaa accttaagaa agcagctatg     720
aaaaggctct ccgatgaaga agggaggca  gttttgcagg ggctgaaaaa gaactgggaa     780
gaggtgcata aagaattcca gtccctctcg gtctttatag attctatacc aaagaagatc     840
cgcaagcaga ggctggaaga agaaatgaaa caactagaac acgacattgg cataattgaa     900
aagcacaaga ttatttatat tgccaataac gcatga                              936

<210> SEQ ID NO 21
<211> LENGTH: 279
<212> TYPE: DNA

<213> ORGANISM: Mus musculus

<400> SEQUENCE: 21

| | | |
|---|---|---|
| atggctcctg tgaagatcag ccatgtggtg tcattttcct ctcaggatcc caaatatcct | 60 |
| gtggagaact tgctgaaccc agacagtcac aggggaccct ggctcagctg ccctcaggac | 120 |
| aagactggac aactgaaagt ggagtttcag ctggagaggg cagtgcccat aagctatatt | 180 |
| gatgttggaa actgtggctg tgctttccta cagattgatg tgggtcgttc ttcctggccc | 240 |
| ctggacagac ctttcgtcac cctgctccct gccaccatg | 279 |

<210> SEQ ID NO 22
<211> LENGTH: 93
<212> TYPE: PRT
<213> ORGANISM: Mus musculus

<400> SEQUENCE: 22

Met Ala Pro Val Lys Ile Ser His Val Val Ser Phe Ser Ser Gln Asp
1               5                   10                  15
Pro Lys Tyr Pro Val Glu Asn Leu Leu Asn Pro Asp Ser His Arg Gly
            20                  25                  30
Pro Trp Leu Ser Cys Pro Gln Asp Lys Thr Gly Gln Leu Lys Val Glu
        35                  40                  45
Phe Gln Leu Glu Arg Ala Val Pro Ile Ser Tyr Ile Asp Val Gly Asn
    50                  55                  60
Cys Gly Cys Ala Phe Leu Gln Ile Asp Val Gly Arg Ser Ser Trp Pro
65                  70                  75                  80
Leu Asp Arg Pro Phe Val Thr Leu Leu Pro Ala Thr Met
                85                  90

<210> SEQ ID NO 23
<211> LENGTH: 366
<212> TYPE: DNA
<213> ORGANISM: Mus musculus

<400> SEQUENCE: 23

| | | |
|---|---|---|
| atggctcctg tgaagatcag ccatgtggtg tcattttcct ctcaggatcc caaatatcct | 60 |
| gtggagaact tgctgaaccc agacagtcac aggggaccct ggctcagctg ccctcaggac | 120 |
| aagactggac aactgaaagt ggagtttcag ctggagaggg cagtgcccat aagctatatt | 180 |
| gatgttggtg atttcctgac tccagcctca ggagagtcct gggatcgact tcgattgacc | 240 |
| tgctcccaac ctttcacacg tcatcagtcc tttggcctgg ccttcctacg agtgcgttcc | 300 |
| tctctgggct ctctggctga ccctgtagta gatccctcag ccctgggag ctctgggctt | 360 |
| aaccag | 366 |

<210> SEQ ID NO 24
<211> LENGTH: 122
<212> TYPE: PRT
<213> ORGANISM: Mus musculus

<400> SEQUENCE: 24

Met Ala Pro Val Lys Ile Ser His Val Val Ser Phe Ser Ser Gln Asp
1               5                   10                  15
Pro Lys Tyr Pro Val Glu Asn Leu Leu Asn Pro Asp Ser His Arg Gly
            20                  25                  30
Pro Trp Leu Ser Cys Pro Gln Asp Lys Thr Gly Gln Leu Lys Val Glu
        35                  40                  45

```
Phe Gln Leu Glu Arg Ala Val Pro Ile Ser Tyr Ile Asp Val Gly Asp
     50                  55                  60
Phe Leu Thr Pro Ala Ser Gly Glu Ser Trp Asp Arg Leu Arg Leu Thr
 65                  70                  75                  80
Cys Ser Gln Pro Phe Thr Arg His Gln Ser Phe Gly Leu Ala Phe Leu
                 85                  90                  95
Arg Val Arg Ser Ser Leu Gly Ser Leu Ala Asp Pro Val Asp Pro
            100                 105                 110
Ser Ala Pro Gly Ser Ser Gly Leu Asn Gln
        115                 120
```

<210> SEQ ID NO 25
<211> LENGTH: 1218
<212> TYPE: DNA
<213> ORGANISM: Mus musculus

<400> SEQUENCE: 25

| | | |
|---|---|---|
| atggctcctg tgaagatcag ccatgtggtg tcattttcct ctcaggatcc caaatatcct | 60 |
| gtggagaact tgctgaaccc agacagtcac aggggaccct ggctcagctg ccctcaggac | 120 |
| aagactggac aactgaaagt ggagtttcag ctggagaggg cagtgcccat aagctatatt | 180 |
| gatgttggaa actgtggctg tgctttccta cagattgatg tgggtcgttc ttcctggccc | 240 |
| ctggacagac tttcgtcac cctgctccct gccaccatgc taatgtcccg cactgactcc | 300 |
| aagtcgggga agaaccgctc aggggtccgg atgtttaaag atggtgattt cctgactcca | 360 |
| gcctcaggag agtcctggga tcgacttcga ttgacctgct cccaaccttt cacacgtcat | 420 |
| cagtcctttg gcctggcctt cctacgagtg cgttcctctc tgggctctct ggctgaccct | 480 |
| gtagtagatc cctcagcccc tgggagctct gggcttaacc agaactctac agatgtgctg | 540 |
| gagtctgatc ctaggccctg gctgactaat ccttctatcc ggaggacatt cttccccgat | 600 |
| ccccagacga gcaccaagga aatttcagag ctcaagggta tgttgaagca gttgcagcca | 660 |
| gggcctctgg ggcgggcagc ccgcatggtg cttctgctg cccgtaaggc ccctccagcc | 720 |
| agtgtggtaa gccaaacaa cagccacgga gaaccaggtc ccagccgtgc agagagtgca | 780 |
| gagcccagag cagaagaacc aaacaggaag acggctgtgg gcagaaggaa gaggaggaaa | 840 |
| gtgcaggagc caaggagatc gttgtccaac tcgagttctc agccaaatag gaggacagga | 900 |
| aggacaagac aaagacagca ccgacctcag accaaaagtg atgacggtgg tgtgcaggct | 960 |
| gctggacagt gtcctatttg tgcaggtttc ttcagtattg agactcttcc ccagcatgct | 1020 |
| gcaacttgtg gagagagccc cccaccccag ccagcttctc ctgcctcctt gtcttcctcg | 1080 |
| gagtccgtgc tgtgggtctc ctccccagag agctcgccgc caccttcctg ggtccagtgc | 1140 |
| cctatctgtg aattacagtt ctcagcaaga gaaatagaag aacatgccag cgtgtgtggg | 1200 |
| gaagttttgc cagcctga | 1218 |

<210> SEQ ID NO 26
<211> LENGTH: 404
<212> TYPE: PRT
<213> ORGANISM: Mus musculus

<400> SEQUENCE: 26

```
Met Ala Pro Val Lys Ile Ser His Val Val Ser Phe Ser Ser Gln Asp
 1               5                  10                  15
Pro Lys Tyr Pro Val Glu Asn Leu Leu Asn Pro Asp Ser His Arg Gly
             20                  25                  30
```

```
Pro Trp Leu Ser Cys Pro Gln Asp Lys Thr Gly Gln Leu Lys Val Glu
        35                  40                  45

Phe Gln Leu Glu Arg Ala Val Pro Ile Ser Tyr Ile Asp Val Gly Asn
    50                  55                  60

Cys Gly Cys Ala Phe Leu Gln Ile Asp Val Gly Arg Ser Ser Trp Pro
65                  70                  75                  80

Leu Asp Arg Pro Phe Val Thr Leu Leu Pro Ala Thr Met Leu Met Ser
                85                  90                  95

Arg Thr Asp Ser Lys Ser Gly Lys Asn Arg Ser Gly Val Arg Met Phe
                100                 105                 110

Lys Asp Gly Asp Phe Leu Thr Pro Ala Ser Gly Glu Ser Trp Asp Arg
            115                 120                 125

Leu Arg Leu Thr Cys Ser Gln Pro Phe Thr Arg His Gln Ser Phe Gly
        130                 135                 140

Leu Ala Phe Leu Arg Val Arg Ser Ser Leu Gly Ser Leu Ala Asp Pro
145                 150                 155                 160

Val Val Asp Pro Ser Ala Pro Gly Ser Ser Gly Leu Asn Gln Asn Ser
                165                 170                 175

Thr Asp Val Leu Glu Ser Asp Pro Arg Pro Trp Leu Thr Asn Pro Ser
                180                 185                 190

Ile Arg Arg Thr Phe Phe Pro Asp Pro Gln Thr Ser Thr Lys Glu Ile
            195                 200                 205

Ser Glu Leu Lys Gly Met Leu Lys Gln Leu Gln Pro Gly Pro Leu Gly
        210                 215                 220

Arg Ala Ala Arg Met Val Leu Ser Ala Ala Arg Lys Ala Pro Pro Ala
225                 230                 235                 240

Ser Val Val Ser Pro Asn Asn Ser His Gly Glu Pro Gly Pro Ser Arg
                245                 250                 255

Ala Glu Ser Ala Glu Pro Arg Ala Glu Glu Pro Asn Arg Lys Thr Val
                260                 265                 270

Gly Arg Arg Lys Arg Arg Lys Val Gln Glu Pro Arg Arg Ser Leu Ser
            275                 280                 285

Asn Ser Ser Gln Pro Asn Arg Arg Thr Gly Arg Thr Arg Gln Arg
        290                 295                 300

Gln His Arg Pro Gln Thr Lys Ser Asp Asp Gly Gly Val Gln Ala Ala
305                 310                 315                 320

Gly Gln Cys Pro Ile Cys Ala Gly Phe Phe Ser Ile Glu Thr Leu Pro
                325                 330                 335

Gln His Ala Ala Thr Cys Gly Glu Ser Pro Pro Gln Pro Ala Ser
            340                 345                 350

Pro Ala Ser Leu Ser Ser Glu Ser Val Leu Trp Val Ser Ser Pro
        355                 360                 365

Glu Ser Ser Pro Pro Ser Trp Val Gln Cys Pro Ile Cys Glu Leu
        370                 375                 380

Gln Phe Ser Ala Arg Glu Ile Glu Glu His Ala Ser Val Cys Gly Glu
385                 390                 395                 400

Val Leu Pro Ala
```

<210> SEQ ID NO 27
<211> LENGTH: 786
<212> TYPE: DNA
<213> ORGANISM: Mus musculus

<400> SEQUENCE: 27

```
atggctcctg tgaagatcag ccatgtggtg tcattttcct ctcaggatcc caaatatcct      60
gtggagaact tgctgaaccc agacagtcac aggggaccct ggctcagctg ccctcaggac     120
aagactggac aactgaaagt ggagtttcag ctggagaggg cagtgcccat aagctatatt     180
gatgttggaa actgtggctg tgctttccta cagattgatg tgggtcgttc ttcctggccc     240
ctggacagac ctttcgtcac cctgctccct gccaccatgc taatgtcccg cactgactcc     300
aagtcgggga agaaccgctc aggggtccgg atgtttaaag atggtgattt cctgactcca     360
gcctcaggag agtcctggga tcgacttcga ttgacctgct cccaacc ttt cacacgtcat     420
cagtccttg gcctggcctt cctacgagtg cgttcctctc tgggctctct ggctgaccct     480
gtagtagatc cctcagcccc tgggagctct gggcttaacc agaactctac agatgtgctg     540
gagtctgatc ctaggccctg gctgactaat ccttctatcc ggaggacatt cttccccgat     600
ccccagacgt atgtacctgc tgttgatatt tctcaaggac aaggccatat agctcatggg     660
cacaaaaacc catcccgtgg tcccctggag caccaaggaa atttcagagc tcaagggtat     720
gttgaagcag ttgcagccag ggcctctggg gcgggcagcc cgcatggtgc tttctgctgc     780
ccgtaa                                                                786
```

<210> SEQ ID NO 28
<211> LENGTH: 261
<212> TYPE: PRT
<213> ORGANISM: Mus musculus

<400> SEQUENCE: 28

```
Met Ala Pro Val Lys Ile Ser His Val Val Ser Phe Ser Ser Gln Asp
  1               5                  10                  15

Pro Lys Tyr Pro Val Glu Asn Leu Leu Asn Pro Asp Ser His Arg Gly
             20                  25                  30

Pro Trp Leu Ser Cys Pro Gln Asp Lys Thr Gly Gln Leu Lys Val Glu
         35                  40                  45

Phe Gln Leu Glu Arg Ala Val Pro Ile Ser Tyr Ile Asp Val Gly Asn
     50                  55                  60

Cys Gly Cys Ala Phe Leu Gln Ile Asp Val Gly Arg Ser Ser Trp Pro
 65                  70                  75                  80

Leu Asp Arg Pro Phe Val Thr Leu Leu Pro Ala Thr Met Leu Met Ser
                 85                  90                  95

Arg Thr Asp Ser Lys Ser Gly Lys Asn Arg Ser Gly Val Arg Met Phe
            100                 105                 110

Lys Asp Gly Asp Phe Leu Thr Pro Ala Ser Gly Glu Ser Trp Asp Arg
        115                 120                 125

Leu Arg Leu Thr Cys Ser Gln Pro Phe Thr Arg His Gln Ser Phe Gly
    130                 135                 140

Leu Ala Phe Leu Arg Val Arg Ser Ser Leu Gly Ser Leu Ala Asp Pro
145                 150                 155                 160

Val Val Asp Pro Ser Ala Pro Gly Ser Ser Gly Leu Asn Gln Asn Ser
                165                 170                 175

Thr Asp Val Leu Glu Ser Asp Pro Arg Pro Trp Leu Thr Asn Pro Ser
            180                 185                 190

Ile Arg Arg Thr Phe Phe Pro Asp Pro Gln Thr Tyr Val Pro Ala Val
        195                 200                 205

Asp Ile Ser Gln Gly Gln Gly His Ile Ala His Gly His Lys Asn Pro
    210                 215                 220

Ser Arg Gly Pro Leu Glu His Gln Gly Asn Phe Arg Ala Gln Gly Tyr
```

| | | 225 | | | 230 | | | | 235 | | | | 240 | |
|---|---|---|---|---|---|---|---|---|---|---|---|---|---|---|

Val Glu Ala Val Ala Ala Arg Ala Ser Gly Ala Gly Ser Pro His Gly
                    245                   250                 255

Ala Phe Cys Cys Pro
           260

<210> SEQ ID NO 29
<211> LENGTH: 3795
<212> TYPE: DNA
<213> ORGANISM: Mus musculus

<400> SEQUENCE: 29

| | | | | |
|---|---|---|---|---|
| atggctcctg | tgaagatcag | ccatgtggtg | tcattttcct | ctcaggatcc | caaatatcct | 60 |
| gtggagaact | tgctgaaccc | agacagtcac | aggggaccct | ggctcagctg | ccctcaggac | 120 |
| aagactggac | aactgaaagt | ggagtttcag | ctggagaggg | cagtgcccat | aagctatatt | 180 |
| gatgttggaa | actgtggctg | tgcttttcct | acagattgatg | tgggtcgttc | ttcctggccc | 240 |
| ctggacagac | ctttcgtcac | cctgctccct | gccaccatgc | taatgtcccg | cactgactcc | 300 |
| aagtcgggga | agaaccgctc | aggggtccgg | atgtttaaag | atggtgattt | cctgactcca | 360 |
| gcctcaggag | agtcctggga | tcgacttcga | ttgacctgct | cccaaccttt | cacacgtcat | 420 |
| cagtcctttg | gcctggcctt | cctacgagtg | cgttcctctc | tgggctctct | ggctgaccct | 480 |
| gtagtagatc | cctcagcccc | tgggagctct | gggcttaacc | agaactctac | agatgtgctg | 540 |
| gagtctgatc | ctaggccctg | gctgactaat | ccttctatcc | ggaggacatt | cttccccgat | 600 |
| ccccagacga | gcaccaagga | aatttcagag | ctcaagggta | tgttgaagca | gttgcagcca | 660 |
| gggcctctgg | ggcgggcagc | ccgcatggtg | ctttctgctg | cccgtaaggc | ccctccagcc | 720 |
| agtgtggtaa | gcccaaacaa | cagccacgga | gaaccaggtc | ccagccgtgc | agagagtgca | 780 |
| gagcccagag | cagaagaacc | aaacaggaag | acggctgtgg | gcagaaggaa | gaggaggaaa | 840 |
| gtgcaggagc | caaggagatc | gttgtccaac | tcgagttctc | agccaaatag | gaggacagga | 900 |
| aggacaagac | aaagacagca | ccgacctcag | accaaaagtg | atgacggtgg | tgtgcaggct | 960 |
| gctggacagt | gtcctatttg | tgcaggtttc | ttcagtattg | agactcttcc | ccagcatgct | 1020 |
| gcaacttgtg | gagagagccc | cccaccccag | ccagcttctc | ctgcctcctt | gtcttcctcg | 1080 |
| gagtccgtgc | tgagacgtca | tcatgtggca | ctaacacccg | ttccccttgt | ccccaagcca | 1140 |
| cagcccaact | ggactgagat | tgtgaacaaa | aagctcaaat | tccccccac | actcctgcgt | 1200 |
| gccatccagg | agggccagct | gggtcttgtg | cagcagctgc | tggaatccag | ttccgatgcc | 1260 |
| tcgggtgctg | ggccaggtgg | tcctctgcgg | aatgtggaag | agtctgagga | ccgctcctgg | 1320 |
| agggaagccc | tcaacctggc | catccgcctg | gccacgagg | tcatcactga | tgttctgctg | 1380 |
| gccaatgtca | aattcgactt | tcggcagatc | cacgaagccc | tgctagtggc | tgtggacaca | 1440 |
| aaccagccag | cagtggtgcg | tcgcctgcta | gcgcggctgg | agcgggagaa | aggtcgaaaa | 1500 |
| gtagacacca | gtctttctc | tctagccttc | tttgactcat | cgattgatgg | ctcccgcttt | 1560 |
| gcccctggtg | tcactccact | cacactggcc | tgccagaagg | acctgtatga | gattgcccag | 1620 |
| ctgcttatgg | accagggcca | taccattgct | cggccccacc | cagtttcctg | tgcctgcctc | 1680 |
| gagtgcagca | atgcccgccg | atacgacctg | ctgaagttct | cactatcccg | aatcaacacc | 1740 |
| taccgaggca | ttgcaagccg | ggctcacctc | tcgctggcca | gtgaggatgc | catgctggcc | 1800 |
| gcttttcagc | tcagccggga | gctcaggcgc | cttgcacgaa | aggagcctga | gtttaagcct | 1860 |
| cagtacattg | ccctggagtc | tctctgccag | gactatggct | tcgagttgct | gggcatgtgc | 1920 |

```
cgaaatcaga gtgaggtcac cgcagtgctc aatgacctgg gtgaggatag tgagactgag   1980
cctgaggctg agggcctggg tcaggccttt gaggagggca tccccaacct ggcaagactg   2040
cggttggctg tcaactacaa ccagaaacag tttgtagcac atcccatctg ccagcaagtt   2100
ctgtcttcca tctggtgtgg aacctggct ggctggcgtg aagcaccac catctggagg    2160 ctctttgttg cctccctcat cttcctcacc atgcccttcc tctgcattgg ctactggctg   2220
gcgcccaagt cccagctggg ccgcctgctg aagatcccgg tgctgaagtt cctgctgcat   2280
tctgcctcct acctgtggtt ccttatcttc ttgctgggag agtctctggt catggagacc   2340
cagctgagca ccttcaaagg ccgcagccag agtgtctggg agacttcact acatatgatc   2400
tgggtcacag gcttcctatg gtttgaatgc aaggaggtgt ggatcgaggg cttgcggagc   2460
tacctcctgg actggtggaa cttcctggac gtggtcatcc tgtccctgta cttggcatcc   2520
tttgcactgc gcctcctcct ggctgggctt gcctacatgc actgccgtga tgcctcagac   2580
agcaccacct gccgctgttt caccacagct gagagaagtg agtggcgtac agaggacccc   2640
cagtttctgg ctgaggtgct ctttactgtc accagcatgc tcagcttcac ccgactggca   2700
tatattctgc cagctcacga atcgctgggc acactgcaga tctccatcgg caagatgatt   2760
gacgacatga tccggttcat gttcatcctc atgatcatcc tgactgcctt cctctgtggc   2820
ctcaacaaca tctatgtgcc ctaccaggaa tccgagaagc taggcaattt caacgaaacg   2880
ttccagtttc tcttttggac catgttcggc atggaagagc acacagtggt ggacatgcct   2940
cagttcctgg tgcctgagtt cgtgggcagg gccatgtacg gcatctttac catcgtcatg   3000
gtcattgtgc tacttaacat gcttattgcc atgatcacca actccttcca gaagatcgag   3060
gatgatgctg atgtggagtg gaagtttgct cgctccaagc tctacctgtc ctacttccga   3120
gagggtctga cgctgcctgt gccctttaac atcctgccat ccccaaaggc cgccttctac   3180
ctcgtcagga gaattttccg gttcctttgc tgtggctcct cctgctgcaa agccaagaag   3240
tcggactacc cgcccatcgg gacctttacc aaccccgggg caaggcgggg ctccgccggg   3300
gaaggagaac gcgtgtccta ccgccttcga gtcatcaagg ctctggtgca gcgctacata   3360
gagactgccc ggcgcgagtt cgaggagacc cgtcggaaag acctgggcaa cagactgaca   3420
gagctgacca agactgtgtc tcgactgcaa agcgaggtgg ccagtgtgca gaagaacctg   3480
gcggcgggag gggcaccacg gcctccggat ggtgccagca tcctcagtag atacatcacc   3540
cgagtgcgca acagcttcca gaacctgggc ccccctacct ctgacacccc agcagagctg   3600
actatgcctg ggattgtgga gaccgaagtc tctttaggag atggccttga tggcacaggt   3660
gaagctggag ctcccgctcc tggagagccc ggctcttcct cctctgccca tgtgctggtt   3720
cacagggagc aagaagcaga ggggtcaggg gacttgctcc tggaaggaga tctggagacc   3780
aagggcgagt cctaa                                                    3795
```

<210> SEQ ID NO 30
<211> LENGTH: 1264
<212> TYPE: PRT
<213> ORGANISM: Mus musculus

<400> SEQUENCE: 30

```
Met Ala Pro Val Lys Ile Ser His Val Val Ser Phe Ser Ser Gln Asp
  1               5                  10                  15

Pro Lys Tyr Pro Val Glu Asn Leu Leu Asn Pro Asp Ser His Arg Gly
             20                  25                  30
```

```
Pro Trp Leu Ser Cys Pro Gln Asp Lys Thr Gly Gln Leu Lys Val Glu
         35                  40                  45
Phe Gln Leu Glu Arg Ala Val Pro Ile Ser Tyr Ile Asp Val Gly Asn
 50                  55                  60
Cys Gly Cys Ala Phe Leu Gln Ile Asp Val Gly Arg Ser Ser Trp Pro
 65                  70                  75                  80
Leu Asp Arg Pro Phe Val Thr Leu Leu Pro Ala Thr Met Leu Met Ser
                 85                  90                  95
Arg Thr Asp Ser Lys Ser Gly Lys Asn Arg Ser Gly Val Arg Met Phe
                100                 105                 110
Lys Asp Gly Asp Phe Leu Thr Pro Ala Ser Gly Glu Ser Trp Asp Arg
                115                 120                 125
Leu Arg Leu Thr Cys Ser Gln Pro Phe Thr Arg His Gln Ser Phe Gly
130                 135                 140
Leu Ala Phe Leu Arg Val Arg Ser Ser Leu Gly Ser Leu Ala Asp Pro
145                 150                 155                 160
Val Val Asp Pro Ser Ala Pro Gly Ser Ser Gly Leu Asn Gln Asn Ser
                165                 170                 175
Thr Asp Val Leu Glu Ser Asp Pro Arg Pro Trp Leu Thr Asn Pro Ser
                180                 185                 190
Ile Arg Arg Thr Phe Phe Pro Asp Pro Gln Thr Ser Thr Lys Glu Ile
                195                 200                 205
Ser Glu Leu Lys Gly Met Leu Lys Gln Leu Gln Pro Gly Pro Leu Gly
                210                 215                 220
Arg Ala Ala Arg Met Val Leu Ser Ala Ala Arg Lys Ala Pro Pro Ala
225                 230                 235                 240
Ser Val Val Ser Pro Asn Asn Ser His Gly Glu Pro Gly Pro Ser Arg
                245                 250                 255
Ala Glu Ser Ala Glu Pro Arg Ala Glu Glu Pro Asn Arg Lys Thr Ala
                260                 265                 270
Val Gly Arg Arg Lys Arg Arg Lys Val Gln Glu Pro Arg Arg Ser Leu
                275                 280                 285
Ser Asn Ser Ser Ser Gln Pro Asn Arg Arg Thr Gly Arg Thr Arg Gln
290                 295                 300
Arg Gln His Arg Pro Gln Thr Lys Ser Asp Asp Gly Gly Val Gln Ala
305                 310                 315                 320
Ala Gly Gln Cys Pro Ile Cys Ala Gly Phe Phe Ser Ile Glu Thr Leu
                325                 330                 335
Pro Gln His Ala Ala Thr Cys Gly Glu Ser Pro Pro Gln Pro Ala
                340                 345                 350
Ser Pro Ala Ser Leu Ser Ser Glu Ser Val Leu Arg Arg His His
                355                 360                 365
Val Ala Leu Thr Pro Val Pro Leu Val Pro Lys Pro Gln Pro Asn Trp
370                 375                 380
Thr Glu Ile Val Asn Lys Lys Leu Lys Phe Pro Pro Thr Leu Leu Arg
385                 390                 395                 400
Ala Ile Gln Glu Gly Gln Leu Gly Leu Val Gln Gln Leu Leu Glu Ser
                405                 410                 415
Ser Ser Asp Ala Ser Gly Ala Gly Pro Gly Gly Pro Leu Arg Asn Val
                420                 425                 430
Glu Glu Ser Glu Asp Arg Ser Trp Arg Glu Ala Leu Asn Leu Ala Ile
                435                 440                 445
Arg Leu Gly His Glu Val Ile Thr Asp Val Leu Leu Ala Asn Val Lys
```

```
              450                 455                 460
Phe Asp Phe Arg Gln Ile His Glu Ala Leu Leu Val Ala Val Asp Thr
465                 470                 475                 480

Asn Gln Pro Ala Val Arg Arg Leu Leu Ala Arg Leu Glu Arg Glu
                485                 490                 495

Lys Gly Arg Lys Val Asp Thr Lys Ser Phe Ser Leu Ala Phe Phe Asp
                500                 505                 510

Ser Ser Ile Asp Gly Ser Arg Phe Ala Pro Gly Val Thr Pro Leu Thr
            515                 520                 525

Leu Ala Cys Gln Lys Asp Leu Tyr Glu Ile Ala Gln Leu Leu Met Asp
530                 535                 540

Gln Gly His Thr Ile Ala Arg Pro His Pro Val Ser Cys Ala Cys Leu
545                 550                 555                 560

Glu Cys Ser Asn Ala Arg Arg Tyr Asp Leu Leu Lys Phe Ser Leu Ser
                565                 570                 575

Arg Ile Asn Thr Tyr Arg Gly Ile Ala Ser Arg Ala His Leu Ser Leu
                580                 585                 590

Ala Ser Glu Asp Ala Met Leu Ala Ala Phe Gln Leu Ser Arg Glu Leu
            595                 600                 605

Arg Arg Leu Ala Arg Lys Glu Pro Glu Phe Lys Pro Gln Tyr Ile Ala
610                 615                 620

Leu Glu Ser Leu Cys Gln Asp Tyr Gly Phe Glu Leu Leu Gly Met Cys
625                 630                 635                 640

Arg Asn Gln Ser Glu Val Thr Ala Val Leu Asn Asp Leu Gly Glu Asp
                645                 650                 655

Ser Glu Thr Glu Pro Glu Ala Glu Gly Leu Gly Gln Ala Phe Glu Glu
                660                 665                 670

Gly Ile Pro Asn Leu Ala Arg Leu Arg Leu Ala Val Asn Tyr Asn Gln
            675                 680                 685

Lys Gln Phe Val Ala His Pro Ile Cys Gln Gln Val Leu Ser Ser Ile
            690                 695                 700

Trp Cys Gly Asn Leu Ala Gly Trp Arg Gly Ser Thr Thr Ile Trp Arg
705                 710                 715                 720

Leu Phe Val Ala Ser Leu Ile Phe Leu Thr Met Pro Phe Leu Cys Ile
                725                 730                 735

Gly Tyr Trp Leu Ala Pro Lys Ser Gln Leu Gly Arg Leu Leu Lys Ile
                740                 745                 750

Pro Val Leu Lys Phe Leu Leu His Ser Ala Ser Tyr Leu Trp Phe Leu
                755                 760                 765

Ile Phe Leu Leu Gly Glu Ser Leu Val Met Glu Thr Gln Leu Ser Thr
770                 775                 780

Phe Lys Gly Arg Ser Gln Ser Val Trp Glu Thr Ser Leu His Met Ile
785                 790                 795                 800

Trp Val Thr Gly Phe Leu Trp Phe Glu Cys Lys Glu Val Trp Ile Glu
                805                 810                 815

Gly Leu Arg Ser Tyr Leu Leu Asp Trp Trp Asn Phe Leu Asp Val Val
                820                 825                 830

Ile Leu Ser Leu Tyr Leu Ala Ser Phe Ala Leu Arg Leu Leu Leu Ala
                835                 840                 845

Gly Leu Ala Tyr Met His Cys Arg Asp Ala Ser Asp Ser Thr Thr Cys
850                 855                 860

Arg Cys Phe Thr Thr Ala Glu Arg Ser Glu Trp Arg Thr Glu Asp Pro
865                 870                 875                 880
```

```
Gln Phe Leu Ala Glu Val Leu Phe Thr Val Thr Ser Met Leu Ser Phe
                885                 890                 895

Thr Arg Leu Ala Tyr Ile Leu Pro Ala His Glu Ser Leu Gly Thr Leu
            900                 905                 910

Gln Ile Ser Ile Gly Lys Met Ile Asp Asp Met Ile Arg Phe Met Phe
            915                 920                 925

Ile Leu Met Ile Ile Leu Thr Ala Phe Leu Cys Gly Leu Asn Asn Ile
            930                 935                 940

Tyr Val Pro Tyr Gln Glu Ser Glu Lys Leu Gly Asn Phe Asn Glu Thr
945                 950                 955                 960

Phe Gln Phe Leu Phe Trp Thr Met Phe Gly Met Glu Glu His Thr Val
                965                 970                 975

Val Asp Met Pro Gln Phe Leu Val Pro Glu Phe Val Gly Arg Ala Met
                980                 985                 990

Tyr Gly Ile Phe Thr Ile Val Met Val Ile Val Leu Leu Asn Met Leu
                995                 1000                1005

Ile Ala Met Ile Thr Asn Ser Phe Gln Lys Ile Glu Asp Asp Ala Asp
    1010                1015                1020

Val Glu Trp Lys Phe Ala Arg Ser Lys Leu Tyr Leu Ser Tyr Phe Arg
1025                1030                1035                1040

Glu Gly Leu Thr Leu Pro Val Pro Phe Asn Ile Leu Pro Ser Pro Lys
                1045                1050                1055

Ala Ala Phe Tyr Leu Val Arg Arg Ile Phe Arg Phe Leu Cys Cys Gly
                1060                1065                1070

Ser Ser Cys Cys Lys Ala Lys Lys Ser Asp Tyr Pro Pro Ile Gly Thr
                1075                1080                1085

Phe Thr Asn Pro Gly Ala Arg Ala Gly Ser Ala Gly Glu Gly Glu Arg
                1090                1095                1100

Val Ser Tyr Arg Leu Arg Val Ile Lys Ala Leu Val Gln Arg Tyr Ile
1105                1110                1115                1120

Glu Thr Ala Arg Arg Glu Phe Glu Glu Thr Arg Arg Lys Asp Leu Gly
                1125                1130                1135

Asn Arg Leu Thr Glu Leu Thr Lys Thr Val Ser Arg Leu Gln Ser Glu
                1140                1145                1150

Val Ala Ser Val Gln Lys Asn Leu Ala Ala Gly Gly Ala Pro Arg Pro
                1155                1160                1165

Pro Asp Gly Ala Ser Ile Leu Ser Arg Tyr Ile Thr Arg Val Arg Asn
    1170                1175                1180

Ser Phe Gln Asn Leu Gly Pro Pro Thr Ser Asp Thr Pro Ala Glu Leu
1185                1190                1195                1200

Thr Met Pro Gly Ile Val Glu Thr Glu Val Ser Leu Gly Asp Gly Leu
                1205                1210                1215

Asp Gly Thr Gly Glu Ala Gly Pro Ala Pro Gly Glu Pro Gly Ser
                1220                1225                1230

Ser Ser Ser Ala His Val Leu Val His Arg Glu Gln Glu Ala Glu Gly
                1235                1240                1245

Ser Gly Asp Leu Leu Leu Glu Gly Asp Leu Glu Thr Lys Gly Glu Ser
                1250                1255                1260

<210> SEQ ID NO 31
<211> LENGTH: 705
<212> TYPE: DNA
<213> ORGANISM: Homo sapiens
```

<400> SEQUENCE: 31

```
atggctcctg tgaagatcag ccatgtggta tcattttctt ctcaggatcc caagtatcct       60
gtagagaact tgctaaaccc agatagtcca aggagacctt ggctcggctg ccctcaggac      120
aagagtgggc aattgaaagt agaactacag ctggagaggg cagtgccac tggctacatt      180
gatgtgggta actgtggctg tgcgttcctg caaattgatg tgggccattc ttcctggccc      240
ctggacagac ctttcataac cctgctccct gcaaccacgc taatgtctct aactgattca      300
aagcagggga agaaccgctc cggggtccgc atgtttaaag atgttgattt cctggctcca      360
gcctcaggag agttatggga tcgacttcgc ctgacctgct cccgacccct tacgcgtcat      420
cagtcctttg gcctggcctt tctacgggtg tgttcttctc tggactcctt agatgactct      480
gtggtgggtc cctcagccct tctgagctct gtgctgaaca agataagaga gtttaagaca      540
tgttttttct cctggagtct gaagaagatg gagttagaat tttcaccact tcttttgtcc      600
atcaatttga atgatcttca gtttgcagca gatgctgaag tcagcacagt atctaattgc      660
atgttcatca gcattgcact tcagtctgca atgataatat tctga                     705
```

<210> SEQ ID NO 32
<211> LENGTH: 234
<212> TYPE: PRT
<213> ORGANISM: Homo sapiens

<400> SEQUENCE: 32

```
Met Ala Pro Val Lys Ile Ser His Val Val Ser Phe Ser Ser Gln Asp
  1               5                  10                  15

Pro Lys Tyr Pro Val Glu Asn Leu Leu Asn Pro Asp Ser Pro Arg Arg
             20                  25                  30

Pro Trp Leu Gly Cys Pro Gln Asp Lys Ser Gly Gln Leu Lys Val Glu
         35                  40                  45

Leu Gln Leu Glu Arg Ala Val Pro Thr Gly Tyr Ile Asp Val Gly Asn
     50                  55                  60

Cys Gly Cys Ala Phe Leu Gln Ile Asp Val Gly His Ser Ser Trp Pro
 65                  70                  75                  80

Leu Asp Arg Pro Phe Ile Thr Leu Leu Pro Ala Thr Thr Leu Met Ser
                 85                  90                  95

Leu Thr Asp Ser Lys Gln Gly Lys Asn Arg Ser Gly Val Arg Met Phe
            100                 105                 110

Lys Asp Val Asp Phe Leu Ala Pro Ala Ser Gly Glu Leu Trp Asp Arg
        115                 120                 125

Leu Arg Leu Thr Cys Ser Arg Pro Phe Thr Arg His Gln Ser Phe Gly
    130                 135                 140

Leu Ala Phe Leu Arg Val Cys Ser Ser Leu Asp Ser Leu Asp Asp Ser
145                 150                 155                 160

Val Val Gly Pro Ser Ala Leu Leu Ser Ser Val Leu Asn Lys Ile Arg
                165                 170                 175

Glu Phe Lys Thr Cys Phe Phe Ser Trp Ser Leu Lys Lys Met Glu Leu
            180                 185                 190

Glu Phe Ser Pro Leu Leu Leu Ser Ile Asn Leu Asn Asp Leu Gln Phe
        195                 200                 205

Ala Ala Asp Ala Glu Val Ser Thr Val Ser Asn Cys Met Phe Ile Ser
    210                 215                 220

Ile Ala Leu Gln Ser Ala Met Ile Ile Phe
225                 230
```

<210> SEQ ID NO 33
<211> LENGTH: 1218
<212> TYPE: DNA
<213> ORGANISM: Mus musculus

<400> SEQUENCE: 33

| | | | | | |
|---|---|---|---|---|---|
| atggctcctg | tgaagatcag | ccatgtggtg | tcatttttcct | ctcaggatcc | caaatatcct | 60 |
| gtggagaact | tgctgaaccc | agacagtcac | aggggaccct | ggctcagctg | ccctcaggac | 120 |
| aagactggac | aactgaaagt | ggagtttcag | ctggagaggg | cagtgcccat | aagctatatt | 180 |
| gatgttggaa | actgtggctg | tgcttttccta | cagattgatg | tgggtcgttc | ttcctggccc | 240 |
| ctggacagac | ctttcgtcac | cctgctccct | gccaccatgc | taatgtcccg | cactgactcc | 300 |
| aagtcgggga | gaaccgctc | aggggtccgg | atgtttaaag | atggtgattt | cctgactcca | 360 |
| gcctcaggag | agtcctggga | tcgacttcga | ttgacctgct | ccaaccttt | cacacgtcat | 420 |
| cagtcctttg | gcctggcctt | cctacgagtg | cgttcctctc | tgggctctct | ggctgaccct | 480 |
| gtagtagatc | cctcagcccc | tgggagctct | gggcttaacc | agaactctac | agatgtgctg | 540 |
| gagtctgatc | ctaggccctg | gctgactaat | ccttctatcc | ggaggacatt | cttccccgat | 600 |
| ccccagacga | gcaccaagga | aatttcagag | ctcaagggta | tgttgaagca | gttgcagcca | 660 |
| gggcctctgg | ggcgggcagc | ccgcatggtg | ctttctgctg | cccgtaaggc | ccctccagcc | 720 |
| agtgtggtaa | gcccaaacaa | cagccacgga | gaaccaggtc | ccagccgtgc | agagagtgca | 780 |
| gagcccagag | cagaagaacc | aaacaggaag | acggctgtgg | gcagaaggaa | gaggaggaaa | 840 |
| gtgcaggagc | caaggagatc | gttgtccaac | tcgagttctc | agccaaatag | gaggacagga | 900 |
| aggacaagac | aaagacagca | ccgacctcag | accaaaagtg | atgacggtgg | tgtgcaggct | 960 |
| gctggacagt | gtcctatttg | tgcaggtttc | ttcagtattg | agactcttcc | ccagcatgct | 1020 |
| gcaacttgtg | gagagagccc | cccaccccag | ccagcttctc | ctgcctcctt | gtcttcctcg | 1080 |
| gagtccgtgc | tgtgggtctc | ctccccagag | agctcgccgc | caccttcctg | ggtccagtgc | 1140 |
| cctatctgtg | aattacagtt | ctcagcaaga | gaaatagaag | aacatgccag | cgtgtgtggg | 1200 |
| gaagttttgc | cagcctga | | | | | 1218 |

<210> SEQ ID NO 34
<211> LENGTH: 405
<212> TYPE: PRT
<213> ORGANISM: Mus musculus

<400> SEQUENCE: 34

Met Ala Pro Val Lys Ile Ser His Val Val Ser Phe Ser Ser Gln Asp
 1               5                  10                  15

Pro Lys Tyr Pro Val Glu Asn Leu Leu Asn Pro Asp Ser His Arg Gly
             20                  25                  30

Pro Trp Leu Ser Cys Pro Gln Asp Lys Thr Gly Gln Leu Lys Val Glu
         35                  40                  45

Phe Gln Leu Glu Arg Ala Val Pro Ile Ser Tyr Ile Asp Val Gly Asn
     50                  55                  60

Cys Gly Cys Ala Phe Leu Gln Ile Asp Val Gly Arg Ser Ser Trp Pro
 65                  70                  75                  80

Leu Asp Arg Pro Phe Val Thr Leu Leu Pro Ala Thr Met Leu Met Ser
                 85                  90                  95

Arg Thr Asp Ser Lys Ser Gly Lys Asn Arg Ser Gly Val Arg Met Phe
            100                 105                 110

```
Lys Asp Gly Asp Phe Leu Thr Pro Ala Ser Gly Glu Ser Trp Asp Arg
        115                 120                 125

Leu Arg Leu Thr Cys Ser Gln Pro Phe Thr Arg His Gln Ser Phe Gly
        130                 135                 140

Leu Ala Phe Leu Arg Val Arg Ser Ser Leu Gly Ser Leu Ala Asp Pro
145                 150                 155                 160

Val Val Asp Pro Ser Ala Pro Gly Ser Ser Gly Leu Asn Gln Asn Ser
                165                 170                 175

Thr Asp Val Leu Glu Ser Asp Pro Arg Pro Trp Leu Thr Asn Pro Ser
                180                 185                 190

Ile Arg Arg Thr Phe Phe Pro Asp Pro Gln Thr Ser Thr Lys Glu Ile
        195                 200                 205

Ser Glu Leu Lys Gly Met Leu Lys Gln Leu Gln Pro Gly Pro Leu Gly
        210                 215                 220

Arg Ala Ala Arg Met Val Leu Ser Ala Ala Arg Lys Ala Pro Pro Ala
225                 230                 235                 240

Ser Val Val Ser Pro Asn Asn Ser His Gly Glu Pro Gly Pro Ser Arg
                245                 250                 255

Ala Glu Ser Ala Glu Pro Arg Ala Glu Glu Pro Asn Arg Lys Thr Ala
                260                 265                 270

Val Gly Arg Arg Lys Arg Arg Lys Val Gln Glu Pro Arg Arg Ser Leu
        275                 280                 285

Ser Asn Ser Ser Ser Gln Pro Asn Arg Arg Thr Gly Arg Thr Arg Gln
        290                 295                 300

Arg Gln His Arg Pro Gln Thr Lys Ser Asp Asp Gly Gly Val Gln Ala
305                 310                 315                 320

Ala Gly Gln Cys Pro Ile Cys Ala Gly Phe Phe Ser Ile Glu Thr Leu
                325                 330                 335

Pro Gln His Ala Ala Thr Cys Gly Glu Ser Pro Pro Gln Pro Ala
                340                 345                 350

Ser Pro Ala Ser Leu Ser Ser Ser Glu Ser Val Leu Trp Val Ser Ser
        355                 360                 365

Pro Glu Ser Ser Pro Pro Ser Trp Ser Gln Cys Pro Ile Cys Glu
        370                 375                 380

Leu Gln Phe Ser Ala Arg Glu Ile Glu Glu His Ala Ser Val Cys Gly
385                 390                 395                 400

Glu Val Leu Pro Ala
                405

<210> SEQ ID NO 35
<211> LENGTH: 234
<212> TYPE: PRT
<213> ORGANISM: Homo sapiens

<400> SEQUENCE: 35

Met Ala Pro Val Lys Ile Ser His Val Val Ser Phe Ser Ser Gln Asp
1               5                   10                  15

Pro Lys Tyr Pro Val Glu Asn Leu Leu Asn Pro Asp Ser His Arg Arg
            20                  25                  30

Pro Trp Leu Gly Cys Pro Gln Asp Lys Ser Gly Gln Leu Lys Val Glu
        35                  40                  45

Leu Gln Leu Glu Arg Ala Val Pro Thr Gly Tyr Ile Asp Val Gly Asn
    50                  55                  60

Cys Gly Cys Ala Phe Leu Gln Ile Asp Val Gly His Ser Ser Trp Pro
65                  70                  75                  80
```

```
Leu Asp Arg Pro Phe Ile Thr Leu Pro Ala Thr Thr Leu Met Ser
                85                  90                  95

Leu Thr Asp Ser Lys Gln Gly Lys Asn Arg Ser Gly Val Arg Met Phe
            100                 105                 110

Lys Asp Val Asp Phe Leu Ala Pro Ala Ser Gly Glu Leu Trp Asp Arg
        115                 120                 125

Leu Arg Leu Thr Cys Ser Arg Pro Phe Thr Arg His Gln Ser Phe Gly
    130                 135                 140

Leu Ala Phe Leu Arg Val Cys Ser Ser Leu Asp Ser Leu Asp Asp Ser
145                 150                 155                 160

Val Val Gly Pro Ser Ala Leu Leu Ser Val Leu Asn Lys Ile Arg
                165                 170                 175

Glu Phe Lys Thr Cys Phe Phe Ser Trp Ser Leu Lys Lys Met Glu Leu
            180                 185                 190

Glu Phe Ser Pro Leu Leu Ser Ile Asn Leu Asn Asp Leu Gln Phe
        195                 200                 205

Ala Ala Asp Ala Glu Val Ser Thr Val Ser Asn Cys Met Phe Ile Ser
    210                 215                 220

Ile Ala Leu Gln Ser Ala Met Ile Ile Phe
225                 230

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
cgtccgatgg ctcctgtgaa                                          20

<210> SEQ ID NO 37
<211> LENGTH: 18
<212> TYPE: DNA
<213> ORGANISM: Artificial Sequence
<220> FEATURE:
<223> OTHER INFORMATION: Primer

<400> SEQUENCE: 37
ggctggcaaa acttcccc                                            18

<210> SEQ ID NO 38
<211> LENGTH: 42
<212> TYPE: PRT
<213> ORGANISM: Artificial Sequence
<220> FEATURE:
<223> OTHER INFORMATION: Synthetically generated peptide

<400> SEQUENCE: 38

Arg Gln Ile Lys Ile Trp Phe Gln Asn Arg Arg Met Lys Trp Lys Lys
1               5                   10                  15

Leu Leu Pro Gln His Ala Ala Thr Cys Gly Glu Ser Pro Pro Gln
            20                  25                  30

Pro Ala Ser Pro Ala Ser Leu Ser Ser Ser
        35                  40

<210> SEQ ID NO 39
<211> LENGTH: 41
<212> TYPE: PRT
<213> ORGANISM: Artificial Sequence
```

-continued

```
<220> FEATURE:
<223> OTHER INFORMATION: Synthetically generated peptide

<400> SEQUENCE: 39

Arg Gln Ile Lys Ile Trp Phe Gln Asn Arg Arg Met Lys Trp Lys Lys
 1               5                  10                  15

Leu Pro Gln His Ala Ala Thr Cys Gly Glu Thr Ser Pro Pro His Pro
            20                  25                  30

Ala Ser Pro Ser Ser Ser Ser Ser
            35              40
```

US 6,991,909 B2

ENKURIN AND USES THEREOF

CROSS REFERENCE TO RELATED APPLICATION

Pursuant to 35 USC §119 (e), this application claims the benefit of prior U.S. provisional application No. 60/359,870 filed on Feb. 25, 2002, the contents of which is incorporated herein by reference in its entirety.

FEDERALLY SPONSORED RESEARCH OR DEVELOPMENT

This invention was made with Government support under grant number HD40310 awarded by the National Institutes of Health. The Government has certain rights in the invention.

TECHNICAL FIELD

This invention relates to calcium channel function, for example, in the field of contraception.

BACKGROUND

The sperm acrosome reaction (AR) is a $Ca^{2+}$-dependent exocytotic event that occurs during the early stages of fertilization in many animal species, including humans and all other mammals. One model of the signal transduction mechanisms linking ZP3 stimulation to sustained intracellular calcium ($Ca^{2+}{}_i$) responses suggests that ZP3 activates two primary signal transducers. First phospholipase C (PLC) activity is stimulated and generates inositol trisphosphate (IP3), leading to activation of IP3-gated $Ca^{2+}$ release channels in the acrosome. There is also activation of a T-type voltage-sensitive $Ca^{2+}$ channel that produces a transient $Ca^{2+}$ influx during the first second of ZP3 signaling. The pivotal role of the AR is indicated by the observation that fertilization fails when exocytosis occurs either prematurely or is inhibited. The TRPC2 (Transient Receptor Potential Classic 2) gene encodes a subunit of a sperm $Ca^{2+}$ channel; that ZP3, the AR-inducing agonist of the egg's extracellular zona pellucida matrix (henceforth zona) activates the TRPC2 channel to trigger a sustained $Ca^{2+}$ entry into sperm; and that it is this $Ca^{2+}$ entry that drives the AR (Jungnickel et al., 2001, Nature Cell Biol. 3:499–502). However, TRPC2 is believed to be a pseudogene in humans.

TRPCs have been implicated to be involved as an ion channel in signal transduction in cell proliferation, activation, immune response, and secretion.

SUMMARY

The invention is based in part on the discovery of a novel TRPC-binding protein, enkurin, which is specifically expressed in human and mouse testis. As a TRPC-binding protein and thus part of the ZP3 signaling pathway, enkurin is a target for contraceptive intervention. Because enkurin is involved in ZP3 signaling, agents that disrupt or trigger enkurin binding, activity, or expression can be used in male or female animals (e.g., mammals, including humans) for regulation of the reproductive system, for example, as a contraceptive agent. 5' extended TRPC2 and a novel TRPC2 transcript, TRPC2-S, and splice variants thereof have also been discovered. TRPC2-S is a non-channel transcript that is expressed in the male germ lineage and can interact with enkurin. Enkurin can also bind other TRPC proteins (e.g., TRPC2-S). Enkurin and TRPC (e.g., TRPC2-S) are part of a newly identified signal transduction mechanism that has components involved in fertilization, thus providing new targets for discovering novel contraceptives and treatments for fertility. Also discovered is a 5' extended form of TRPC2 which extends approximately 92 amino acids upstream from the currently published start site of unspliced TRPC2 (Gene bank Accession no, A111108).

In general, the invention features a method of identifying a candidate compound that modulates the expression or activity of an enkurin polypeptide by (a) obtaining a test sample comprising a cell that can express an enkurin polypeptide (e.g., a cell that contains an exogenous enkurin nucleic acid sequence); (b) contacting the test sample with a test compound; and (c) determining a level of expression or activity of the enkurin polypeptide in the test sample of (b); wherein a level of expression or activity in the test sample contacted with the test compound that is different from a predetermined value indicates that the test compound is a candidate compound for modulating enkurin expression or activity. For example, enkurin expression or activity can be decreased or increased, and the level of enkurin expression or activity can be determined by exposing the test sample to a compound that binds to the enkurin polypeptide, e.g., an antibody, and detecting levels of the compound.

In these methods, the enkurin polypeptide can comprise the sequence of SEQ ID NO:1 or 2. The enkurin nucleic acid sequence can comprise the sequence of SEQ ID NO:12 or 20.

In certain embodiments, the method can further include (d) assaying $Ca^{2+}$ influx in the presence of the test compound; and (e) determining the amount of $Ca^{2+}$ influx in the presence of the test compound compared to a reference compound such that a difference in the amount of $Ca^{2+}$ influx indicates that the test compound is a candidate compound for modulating enkurin expression or activity.

The invention also includes methods of diagnosing a disorder associated with aberrant expression of an enkurin polypeptide, such as infertility, by measuring enkurin polypeptide expression in a biological sample, e.g., sperm, wherein increased or decreased enkurin polypeptide expression in the biological sample compared to a control indicates a disorder associated with aberrant expression of an enkurin polypeptide. In other embodiments, the invention also includes methods of inhibiting fertility by administering to a subject in need thereof an effective amount of a compound that decreases enkurin activity, such as an antibody, an antibody fragment, or an antibody fusion that binds to an enkurin polypeptide. For example, the antibody can bind to the TRPC binding domain of enkurin.

In another aspect, the invention features a method of increasing fertility by administering to a male subject in need thereof, an effective amount of enkurin polypeptide, and a method for detecting an enkurin polypeptide in a biological sample by (a) contacting the biological sample with an antibody that specifically binds to an enkurin polypeptide (e.g., a polyclonal antibody, a monoclonal antibody, or a recombinant antibody) under conditions that allow the formation of an enkurin polypeptide-antibody complex; and (b) detecting any antibody-polypeptide complexes; wherein the presence of a complex indicates the presence of an enkurin polypeptide in the sample, such as a sperm sample.

In other aspects, the invention includes pharmaceutical compositions that include an enkurin-modulating compound, e.g., one that disrupts enkurin interaction with a TRPC. For example, the enkurin interaction with a TRPC consists of binding to a TRPC, e.g., a TRPC2 polypeptide, or a TRPC2-S polypeptide.

In another embodiment, the invention includes isolated nucleic acid molecules, the nucleotide sequence of which consist of SEQ ID NO:12, or a complement thereof, a nucleotide sequence of at least 10 consecutive nucleotides of SEQ ID NO:12 or a complement thereof, and isolated nucleic acid molecules including a nucleotide sequence that encodes a polypeptide comprising the amino acid sequence of SEQ ID NO:1 or 2, or of a fragment of SEQ ID NO:1 or 2, wherein the polypeptide binds to a TRPC polypeptide. The invention also includes vectors, e.g., expression vectors, that include the nucleotide sequence of SEQ ID NO:12, 20, 21, 23, 25, 27, 29, 31, 33, or 38, or a complement thereof, e.g., operably linked to an expression control sequence.

The invention also includes cultured cells including the new vectors, e.g., operably linked to an expression control sequence.

In another aspect, the invention includes isolated polypeptides encoded by the nucleotide sequence of SEQ ID NO:12 or 20, and isolated polypeptides consisting of the sequence of SEQ ID NO:1 or 2, or a fragment of at least 10 consecutive amino acids of SEQ ID NO:1 or 2.

In yet another aspect, the invention includes antisense oligonucleotides that inhibit expression of (i) an enkurin protein encoded by SEQ ID NO:12 or 20, or a fragment thererof, (ii) a protein comprising the sequence of SEQ ID NO:1 or 2 or a fragment thererof, or (iii) a nucleic acid sequence encoding the amino acid sequence of SEQ ID NO:9 or 10, or a fragment thereof.

The invention also covers purified antibodies that bind specifically to the polypeptide having the amino acid sequence of SEQ ID NO:1 or 2, or a biologically functional fragment thereof, e.g., monoclonal, polyclonal, or recombinant antibodies.

The invention also includes isolated nucleic acids that include a sequence that encodes a polypeptide comprising the amino acid sequence of SEQ ID NO:22, 24, 30, 26, 28, 32, 38, or of a biologically functional fragment thereof, e.g., that binds to enkurin polypeptide.

In other aspects, the invention features isolated nucleic acid molecules that include a nucleotide sequence of SEQ ID NO:21 or 33 a complement thereof, or a nucleotide sequence of at least 10 consecutive nucleotides of SEQ ID NO:21 or 33 or a complement thereof, and vectors and cultured cells that include these molecules.

The invention also includes isolated polypeptides encoded by the nucleotide sequence of SEQ ID NO:21 or 33, isolated polypeptides consisting of the sequence of SEQ ID NO:22, 24, 26, 28, 30, or 32, or a biologically functional fragment thereof, and antisense oligonucleotides that inhibit expression of 5' extended TRPC2 protein encoded by SEQ ID NO:29, 30, 38, or 39, or biologically functional fragment thereof. The invention also includes antisense oligonucleotides that inhibit expression of a protein comprising the sequence of SEQ ID NO:22, 24, 26, 28, 30, or 32, and purified antibodies that bind specifically to a polypeptide having the amino acid sequence of SEQ ID NO:22, 24, 26, 28, 30, or 32 or a functional fragment thereof.

In another aspect, the invention features a method of modulating an acrosome reaction (AR) of a sperm by contacting the sperm with a compound that modulates the expression or activity of an enkurin polypeptide or a TRPC2-S polypeptide in an amount sufficient to inhibit or to activate the AR. For example, the acrosome reaction can be stimulated, thereby promoting fertilization. The method can be applied to in vitro fertilization or artificial insemination. In certain embodiments, the compound is administered vaginally to a female subject, or systemically or locally to a male subject for promoting fertilization.

In another aspect, the invention features a method of inhibiting the acrosome reaction by contacting a sperm with an effective amount of a compound that modulates the expression or activity of an enkurin, 5' extended TRPC2 or splice variant thereof, or TRPC2-S or splice variant thereof. For example, the compound can include or have the sequence of SEQ ID NO:38. Again, the compound can be administered vaginally to a female subject, or systemically or locally to a male subject for blocking fertilization.

The invention also includes a method of identifying a candidate compound that modulates the expression or activity of a 5' extended TRPC2 polypeptide or splice variant thereof by (a) obtaining a test sample comprising a cell that can express a 5' extended TRPC2 polypeptide or a polypeptide of a splice variant thereof; (b) contacting the test sample with a test compound; and (c) determining a level of expression or activity of the 5' extended TRPC2 polypeptide or the polypeptide of a splice variant thereof in the test sample of (b); wherein a level of expression or activity in the test sample contacted with the test compound different from a predetermined value indicates that the test compound is a candidate compound for modulating 5' extended TRPC2 polypeptide or splice variant thereof. In this method, expression or activity can be decreased or increased.

In certain embodiments, the level of 5' extended TRPC2 or 5' extended TRPC2 splice variant expression or activity can be determined by exposing the test sample to a compound (e.g., an antibody) that binds to the 5' extended TRPC2 polypeptide or 5' extended TRPC2 splice variant polypeptide and detecting levels of the compound. The 5' extended TRPC2 polypeptide or 5' extended TRPC2 splice variant polypeptide can include or have the sequence of SEQ ID NO:22, 24, 26, 28, 30, or 32. The 5' extended TRPC2 nucleic acid or 5' extended TRPC2 splice variant nucleic acid sequence can have or include SEQ ID NO:29 or 31. The cell can include an exogenous 5' extended TRPC2 nucleic acid sequence or 5' extended TRPC2 splice variant nucleic acid sequence.

The method can further include (d) assaying $Ca^{2+}$ influx in the presence of the test compound; and (e) determining the amount of $Ca^{2+}$ influx in the presence of the test compound compared to a reference compound such that a difference in the amount of $Ca^{2+}$ influx indicates that the test compound is a candidate compound for modulating 5' extended TRPC2 or 5' extended TRPC2 splice variant expression or activity.

The term "nucleic acid molecule" includes DNA molecules (e.g., a cDNA) and RNA molecules (e.g., an mRNA) and analogs of the DNA or RNA generated, e.g., by the use of nucleotide analogs. The nucleic acid molecule can be single-stranded or double-stranded, but generally is double-stranded DNA.

The term "isolated or purified nucleic acid molecule" includes nucleic acid molecules that are separated from other nucleic acid molecules which are present in the natural source of the nucleic acid. For example, with regards to genomic DNA, the term "isolated" includes nucleic acid molecules that are separated from the chromosome with which the genomic DNA is naturally associated. In general, an "isolated" nucleic acid is free of sequences that naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

The term "hybridizes under stringent conditions" describes conditions for hybridization and washing. Stringent conditions are known to those skilled in the art and can be found in *Current Protocols in Molecular Biology*, John Wiley & Sons, N.Y. (1989), 6.3.1–6.3.6. Aqueous and non-aqueous methods are described in that reference and either can be used. Example of hybridization and washing conditions are hybridization in 6× sodium chloride/sodium citrate (SSC) at about 45° C., followed by one or more washes in 0.2×SSC, 0.1% SDS at 50° C. (low stringency), 55° C. (moderate stringency), or 60° C. (high stringency), depending on the level of stringency required. In general, an isolated nucleic acid molecule of the invention that hybridizes under stringent conditions to the sequence of an enkurin cDNA or a TRPC (e.g., TRPC2) cDNA, corresponds to a naturally-occurring nucleic acid molecule.

"Naturally-occurring" nucleic acid molecules are RNA or DNA molecules having a nucleotide sequence that occurs in nature (e.g., encodes a natural protein).

A "polypeptide" is any chain of amino acids, regardless of length, and thus includes polypeptides, proteins, and peptides.

A "peptidomimetic" is a chemical variant of a polypeptide (e.g., a peptide) in which the side chains of the polypeptide are substantially maintained in the variant, yet the chemical backbone of the peptidomimetic is altered relative to the polypeptide in at least one peptide bond.

A "peptoid" is an oligomer of N-substituted glycines. A peptoid can be synthesized from a variety of different N-alkylglycines that have side chains similar to amino acid side chains, e.g., as described in Simon et al., 1992, Proc. Natl. Acad. Sci. USA 89:9367–9371. As an alternative to natural polymers, peptoids provide a modular system that allows one to synthesize monomers in large amounts. The monomers have a wide variety of functional groups presented as side chains off of an oligomeric backbone, the linking chemistry is high yielding and amenable to automation. The linkage in a peptoid is resistant to hydrolytic enzymes such as proteases. Another advantage is that the monomers are achiral.

A "substantially pure" preparation is at least 60% by weight (dry weight) the compound of interest, i.e., an enkurin polypeptide. Thus, a substantially pure enkurin polypeptide is not mixed or otherwise associated with proteins. A preparation of a substantially pure enkurin polypeptide is also substantially free of an antibody or any other compound that binds to an enkurin polypeptide. In general, the preparation is at least 75%, at least 90%, or at least 99%, by weight of the enkurin polypeptide. Purity can be measured by any appropriate standard method, e.g., column chromatography, polyacrylamide gel electrophoresis, MALDI-TOF mass spectrometry (MS), or HPLC analysis.

In the case of polypeptide sequences that are less than 100% identical to a reference sequence (for example, a wild-type sequence), the non-identical positions can be conservative substitutions for the reference sequence or substitutions of non-essential amino acids.

A "non-essential" amino acid residue is a residue that can be altered from the wild-type sequence of an enkurin (e.g., the sequence of SEQ ID NO:1 or 2) without abolishing or substantially altering a biological activity, whereas an "essential" amino acid residue results in such a change.

A "conservative amino acid substitution" is one in which the amino acid residue is replaced with an amino acid residue having a similar side chain. Families of amino acid residues having similar side chains have been defined. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in an enkurin protein is replaced with another amino acid residue from the same side chain family. Alternatively, in another embodiment, mutations can be introduced randomly along all or part of an enkurin coding sequence, such as by saturation mutagenesis, and the resultant mutants can be screened for enkurin biological activity to identify mutants that retain activity.

A "biologically active portion" of an enkurin protein includes a fragment of an enkurin protein that participates in an interaction between an enkurin molecule and a non-enkurin molecule (e.g., a TRPC polypeptide). Biologically active portions of an enkurin protein include peptides comprising amino acid sequences sufficiently homologous to or derived from the amino acid sequence of the enkurin protein, e.g., the amino acid sequence shown in SEQ ID NO:1 or SEQ ID NO:2, which include fewer amino acids than the full length enkurin proteins, and exhibit at least one activity of an enkurin protein. Typically, biologically active portions comprise a domain or motif with at least one activity of the enkurin protein, e.g., the ability to interact with TRPC2. A biologically active portion of an enkurin protein can be a polypeptide, which is, for example, 10, 25, 50, 100, 200, or more amino acids in length. Biologically active portions of an enkurin protein can be used as targets for developing agents which modulate an enkurin mediated activity, e.g., TRPC2 binding.

An antibody that "specifically binds" to an antigen is an antibody that recognizes and binds to a particular antigen, e.g., an enkurin polypeptide, but that does not substantially recognize or bind to other molecules or proteins in a sample, e.g., a biological sample, containing an enkurin polypeptide.

"Misexpression or aberrant expression," refers to a non-wild type pattern of gene expression, at the RNA or protein level. It includes expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus. Infertile subjects with aberrant, decreased enkurin expression are candidates for treatments that increase enkurin expression or activity, or otherwise mimic the effects of enkurin in sperm.

"Subject," as used herein, refers to a human or an animal, e.g., to a mammal, such as a horse, cow, goat, sheep, goat, pig or other domestic mammal, or an experimental mammal, such as a mouse or rat, e.g., a mammalian disease model. Subjects can also be non-mammalian animals, such as birds (e.g., domestic poultry), fish, reptiles, and amphibians.

A "purified preparation of cells," refers to, in the case of plant or animal cells, an in vitro preparation of cells and not an entire intact plant or animal. In the case of cultured cells or microbial cells, it consists of a preparation wherein of the total number of cells in the preparation, at least 50% are of the desired cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference. In addition, the materials, methods, and examples are illustrative only and not intended to be limiting.

Other features and advantages of the invention will be apparent from the detailed description, and from the claims.

DESCRIPTION OF DRAWINGS

FIG. 1 is a schematic drawing that is a representation of the domain structure of murine TRPC2B (mTRPC2B; Genbank accession no. AF111107).

FIG. 2 is a representation of the deduced amino acid sequences of murine enkurin (m-enkurin; mouse genome database accession no. AK017056; SEQ ID NO:1) and of human enkurin (h-enkurin; SEQ ID NO:2). Homology with the coiled-coil domain of hGBP1 (human Guanylate Binding Protein 1) is underlined.

FIG. 3 is a representation of the constructs used in mapping domains within enkurin and mTRPC2 that interact. These constructs were tested for binding in a yeast two-hybrid screen. The upper panel is a representation of enkurin truncation constructs that do (+) or do not (−) interact with TRPC2. The lower panel is a representation of TRPC2 truncation constructs that do (+) or do not (−) interact with enkurin.

FIG. 5A is a representation of the exon/intron map of the genomic region encoding the N-terminus of TRPC2 as published in Genebank accession no. AF111108, lacking the newly discovered exon A and exon B; FIG. 5B is a representation of TRPC2 clones, their derivation from the genomic map, and their ability to form channels; and FIG. 5C is a representation of the organization and predicted protein for the new TRPC2-S, a non-channel transcript whose transcription starts in exon A and stops in "intron 7." It includes the newly discovered 5' extended region of exon A and exon B that are described herein. Also shown are examples of its splice variants.

FIG. 6 is a representation that shows the predicted amino acid sequence of mouse mTRPC2-S (SEQ ID NO:3) and human mTRPC2-S (SEQ ID NO:4).

FIG. 9A is a representation of the nucleic acid sequence of murine enkurin (Genbank accession no. AK017056; SEQ ID NO:12). FIG. 9B is a representation of the nucleic acid sequence of human enkurin (nucleic acids 1–936 of Genbank accession no. NM_145010; SEQ ID NO:20).

FIG. 12A is a representation of the nucleic acid sequence of the 5' extended TRPC2 transcript (SEQ ID NO:21) up to and including the atg (bolded) which encodes the start codon of a currently published TRPC2 sequence (Genebank accession no. AF 11108). FIG. 12B is the depicted amino acid sequence (SEQ ID NO:22) of the 5' extended TRPC2 protein, translated from the nucleic acid sequence of FIG. 12A. The final methionine (bolded) is the first methionine of the published TRPC2 sequence as seen in Genebank accession no. AF111108 describing a hypothetical protein.

FIG. 13A is a representation of the nucleic acid sequence of the 5' extended TRPC2 alternatively spliced (coding exon 1) transcript (SEQ ID NO:23) including some sequence from the published sequence of Genebank accession no. AF111108 (underlined) for reference. This alternative splice removes exon 1 that contains the previously published start site in the AF11108 sequence. In Genebank accession no. AF111107, a second alternative splice shifts the proposed start 3' in the mRNA. Thus, this alternative splice does not affect the translation of this cDNA. FIG. 13B is the depicted amino acid sequence (SEQ ID NO:24) of the 5' extended TRPC protein product of the alternatively spliced transcript, translated from the nucleic acid sequence of FIG. 13A.

FIG. 14A is a representation of the nucleic acid sequence (SEQ ID NO: 25) of the non-channel transcript which is derived from the 5' extended TRPC2 locus. Due to lack of splicing that normally removes the intron following exon 9, a termination codon is introduced truncating the open reading frame and thus encoding a non-channel transcript. The alternatively spliced exon 3 is bolded and the intron sequence which contributes to the coding region is underlined. FIG. 14B is a representation of the amino acid sequence (SEQ ID NO:26) encoded by the nucleic acid of SEQ ID NO: 25.

FIG. 15A is a representation of the nucleic acid sequence (SEQ ID NO: 27) of the non-channel transcript which is derived from the 5' extended TRPC2 locus. Due to lack of splicing that normally removes the intron following exon 7, a termination codon is introduced truncating the open reading frame and thus encoding a non-channel transcript. The alternatively spliced exon 1 is bolded. FIG. 15B is a representation of the amino acid sequence (SEQ ID NO:28) encoded by the nucleic acid sequence of SEQ ID NO: 27.

FIGS. 16A and 16B is a representation of the nucleic acid sequence of the 5' extended TRPC2 transcript unspliced (SEQ ID NO:29) with the alternatively spliced exon bolded and the atg that encodes the start codon of a currently published TRPC2 sequence (Gene accession no. AF111108) double underlined. FIG. 16B is a continuation of the sequence of FIG. 16A. FIG. 16C is the depicted amino acid sequence (SEQ ID NO:30) of the 5' extended TRPC2 protein, translated from the nucleic acid sequence of SEQ ID NO:29.

FIG. 17A is a representation of the nucleic acid sequence (SEQ ID NO:31) of the human transcript from the TRPC2 locus based on homology match without extended TRPC2 transcript. This sequence is based on EST alignments. FIG. 17B is a representation of the amino acid sequence (SEQ ID NO:32) encoded by SEQ ID NO:31.

FIG. 18 is a representation of the nucleic acid sequence (SEQ ID NO:33) of the mouse transcript from the TRPC2 locus with the encoded intro 7 sequence underlined and exon 1 in bold.

FIG. 19 is an alignment between mouse (SEQ ID NO:34) and human TRPC2-S protein (SEQ ID NO:35) which includes sequence translated from exons A, exon B, and exon 1 "−" denotes identity while "." denotes stop.

DETAILED DESCRIPTION

Figure 4:
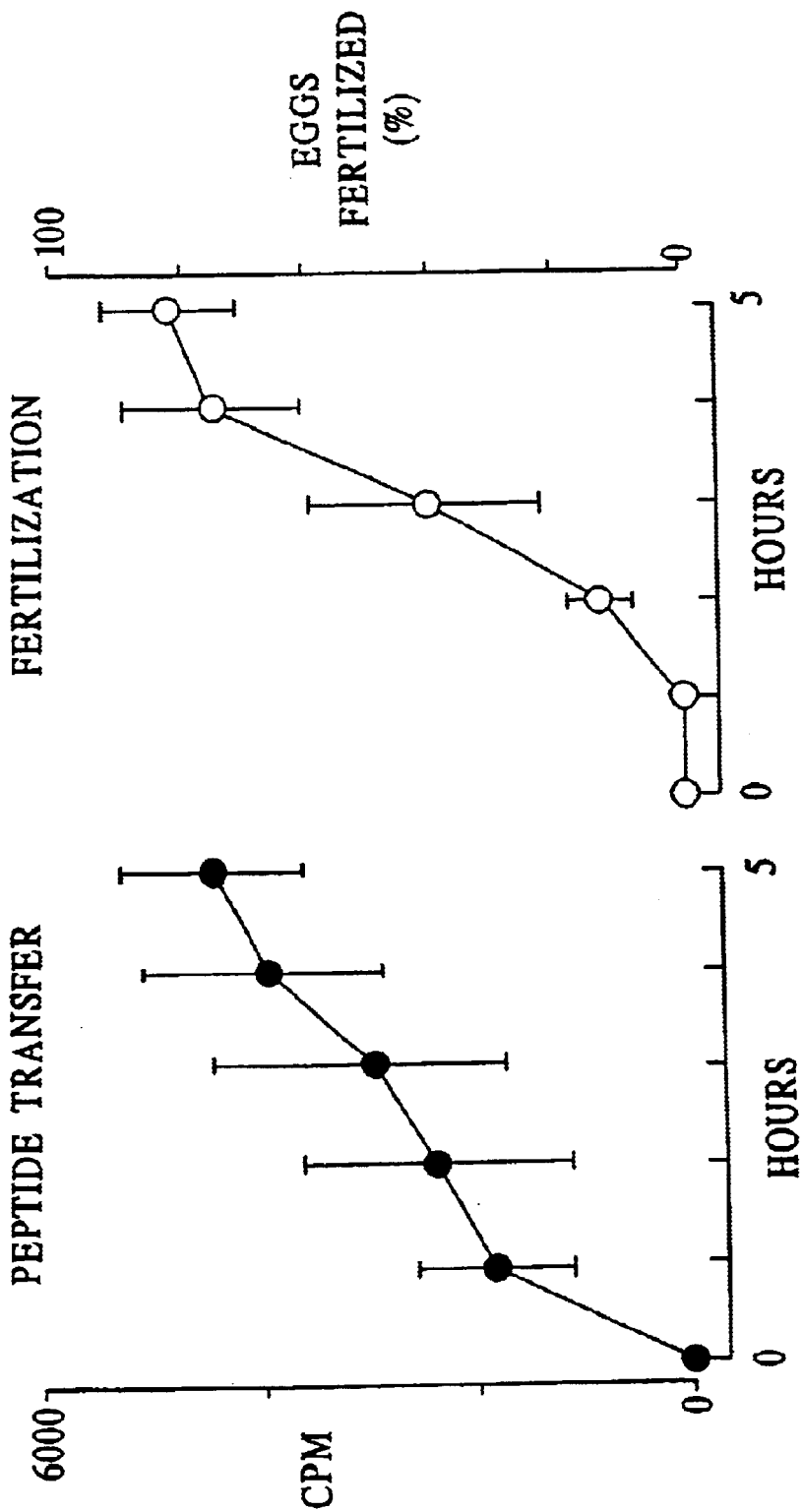
FIG. 4 is a graph showing the transfer of radioactivity (³H) labeled Ant-C-HA from sperm to egg during fertilization. The left panel shows egg-associated cpm at the indicated times. The right panel shows the time course of fertilization (+/−SD; n=3).

Enkurin is a newly discovered protein that is highly expressed in male germ cells, and interacts with Transient Receptor Potential Classic proteins (TRPCs). Murine and human homologs of enkurin are highly expressed in testis. It has also been discovered that enkurin regulates TRPC channel function.

Mouse and human sequences have been identified that correspond to full-length enkurin cDNA (Examples 1 and 2). The IMAGE clone AAH03841 that corresponds to TRPC2 was previously identified as being expressed in mouse lung tumors. It was only through the studies reported herein of mouse fertilization that the significance of the N-terminal region of mTRPC2 (murine TRPC2) was discovered, permitting the identification of both enkurin and the importance to the AR of the sequence provided in the AAH03841 clone. Identification of protein-protein interactions that are part of the mechanism for eliciting the AR provides targets for discovery of compounds useful for contraception and treating infertility. For example, sequence-based reagents can be developed that interfere with the signal transduction events involved in the AR. Examples of such reagents are described herein. Reagents that are useful for contraception include those that inhibit the acrosome reaction (AR) by targeting enkurin or a TRPC2 or splice variant thereof.

Enkurin was identified in a yeast two-hybrid strategy employed to identify proteins that interact with TRPC2 (Example 1). The DNA encoding murine enkurin was previously identified as a "hypothetical protein" and there were no reports that the sequence was expressed in the mouse. A human homolog to enkurin has also been identified. Expression of both human and mouse enkurin appears to be primarily in the testis (Examples 1, 2, and 7). This is important since enkurin is the only TRPC (Trp) binding protein identified that is specifically expressed in testis. Several proteins had previously been shown to interact with various mammalian Trps. For example, the inositol trisphosphate (IP3) receptor, caveolin, and calmodulin all interact with Trp proteins, but these proteins appear to be expressed in all (or almost all) cell types and thus are not good targets for a contraceptive compound. Enkurin is an excellent contraceptive target since agents that specifically interfere with enkurin function are unlikely to have significant side effects in tissues besides testis since it is not expressed or expressed at significantly lower levels in other tissues.

Also discovered is a transcribed 5' extended region of the TRPC2 locus. The two published sequences of TRPC2, namely Genebank accession nos. AF 111107 and AF111108, which encode a TRPC2 splice variant and TRPC2, respectively, actually only begin in the third exon (referred to here as exon 1 as originally described, the first two exons being referred to herein as exon A and exon B) of the longest existing TRPC2 transcript. Described herein is the newly discovered 5' extended region of TRPC2 which is encoded by the new exon A and exon B, referred to herein, which are upstream of the previously known exon 1. Also provided are new splice variants of TRPC2, referred to herein as TRPC2-S. These new splice variants have exon 3b spliced out (with or without exon 1 spliced out), allowing protein to be encoded from part of intron 7 (SEQ ID NO:33 underlined sequence), and introducing the stop codon upstream from the originally known stop codon for the already described TRPC2 and its splice variants. Translation from intron 7 sequence is newly discovered. Possible splice variants of TRPC2-S are listed in FIG. 5C. Also provided is a new "TRPC2-S" splice variant which is not transcribed starting from exon A but instead starting from exon 3A as seen in FIG. 5C. TRPC2 and all of its known splice variants include the newly described splice variant in which exon 1 is spliced out forming a shortened TRPC2 product, which is referred to herein as "TRPC2-S," since the splicing event introduces a stop codon. Interestingly, the TRPC2-S protein is translated from intron 7 at its 3' end and that is where the stop codon can be found for this splice variant. TRPC2 and its splice variants thus include TRPC2, TRPC2 with and without exon 1 (i.e., TRPC2-S), and TRPC2 with and without exon 3. "TRPC2" also includes the 5' extended region described herein which is also referred to herein as the "5' extended TRPC2 protein and its splice variants." As used herein the new first two codons which encode the 5' end of the 5' extended TRPC2 transcript are labeled exon A and exon B. Exon numbers 1 to 9 of the originally known TRPC2 are maintained to avoid confusion and exon A and B are the new exons of the invention. Applicants have shown that enkurin binds to TRPC2-S.

Without committing to any specific hypothesis, the findings herein suggest that $Ca^{2+}$ entry into human sperm is regulated by a TRPC2-S/enkurin complex; that this complex organizes a unique signal transduction module in which TRPC2 gene products function as adapters that bind regulatory proteins (e.g., enkurin) to ion channels; and that this signaling pathway is essential for the initiation of the human AR by ZP3.

Isolated Nucleic Acid Molecules

In one aspect, the invention provides an isolated or purified, nucleic acid molecule that encodes an enkurin polypeptide described herein, e.g., a full-length enkurin protein or a fragment thereof, e.g., a biologically active portion of enkurin protein. Also included is a nucleic acid fragment suitable for use as a hybridization probe that can be used, e.g., to identify a nucleic acid molecule encoding a polypeptide of the invention, enkurin mRNA, and fragments suitable for use as primers, e.g., PCR primers for the amplification or mutation of nucleic acid molecules. In another aspect, the invention provides an isolated or purified, nucleic acid molecule that encodes the 5' extended region of the TRPC2 transcript which includes, as referred to herein, exon A and exon B of TRPC2 or any of its various splice variants (e.g., with and without exon 1; with and without exon 3b). In another aspect, the invention provides a splice variant of TRPC2, referred to as TRPC2-S for which exon 1 is spliced out, part of intron 7 (i.e., the underlined nucleic acid sequence of SEQ ID NO:33 is translated), and an upstream stop codon is used. Other splice variants of TRPC2, as described herein, are included.

In one embodiment, an isolated nucleic acid molecule of the invention includes the nucleotide sequence shown in SEQ ID NO:12 or SEQ ID NO: 29 (nucleic acids 1–270 or 1–186 of the splice variant lacking exon 1), or the underlined nucleic acid sequence of SEQ ID NO:33 or a portion of any of these nucleotide sequences. In one embodiment, the nucleic acid molecule includes sequences encoding the murine or human enkurin protein (i.e., "the coding region" of SEQ ID NO:12), as well as 5' untranslated sequences or murine or human 5' extended TRPC2 (i.e., "the coding region" of SEQ ID NO: 29 (nucleic acids 1–270 or 1–186 of the splice variant lacking exon 1), or previously undiscovered translated sequence within intron 7 (i.e., the underlined nucleic acid sequence of SEQ ID NO:3). Alternatively, the nucleic acid molecule can include only the coding region of SEQ ID NO:12 or SEQ ID NO: 29 (nucleic acids 1–270 or 1–186 of the splice variant lacking exon 1) or the underlined nucleic acid sequence of SEQ ID NO:33, and, e.g., no flanking sequences which normally accompany the subject sequence. In another embodiment, the nucleic acid molecule encodes a TRPC binding region. In another embodiment the nucleic acid molecule encodes a protein which includes the 5' extended portion of TRPC2 including any of its splice variants. In yet another embodiment, the nucleic acid molecule encodes a protein or protein fragment which includes the previously unknown translated sequence encoded by the underlined nucleic acid sequence of SEQ ID NO:33.

In another embodiment, an isolated nucleic acid molecule of the invention includes a nucleic acid molecule which is a complement of the nucleotide sequence or a nucleotide sequence which includes the nucleotide sequence shown in SEQ ID NO:12 or SEQ ID NO:29 (nucleic acids 1–270 or 1–186 of the splice variant lacking exon 1), or the underlined nucleic acid sequence of SEQ ID NO:33, or a portion of any of these nucleotide sequences. In other embodiments, the nucleic acid molecule of the invention is sufficiently complementary to the nucleotide sequence shown in SEQ ID NO:12 SEQ ID NO:29 (nucleic acids 1–270 or 1–186 of the splice variant lacking exon 1), or the underlined nucleic acid sequence of SEQ ID NO:33, or a nucleotide molecule that includes these nucleic acids, such that it can hybridize to the nucleotide sequence shown in SEQ ID NO:12 or SEQ ID NO:29 (nucleic acids 1–270 or 1–186 of the splice variant lacking exon 1), or the underlined nucleic acid sequence of SEQ ID NO:33, thereby forming a stable duplex.

In one embodiment, an isolated nucleic acid molecule of the present invention includes a nucleotide sequence which is at least about 60%, 65%, 70%, 75%, 80%, 85%, 90%, 91%, 92%, 93%, 94%, 95%, 96%, 97%, 98%, 99%, or more identity with the entire length of the nucleotide sequence shown in SEQ ID NO:12 or SEQ ID NO:29 (nucleic acids 1–270 or 1–186 of the splice variant lacking exon 1), or the underlined nucleic acid sequence of SEQ ID NO:33, or a nucleotide sequence including these sequences, or a portion, generally of the same length, of any of these nucleotide sequences.

Nucleic Acid Fragments

A nucleic acid molecule (e.g., enkurin; 5' extended TRPC2 and its splice variants; TRPC2-S and its splice variants) can include only a portion of the nucleic acid sequence of SEQ ID NO:12 or SEQ ID NO:29 (nucleic acids 1–270 or 1–186 of the splice variant lacking exon 1) or the underlined nucleic acid sequence of SEQ ID NO:33. For example, such a nucleic acid molecule can include a fragment that can be used as a probe or primer or a fragment encoding a portion of a protein (e.g., TRPC2 protein or any of its splice variants, enkurin protein, e.g., an immunogenic or biologically active portion of TRPC2 or any of its splice variants or enkurin protein. A fragment can comprise those nucleotides of SEQ ID NO:12 that encode a TRPC binding domain of murine or human enkurin or those nucleotides that encode the 5' extended portion of TRPC2 or any of its splice variants (i.e., with or without exon 1 and with or without exon 3b). The nucleotide sequence determined from the cloning of the enkurin gene allows for the generation of probes and primers designed for use in identifying and/or cloning other enkurin family members, or fragments thereof, as well as enkurin homologues, or fragments thereof, from other species. The nucleotide sequence determined from the cloning of the 5' extended TRPC2 gene allows for the generation of probes and primers designed for use in identifying and/or cloning other TRPC2 family members, variants, or fragments thereof, as well as TRPC2 homologues, or fragments thereof, from other species.

A nucleic acid can include a nucleotide sequence that includes part, or all, of the coding region and extends into either (or both) a 5' or 3' noncoding region. Other embodiments include a fragment that includes a nucleotide sequence encoding an amino acid fragment described herein. Nucleic acid fragments can encode a specific domain or site described herein or fragments thereof, particularly fragments thereof which are at least 100 amino acids in length. Fragments also include nucleic acid sequences corresponding to specific amino acid sequences described above or fragments thereof Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, an enkurin nucleic acid fragment can include a sequence corresponding to TRPC binding domain and a TRPC2 nucleic acid fragment (or those of its splice variants) can include the new 5' extended region. Also, for example, TRPC2-S can include the translated region of intron 7 (SEQ ID NO:33 underlined nucleic acid sequence or fragment thereof).

Enkurin and TRPC2 (and those of its splice variants) probes and primers are provided. Typically a probe/primer is an isolated or purified oligonucleotide. The oligonucleotide typically includes a region of nucleotide sequence that hybridizes under stringent conditions to at least about 7, 12, or 15, for example, about 20, 25, 30, 35, 40, 45, 50, 55, 60, 65, or 75 consecutive nucleotides of a sense or antisense sequence of SEQ ID NO:12 of SEQ ID NO:29 (nucleic acids 1–270 or 1–186 of the splice variant lacking exon 1), or of a naturally occurring allelic variant or mutant of SEQ ID NO:12 or SEQ ID NO: 29 (nucleic acids 1–270 or 1–186 of the splice variant lacking exon 1), or the underlined nucleic acid sequence of SEQ ID NO:33, or other enkurin or TRPC nucleic acid sequence.

In some cases the nucleic acid is a probe, which is at least 5 or 10, and less than 200, e.g., less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

In another embodiment a set of primers is provided, e.g., primers suitable for use in a PCR, which can be used to amplify a selected region of an enkurin sequence or a TRPC2 (or TRPC2 splice variant) sequence, e.g., a domain, region, site or other sequence described herein. The primers should be at least 5, 10, or 50 base pairs in length and less than 100, or less than 200, base pairs in length and can be for example 20, 21, or 22 base pairs in length. The primers can be identical, or differ by one base from a sequence disclosed herein or from a naturally occurring variant.

A nucleic acid fragment can encode an epitope-bearing region of a polypeptide described herein.

A nucleic acid fragment encoding a "biologically active portion of a TRPC2 polypeptide or TRPC2 splice variant polypeptide" can be prepared by isolating a portion of the nucleotide sequence of SEQ ID NO:29 (nucleic acids 1–270 or 1–186 of the splice variant lacking exon 1), underlined portion of SEQ ID NO:33, or other a TRPC2 polypeptide or TRPC2 splice variant polypeptide coding sequence, which encodes a polypeptide having a TRPC2 polypeptide or TRPC2 splice variant polypeptide biological activity (e.g., the biological activities of the TRPC2 proteins are described herein), expressing the encoded portion of the TRPC2 protein or splice variant thereof (e.g., by recombinant expression in vitro) and assessing the activity of the encoded portion of the TRPC2 protein or splice variant thereof. A nucleic acid fragment encoding a biologically active portion of a TRPC2 polypeptide or splice variant thereof, may comprise a nucleotide sequence which is greater than 300 or more nucleotides in length.

A nucleic acid fragment encoding a "biologically active portion of an enkurin polypeptide" can be prepared by isolating a portion of the nucleotide sequence of SEQ ID NO:12 or 20, expressing the encoded portion of the enkurin protein or splice variant thereof (e.g., by recombinant expression in vitro) and assessing the activity of the encoded portion of the enkurin protein. A nucleic acid fragment encoding a biologically active portion of an enkurin polypeptide, may comprise a nucleotide sequence which is greater than 300 or more nucleotides in length.

In some embodiments, a nucleic acid includes a nucleotide sequence which is about 300, 400, 500, 600, 700, 800, 900, 1000, 1100, 1200, 1300 or more nucleotides in length and hybridizes under stringent hybridization conditions to a nucleic acid molecule of SEQ ID NO:12, SEQ ID NO:29 (nucleic acids 1–270 or 1–186 of the splice variant lacking exon 1), the underlined nucleic acid sequence of SEQ ID NO:33, or other TRPC2 coding sequence.

Nucleic Acid Variants

The invention further encompasses nucleic acid molecules that differ from the nucleotide sequence shown in SEQ ID NO:12 or 20. Such differences can be due to degeneracy of the genetic code (and result in a nucleic acid that encodes the same enkurin proteins as those encoded by the nucleotide sequence disclosed herein). In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NOs:1, 2, 3, or 4. If alignment is needed for this comparison, the sequences should be aligned for maximum homology. "Looped" out sequences from deletions or insertions, or mismatches, are considered differences.

Nucleic acids of the invention can be chosen for having codons, which are preferred, or not preferred, for a particular expression system. For example, the nucleic acid can be one in which at least one codon (e.g., at least 10% or 20% of the codons) has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In some embodiments, the nucleic acid differs from that of SEQ ID NO:12 or 20, e.g., as follows: by at least one but less than 10, 20, 30, or 40 nucleotides; at least one but less than 1%, 5%, 10% or 20% of the nucleotides in the subject nucleic acid. If necessary, for this analysis the sequences should be aligned for maximum homology.

Orthologs, homologs, and allelic variants of the sequences described herein can be identified using methods known in the art. These variants comprise a nucleotide sequence encoding a polypeptide that is 50%, at least about 55%, typically at least about 70–75%, more typically about 80–85%, and at least about 90–95% or more identical to the nucleotide sequence shown in SEQ ID NO:12 or 20 or a fragment of this sequence. Such nucleic acid molecules can be identified as being able to hybridize under stringent conditions, to the nucleotide sequence shown in SEQ ID NO:12 or 20 or a fragment of the sequence. Nucleic acid molecules corresponding to orthologs, homologs, and allelic variants of the enkurin cDNAs of the invention can further be isolated by mapping to the same chromosome or locus as the enkurin gene.

Variants include those that are correlated with potentiation or activation of $Ca^{2+}$ channels.

Allelic variants of enkurin, e.g., human enkurin, include both functional and non-functional proteins. Functional allelic variants are naturally occurring amino acid sequence variants of the enkurin protein within a population that maintain the ability to bind a TRPC, e.g., TRPC2. Functional allelic variants will typically contain only conservative substitution of one or more amino acids of SEQ ID NO:1 or 2, or substitution, deletion or insertion of non-critical residues in non-critical regions of the protein. Non-functional allelic variants are naturally-occurring amino acid sequence variants of the enkurin, e.g., human enkurin, protein within a population that do not have the ability to bind a TRPC or activate calcium channels. Non-functional allelic variants will typically contain a non-conservative substitution, a deletion, or insertion, or premature truncation of the amino acid sequence of SEQ ID NO:1 or 2, or a substitution, insertion, or deletion in critical residues or critical regions of the protein.

Moreover, nucleic acid molecules encoding other enkurin family members and, thus, which have a nucleotide sequence which differs from the enkurin sequences of SEQ ID NO:12 or 20 are intended to be within the scope of the invention.

Antisense Nucleic Acid Molecules, Ribozymes and Modified Nucleic Acid Molecules

In another aspect, the invention features, an isolated nucleic acid molecule that is antisense to enkurin. An "antisense" nucleic acid can include a nucleotide sequence that is complementary to a "sense" nucleic acid encoding a protein, e.g., complementary to the coding strand of a double-stranded cDNA molecule or complementary to an mRNA sequence. The antisense nucleic acid can be complementary to an entire enkurin coding strand, or to only a portion thereof (e.g., the coding region of human enkurin corresponding to SEQ ID NO:12). In another embodiment, the antisense nucleic acid molecule is antisense to a "noncoding region" of the coding strand of a nucleotide sequence encoding enkurin (e.g., the 5' and 3' untranslated regions).

An antisense nucleic acid can be designed such that it is complementary to the entire coding region of enkurin mRNA, but generally is an oligonucleotide which is antisense to only a portion of the coding or noncoding region of enkurin mRNA. For example, the antisense oligonucleotide can be complementary to the region surrounding the translation start site of enkurin mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a cell or a subject (e.g., by transfection or direct injection at a tissue site), or generated in situ such that they hybridize with or bind to cellular mRNA and/or genomic DNA encoding an enkurin protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analog (Inoue et al. (1987) *FEBS Lett.* 215:327–330).

In still another embodiment, an antisense nucleic acid of the invention is a ribozyme. A ribozyme having specificity for an enkurin-encoding nucleic acid can include one or more sequences complementary to the nucleotide sequence of an enkurin cDNA disclosed herein (i.e., SEQ ID NO:12), and a sequence having known catalytic sequence responsible for mRNA cleavage (see U.S. Pat. No. 5,093,246 or Haselhoff and Gerlach, 1988, *Nature* 334:585–591). For example, a derivative of a Tetrahymena L-19 IVS RNA can be constructed in which the nucleotide sequence of the active site is complementary to the nucleotide sequence to be cleaved in an enkurin-encoding mRNA. See, e.g., Cech et al. U.S. Pat. No. 4,987,071; and Cech et al. U.S. Pat. No. 5,116,742. Alternatively, enkurin mRNA can be used to select a catalytic RNA having a specific ribonuclease activity from a pool of RNA molecules. See, e.g., Bartel and Szostak, 1993, *Science* 261:1411–1418.

Enkurin gene expression can be inhibited by targeting nucleotide sequences complementary to the regulatory region of the enkurin (e.g., the enkurin promoter and/or enhancers) to form triple helical structures that prevent transcription of the enkurin gene in target cells. See generally, Helene, 1991, *Anticancer Drug Des.* 6:569–84; Helene, 1992, *Ann. N.Y. Acad. Sci.* 660:27–36; and Maher, 1992, *Bioassays* 14:807–15. The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

An enkurin nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup et al., 1996, *Bioorganic & Medicinal Chemistry* 4:5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup et al., 1996, supra; Perry-O'Keefe et al *Proc. Natl. Acad. Sci.* 93:14670–675.

PNAs of enkurin nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of enkurin nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup et al., 1996, supra)); or as probes or primers for DNA sequencing or hybridization (Hyrup et al., 1996, supra; Perry-O'Keefe et al., supra).

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553–6556; Lemaitre et al., 1987, *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (see, e.g., Krol et al., 1988, *Bio-Techniques* 6:958–976) or intercalating agents. (see, e.g., Zon, 1988, *Pharm. Res.* 5:539–549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to an enkurin nucleic acid of the invention, two complementary regions one having a fluorophore and one a quencher such that the molecular beacon is useful for quantitating the presence of the enkurin nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Sequence Identity Determination

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In general embodiment, the length of a reference sequence aligned for comparison purposes is at least 30%, 40%, 50%, 60%, 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. The percent identity between two amino acid sequences can be determined using the Needleman and Wunsch (*J. Mol. Biol.,* 1970, 48:444–453) algorithm which has been incorporated into the GAP program in the GCG software package (available on the internet at www.gcg.com), using either a Blossum 62 matrix or a PAM250 matrix, and a gap weight of 16, 14, 12, 10, 8, 6, or 4 and a length weight of 1, 2, 3, 4, 5, or 6. Alternatively, the percent identity between two nucleotide sequences can be determined using the GAP program in the GCG software package (available on the internet at www.gcg.com), using a NWSgapdna.CMP matrix and a gap weight of 40, 50, 60, 70, or 80 and a length weight of 1, 2, 3, 4, 5, or 6. A set of parameters that can be used (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of Meyers and Miller (*CABIOS* (1989) 4:11–17) which has been incorporated into the ALIGN program (version 2.0), using a PAM120 weight residue table, a gap length penalty of 12 and a gap penalty of 4. The nucleic acid and protein sequences described herein can be used as a "query sequence" to perform a search against public databases to, for example, identify other family members or related sequences. Such searches can be performed using the NBLAST and XBLAST programs (version 2.0) of Altschul et al.,1990, *J. Mol. Biol.* 215:403–10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to a polypeptide molecule described herein (e.g., an enkurin polypeptide or a TRPC2-S polypeptide) of the invention. To obtain gapped alignments for comparison purposes, Gapped BLAST can be utilized as described in Altschul et al., 1997, *Nucleic Acids Res.* 25:3389–3402. When utilizing BLAST and Gapped BLAST programs, the default parameters of the respective programs (e.g., XBLAST and NBLAST) can be used. These programs are available on the Internet at the world wide web address ncbi.nlm.nih.gov.

Isolated Polypeptides

In another aspect, the invention features, an isolated protein, (e.g., enkurin or 5' extended TRPC2, or TRPC2-S or splice variants of any of these) or fragment, e.g., a biologically active portion, for use as immunogens or antigens to raise or test (or more generally to bind) anti-enkurin or anti-TRPC2 antibodies or antibodies to TRPC2 splice variants. Protein of interest (enkurin or 5' extended TRPC2, or TRPC2-S or splice variants of any of these) can be isolated from cells or tissue sources using standard protein purification techniques. Protein of interest or fragments thereof can be produced by recombinant DNA techniques or synthesized chemically.

Polypeptides of the invention include those that arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In some embodiments, an enkurin polypeptide has one or more of the following characteristics:

(i) it has the ability to bind a TRPC;

(ii) it has a molecular weight, e.g., a deduced molecular weight, generally ignoring any contribution of post translational modifications, amino acid composition or other physical characteristic of SEQ ID NO:1 or SEQ ID NO:2;

(iii) it has an overall sequence similarity of at least 50%, e.g., at least 60%, or at least 70, 80, 90, or 95%, with a polypeptide of SEQ ID NO:1 or SEQ ID NO:2;

(iv) it is expressed in sperm;

(v) it has a TRPC binding domain that is about 70%, 80%, 90%, or 95% identical with amino acid residues of the TRPC binding domain of SEQ ID NO:1 (residues 160–243 of m-enkurin as illustrated in FIG. 3) or SEQ ID NO:2; and (vi) it can co-localize with a TRPC.

In some embodiments the enkurin protein, or fragment thereof, differs from the corresponding sequence in SEQ ID:1 or SEQ ID NO:2. In one embodiment it differs by at least one but by less than 15, 10, or 5 amino acid residues. In another it differs from the corresponding sequence in SEQ ID NO:1 or SEQ ID NO:2 by at least one residue but less than 20%, 15%, 10% or 5% of the residues in it differ from the corresponding sequence in SEQ ID NO:1 or SEQ ID NO:2. If this comparison requires alignment the sequences should be aligned for maximum homology. "Looped" out sequences from deletions or insertions, or mismatches, are considered differences. The differences are typically differences or changes at a non-essential residue or a conservative substitution.

Other embodiments include a protein that contain one or more changes in amino acid sequence, e.g., a change in an amino acid residue which is not essential for activity. Such enkurin proteins differ in amino acid sequence from SEQ ID NO:1 or SEQ ID NO:2, yet retain biological activity.

In one embodiment, the protein includes an amino acid sequence at least about 50%, 55%, 60%, 65%, 70%, 75%, 80%, 85%, 90%, 95%, 98% or more homologous or identical to SEQ ID NO:1 or SEQ ID NO:2.

In one embodiment, a biologically active portion of an enkurin protein includes a TRPC binding domain. Moreover, other biologically active portions, in which other regions of the protein are deleted, can be prepared by recombinant techniques and evaluated for one or more of the functional activities of a native enkurin protein.

The enkurin protein can be an amino acid sequence shown in SEQ ID NO:1 or SEQ ID NO:2. In other embodiments, the enkurin protein is substantially identical to SEQ ID NO:1 or SEQ ID NO:2. In yet another embodiment, the enkurin protein is substantially identical to SEQ ID NO:1 or SEQ ID NO:2 and retains the functional activity of the protein of SEQ ID NO:1 or SEQ ID NO:2, as described in detail in the subsections above.

Chimeric or Fusion Proteins

In another aspect, the invention provides enkurin, TRPC2, 5' extended TRPC2 or splice variants thereof chimeric or fusion proteins. As used herein, a "chimeric protein" or "fusion protein" includes polypeptide (e.g., enkurin or 5' extended TRPC2, or TRPC2-S or splice variants of) any of these linked to a non-enkurin or non-TRPC2 polypeptide, respectively. As an example, "non-enkurin polypeptide" refers to a polypeptide having an amino acid sequence corresponding to a protein that is not substantially homologous to the enkurin protein, e.g., a protein which is different from the enkurin protein and which is derived from the same or a different organism. The enkurin polypeptide of the fusion protein can correspond to all or a portion e.g., a fragment described herein of an enkurin amino acid sequence. In a preferred embodiment, an enkurin fusion protein includes at least one (or two) biologically active portion of an enkurin protein. The non-enkurin polypeptide can be fused to the N-terminus or C-terminus of the enkurin polypeptide.

The fusion protein can include a moiety that has a high affinity for a ligand. For example, the fusion protein can be a GST-enkurin fusion protein in which the enkurin sequence is fused to the C-terminus of the GST sequences. In another example, the fusion protein can be a GST-TRPC2$_{1-96}$ in which the TRPC2 sequence is fused to the C-terminus of the GST sequence. Such fusion proteins can facilitate the purification of recombinant enkurin or TRPC2 peptide. Alternatively, the fusion protein can be for example an enkurin protein or a 5' extended TRPC2 protein containing a heterologous signal sequence at its N-terminus. In certain host cells (e.g., mammalian host cells), expression and/or secretion of enkurin can be increased through use of a heterologous signal sequence.

Fusion proteins can include all or a part of a serum protein, e.g., an IgG constant region, or human serum albumin.

Fusion proteins can be incorporated into pharmaceutical compositions and administered to a subject in vivo. For example, enkurin fusion proteins or 5' extended TRPC2 (or splice variants thereof) fusion proteins can be used to affect the bioavailability of an enkurin substrate. Enkurin fusion proteins may be useful therapeutically for the treatment of disorders caused by, for example, (i) aberrant modification or mutation of a gene encoding an enkurin protein; (ii) mis-regulation of the enkurin gene; and (iii) aberrant post-translational modification of an enkurin protein.

Moreover, the enkurin-fusion proteins of the invention can be used as immunogens to produce anti-enkurin antibodies in a subject, to purify enkurin ligands and in screening assays to identify molecules that inhibit the interaction of enkurin with an enkurin substrate. The 5' extended TRPC2 (and splice variants thereof)-fusion proteins of the invention can be used as immunogens to produce anti-TRPC2 antibodies in a subject, to purify TRPC2 (and splice variants thereof)-ligands and in screening assays to identify molecules that inhibit the interaction of TRPC2 (and splice variants thereof) with a TRPC2 (and splice variants thereof) substrate.

Expression vectors are commercially available that already encode a fusion moiety (e.g., a GST polypeptide). An enkurin- or 5' extended TRPC2 (or splice variants thereof)—encoding nucleic acid can be cloned into such an expression vector such that the fusion moiety is linked in-frame to the enkurin protein or the 5' extended TRPC2 (or splice variants thereof).

Protein Variants

In another aspect, the invention also features a variant of an enkurin polypeptide, e.g., which functions as an agonist (mimetic) or as an antagonist. Variants of the enkurin proteins can be generated by mutagenesis, e.g., discrete point mutation, the insertion or deletion of sequences or the truncation of an enkurin protein. An agonist of the enkurin proteins can retain substantially the same, or a subset, of the biological activities of the naturally occurring form of an enkurin protein. An antagonist of an enkurin protein can inhibit one or more of the activities of the naturally occurring form of the enkurin protein by, for example, competitively modulating an enkurin-mediated activity of an enkurin protein. Thus, specific biological effects can be elicited by treatment with a variant of limited function. For example, treatment of a subject with a variant having a subset of the biological activities of the naturally occurring form of the protein has fewer side effects in a subject relative to treatment with the naturally occurring form of the enkurin protein.

Variants of an enkurin protein can be identified by screening combinatorial libraries of mutants, e.g., truncation mutants, of an enkurin protein for agonist or antagonist activity.

Libraries of fragments, e.g., N terminal, C terminal, or internal fragments, of an enkurin protein coding sequence can be used to generate a variegated population of fragments for screening and subsequent selection of variants of an enkurin protein.

Variants in which a cysteine residue is added or deleted or in which a residue which is glycosylated is added or deleted are useful.

Methods for screening gene products of combinatorial libraries made by point mutations or truncation, and for screening cDNA libraries for gene products having a selected property. Recursive ensemble mutagenesis (REM), a new technique which enhances the frequency of functional mutants in the libraries, can be used in combination with the screening assays to identify enkurin variants (Arkin and Yourvan, 1992, *Proc. Natl. Acad. Sci. USA* 89:7811–7815; Delgrave et al., 1993, Protein Engineering 6:327–331).

Cell based assays can be exploited to analyze a variegated enkurin library. For example, a library of expression vectors can be transfected into a cell line, e.g., a cell line, which ordinarily responds to enkurin in a substrate-dependent manner. The transfected cells are then contacted with enkurin and the effect of the expression of the mutant on signaling by the enkurin substrate can be detected, e.g., by measuring $Ca^{2+}$ channel function. Plasmid DNA can then be recovered from the cells which score for inhibition, or alternatively, potentiation of signaling by the enkurin substrate, and the individual clones further characterized.

In another aspect, the invention features a method of making an enkurin polypeptide, e.g., a peptide having a non-wild type activity, e.g., an antagonist, agonist, or super agonist of a naturally occurring enkurin polypeptide, e.g., a naturally occurring enkurin polypeptide. The method includes: altering the sequence of an enkurin polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of an enkurin polypeptide a biological activity of a naturally occurring enkurin polypeptide. The method includes: altering the sequence, e.g., by substitution or deletion of one or more residues, of an enkurin polypeptide, e.g., altering the sequence of a non-conserved region, or a domain or residue described herein, and testing the altered polypeptide for the desired activity.

Screening Assays

The invention provides screening methods (also referred to herein as "assays") for identifying modulators, i.e., candidate or test compounds or agents (e.g., proteins, peptides, peptidomimetics, peptoids, nucleic acids, aptamers, carbohydrates, polysaccharides, small non-nucleic organic molecules, inorganic molecules, and drugs) that bind to enkurin proteins, have an inhibitory (or stimulatory) effect on, for example, enkurin expression or enkurin activity, or have a stimulatory or inhibitory effect on, for example, the expression or activity of an enkurin substrate. Compounds thus identified can be used to modulate the activity of target gene products (e.g., enkurin genes) either directly or indirectly in a therapeutic protocol, to elaborate the biological function of the target gene product, or to identify compounds that disrupt normal target gene interactions. Compounds that inhibit the activity or expression of enkurin are useful as contraceptives in men or women. Because premature activation of calcium channel activity can trigger the AR, compounds that increase enkurin or activity are also useful as contraceptives.

In some embodiments, the invention provides assays for screening candidate or test compounds that are substrates of an enkurin protein or polypeptide or a biologically active portion thereof. In other embodiments, the invention provides assays for screening candidate or test compounds that bind to or modulate the activity of an enkurin protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckermann et al., 1994, J. Med. Chem. 37: 2678–2685); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, Anticancer Drug Des. 12:145).

Examples of methods for the synthesis of molecular libraries can be found in the art, for example in DeWitt et al. (1993, Proc. Natl. Acad. Sci. U.S.A. 90:6909; Erb et al. (1994, Proc. Natl. Acad. Sci. USA 91:11422); Zuckermann et al. (1994, J. Med. Chem. 37:2678); Cho et al. (1993, Science 261:1303); Carrell et al. (1994, Angew. Chem. Int. Ed. Engl. 33:2059); Carell et al. (1994, Angew. Chem. Int. Ed. Engl. 33:2061); and Gallop et al. (1994, J. Med. Chem. 37:1233).

Libraries of compounds may be presented in solution (e.g., Houghten, 1992, Biotechniques 13:412–421), or on beads (Lam, 1991, Nature 354:82–84), chips (Fodor, 1993, Nature 364:555–556), bacteria (Ladner, U.S. Pat. No. 5,223,409), spores (Ladner, U.S. Pat. No. 5,223,409), plasmids (Cull et al., 1992, Proc. Natl. Acad. Sci. USA 89:1865–1869), or on phage (Scott and Smith, 1990, Science 249:386–390; Devlin, 1990, Science 249:404–406; Cwirla et al., 1990, Proc. Natl. Acad. Sci. USA 87:6378–6382; Felici, 1991, J. Mol. Biol. 222:301–310; and Ladner supra.).

In one embodiment, an assay is a cell-based assay in which a cell that expresses an enkurin protein or biologically active portion thereof is contacted with a test compound, and the ability of the test compound to modulate enkurin activity is determined. Determining the ability of the test compound to modulate enkurin activity can be accomplished by monitoring, for example, changes in the ability of enkurin to interact with a TRPC (e.g., TRPC2). Such assays can be performed using a cell that naturally expresses the TRPC (e.g., a sperm cell) or a cell that has been transfected with an expression vector that expresses the TRPC. The ability of the test compound to modulate enkurin binding to a compound, e.g., to a TRPC or a fragment thereof, or to bind to enkurin can also be evaluated. This can be accomplished, for example, by coupling the compound, e.g., the TRPC, with a radioisotope or enzymatic label such that binding of the compound, e.g., the TRPC, to enkurin can be determined by detecting the labeled compound, e.g., substrate, in a complex. Alternatively, enkurin could be coupled with a radioisotope or enzymatic label to monitor the ability of a test compound to modulate enkurin binding to an enkurin substrate such as TRPC in a complex. For example, compounds (e.g., TRPC or a fragment thereof) can be labeled with $^{125}I$, $^{35}S$, $^{14}C$, or $^3H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a TRPC) to interact with enkurin with or without the labeling of any of the interactants can be evaluated. For example, a microphysiometer can be used to detect the interaction of a compound with enkurin without the labeling of either the compound or the enkurin (McConnell et al., 1992, Science 257:1906–1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and enkurin.

In yet another embodiment, a cell-free assay is provided in which an enkurin protein or biologically active portion thereof is contacted with a test compound and the ability of the test compound to bind to the enkurin protein or biologically active portion thereof is evaluated. Biologically active portions of the enkurin proteins to be used in assays include fragments that participate in interactions with non-enkurin molecules (such as TRPC2), e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos et al., U.S. Pat. No. 4,868,103). A fluorophore label is selected such that a first donor molecule's emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the enkurin protein to bind to a target molecule can be accomplished using real-time Biomolecular Interaction Analysis (BIA) (e.g., Sjolander and Urbaniczky, 1991, *Anal. Chem.* 63:2338–2345 and Szabo et al., 1995, *Curr. Opin. Struct. Biol.* 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product (enkurin) or the test substance is anchored onto a solid phase. The target gene product/test compound complexes anchored on the solid phase can be detected at the end of the reaction, e.g., the target gene product can be anchored onto a solid surface, and the test compound, (which is not anchored), can be labeled, either directly or indirectly, with detectable labels discussed herein.

It may be desirable to immobilize enkurin, an anti-enkurin antibody or its target molecule to facilitate separation of complexed from non-complexed forms of one or both of the proteins, as well as to accommodate automation of the assay. Binding of a test compound to an enkurin protein, or interaction of an enkurin protein with a target molecule in the presence and absence of a test or candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/enkurin fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target molecule or enkurin protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of enkurin binding or activity determined using standard techniques. Such assays can be used to evaluate the ability of a test compound to modulate the interaction between enkurin and a binding partner (e.g., a TRPC2 binding domain).

Other techniques for immobilizing either enkurin protein or a target molecule (e.g., a TRPC2 binding domain) on matrices include using conjugation of biotin and streptavidin. Biotinylated enkurin protein or target molecules can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In some assay methods, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

An assay can be performed utilizing antibodies reactive with enkurin protein or target molecules but which do not interfere with binding of the enkurin protein to its target molecule. Such antibodies can be derivatized to the wells of the plate, and unbound target or enkurin protein trapped in the wells by antibody conjugation. Methods for detecting such complexes, in addition to those described above for the GST-immobilized complexes, include immunodetection of complexes using antibodies reactive with the enkurin protein or target molecule, as well as enzyme-linked assays that rely on detecting an enzymatic activity associated with the enkurin protein or target molecule. Test compounds can be added to the assay and their ability to inhibit or enhance enkurin binding to a target molecule is assessed, e.g., by comparing the amount of binding in the presence of the test compound with the amount of binding in the absence of the test compound.

Alternatively, cell-free assays can be conducted in a liquid phase. In such an assay, the reaction products are separated from unreacted components, by any of a number of standard techniques, including, but not limited to: differential centrifugation (for example, Rivas and Minton, 1993, Trends Biochem. Sci., 18:284–7); chromatography (gel filtration chromatography, ion-exchange chromatography); electrophoresis (e.g., Ausubel et al., eds. Current Protocols in Molecular Biology 1999, J. Wiley: New York.); and immunoprecipitation (for example, Ausubel et al., eds. Current Protocols in Molecular Biology 1999, J. Wiley: New York). Such resins and chromatographic techniques are known to one skilled in the art (see, e.g., Heegaard, 1998, J. Mol. Recognit. 11:141–8; Hage and Tweed, 1997, J. Chromatogr. B. Biomed. Sci. Appl. 699:499–525). Fluorescence energy transfer may also be conveniently utilized, as described herein, to detect binding without further purification of the complex from solution. The ability of a test compound to inhibit or increase binding of enkurin to a target molecule can be tested using such methods.

The assay can include contacting the enkurin protein or biologically active portion thereof with a known compound that binds enkurin to form an assay mixture, contacting the assay mixture with a test compound, and determining the ability of the test compound to interact with an enkurin protein, wherein determining the ability of the test compound to interact with an enkurin protein includes determining the ability of the test compound to preferentially bind to enkurin or biologically active portion thereof, or to modulate the activity of a target molecule, as compared to the known compound.

To the extent that enkurin can interact in vivo with one or more cellular or extracellular macromolecules, such as proteins, inhibitors of such an interaction are useful. A homogeneous assay can be used can be used to identify inhibitors. For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, enkurin protein can be used as a "bait protein" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, that bind to or interact with enkurin ("enkurin-binding proteins" or "enkurin-bp") and are involved in enkurin activity. Such enkurin-bps can be activators or inhibitors of signals by the enkurin proteins or enkurin targets as, for example, downstream elements of an enkurin-mediated signaling pathway.

Modulators of enkurin expression can also be identified. For example, a cell or cell free mixture is contacted with a candidate compound and the expression of enkurin mRNA or protein evaluated relative to the level of expression of enkurin mRNA or protein in the absence of the candidate compound. When expression of enkurin mRNA or protein is greater in the presence of the candidate compound than in its absence, the candidate compound is identified as a stimulator of enkurin mRNA or protein expression. Alternatively, when expression of enkurin mRNA or protein is less (i.e., statistically significantly less) in the presence of the candidate compound than in its absence, the candidate compound is identified as an inhibitor of enkurin mRNA or protein expression. The level of enkurin mRNA or protein expression can be determined by methods described herein for detecting enkurin mRNA or protein.

A modulating agent can be identified using a cell-based or a cell free assay, and the ability of the agent to modulate the activity of an enkurin protein can be confirmed in vivo, e.g., in an animal model for contraception.

This invention further pertains to novel agents identified by the above-described screening assays. Accordingly, it is within the scope of this invention to further use an agent identified as described herein (e.g., an enkurin modulating agent, an antisense enkurin nucleic acid molecule, an enkurin-specific antibody, or an enkurin-binding partner) in an appropriate animal model (such as those described above) to determine the efficacy, toxicity, side effects, or mechanism of action, of treatment with such an agent. Furthermore, novel agents identified by the above-described screening assays can be used for treatments as described herein.

Anti-Enkurin, 5' Extended TRPC2, and 5' Extended Splice Variant Antibodies

Anti-enkurin antibodies can be used in screening assays, diagnostically, and in therapeutic applications. The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments that can be generated by treating the antibody with an enzyme such as pepsin.

The antibody can be a polyclonal, monoclonal, recombinant, e.g., a chimeric or humanized, fully-human, non-human (e.g., murine), or single chain antibody. In some embodiments, the antibody has effector function and can fix complement. The antibody can be coupled to a toxin or imaging agent.

A full-length enkurin protein or, antigenic peptide fragment of enkurin can be used as an immunogen or can be used to identify anti-enkurin antibodies made with other immunogens, e.g., cells, membrane preparations, and the like. The antigenic peptide of enkurin should include at least 8 consecutive amino acid residues of the amino acid sequence shown in SEQ ID NO:1 or SEQ ID NO:2, and encompasses an epitope of enkurin. The antigenic peptide can include at least 10 amino acid residues, at least 15 amino acid residues, at least 20 amino acid residues, or at least 30 amino acid residues of SEQ ID NO:1 or SEQ ID NO:2.

Epitopes encompassed by the antigenic peptide are regions of enkurin are located on the surface of the protein, e.g., hydrophilic regions, as well as regions with high antigenicity. For example, an Emini surface probability analysis of the human enkurin protein sequence can be used to indicate the regions that have a particularly high probability of being localized to the surface of the enkurin protein and are thus likely to constitute surface residues useful for targeting antibody production.

Chimeric, humanized, but most, e.g., completely human antibodies are desirable for applications which include repeated administration, e.g., therapeutic treatment (and some diagnostic applications) of human patients.

The anti-enkurin antibody can be a single chain antibody. A single-chain antibody (scFV) may be engineered (see, for example, Colcher, et al., 1999, Ann. N.Y. Acad. Sci. 880:263–80; and Reiter, 1996, Clin. Cancer Res. 2:245–52). The single chain antibody can be dimerized or multimerized to generate multivalent antibodies having specificities for different epitopes of the same target enkurin protein.

The antibody can have reduced or no ability to bind an Fe receptor, e.g., it is an isotype, subtype, fragment or other mutant, which does not support binding to an Fe receptor, e.g., it has a mutagenized or deleted Fe receptor binding region.

An anti-enkurin antibody (e.g., monoclonal antibody) can be used to isolate enkurin by standard techniques, such as affinity chromatography or immunoprecipitation. Moreover, an anti-enkurin antibody can be used to detect enkurin protein (e.g., in a cellular lysate or cell supernatant) in order to evaluate the abundance and pattern of expression of the protein. Anti-enkurin antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride, or phycoerythrin; an example of a luminescent material includes luminol; examples of bioluminescent materials include luciferase, luciferin, and aequorin, and examples of suitable radioactive material include $^{125}I, ^{131}I, ^{35}S$ or $^{3}H$.

Example 4 further illustrates methods of making and identifying anti-enkurin antibodies.

Recombinant Expression Vectors, Host Cells and Genetically Engineered Cells

Vectors, e.g., expression vectors, containing a nucleic acid encoding enkurin are useful for expressing the protein and peptides in vitro and in vivo. The recombinant expression vectors can be designed for expression of enkurin proteins in prokaryotic or eukaryotic cells, e.g., E. coli, insect cells (for example, using baculovirus expression vectors), yeast cells, or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S., 1988, Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in enkurin activity assays, (e.g., direct assays or competitive assays described in detail below), or to generate antibodies specific for enkurin proteins. To maximize recombinant protein expression in *E. coli*, the protein is expressed in a host bacterial strain with an impaired capacity to proteolytically cleave the recombinant protein (Gottesman, *Gene Expression Technology: Methods in Enzymology* 185, Academic Press, San Diego, Calif., 1990, pp. 119–128). Another strategy is to alter the nucleic acid sequence of the nucleic acid to be inserted into an expression vector so that the individual codons for each amino acid are those preferentially utilized in *E. coli* (Wada et al., 1992, Nucleic Acids Res. 20:2111–2118). Such alteration of nucleic acid sequences of the invention can be carried out by standard DNA synthesis techniques.

The enkurin expression vector can be a yeast expression vector, a vector for expression in insect cells, e.g., a baculovirus expression vector, or a vector suitable for expression in mammalian cells.

When used in mammalian cells, the expression vector's control functions are often provided by viral regulatory elements. For example, commonly used viral promoters are derived from polyoma, Adenovirus 2, cytomegalovirus, and Simian Virus 40 (SV40).

Recombinant mammalian expression vector can be used to direct expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987, Genes Dev. 1:268–277), lymphoid-specific promoters (Calame and Eaton, 1988, Adv. Immunol. 43:235–275), promoters of T cell receptors (Winoto and Baltimore, 1989, EMBO J. 8:729–733) and immunoglobulins (Banerji et al., 1983, Cell 33:729–740; Queen and Baltimore, 1983, Cell 33:741–748), neuron-specific promoters (e.g., the neurofilament promoter;

Byrne and Ruddle (1989) Proc. Natl. Acad. Sci. USA 86:5473–5477), pancreas-specific promoters (Edlund et al., 1985, Science 230:912–916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss, 1990, Science 249:374–379) and the α-fetoprotein promoter (Campes and Tilghman, 1989, Genes Dev. 3:537–546).

Other useful recombinant expression vectors are designed to produce antisense RNA. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes, see Weintraub et al. (1986, "Antisense RNA as a molecular tool for genetic analysis," Reviews: Trends in Genetics).

Under some circumstances it is desirable to produce a host cell which includes a nucleic acid encoding all or part of an enkurin nucleic acid molecule within a recombinant expression vector or an enkurin nucleic acid molecule containing sequences which allow it to homologously recombine into a specific site of the host cell's genome. A host cell can be any prokaryotic or eukaryotic cell. For example, an enkurin protein can be expressed in bacterial cells such as E. coli, insect cells, yeast, or mammalian cells (such as Chinese hamster ovary cells (CHO)) or COS cells. Other suitable host cells are known to those skilled in the art.

Vector DNA can be introduced into host cells via conventional transformation or transfection techniques, e.g., any art-recognized technique for introducing foreign nucleic acid (e.g., DNA) into a host cell, including calcium phosphate or calcium chloride co-precipitation, DEAE-dextran-mediated transfection, lipofection, or electroporation.

The host cell of the invention can be used to produce (i.e., express) an enkurin protein, e.g., by culturing a host cell (into which a recombinant expression vector encoding an enkurin protein has been introduced) in a suitable medium such that an enkurin protein is produced and, optionally isolating an enkurin protein from the medium or the host cell.

A cell or purified preparation of cells which include an enkurin transgene, or which otherwise mis-express enkurin can be used as a model for studying disorders (e.g., proliferative disorders) that are related to mutated or mis-expressed enkurin alleles or for use in drug screening. The cell preparation can consist of human or non-human cells, e.g., rodent cells, such as mouse or rat cells; rabbit cells; or pig cells. In preferred embodiments, the cell or cells include an enkurin transgene, e.g., a heterologous form of an enkurin, e.g., a gene derived from humans (in the case of a non-human cell). The enkurin transgene can be mis-expressed, e.g., overexpressed or underexpressed. The cell or cells can include a gene that mis-expresses an endogenous enkurin, e.g., a gene the expression of which is disrupted, e.g., a knockout.

The expression characteristics of an endogenous gene within a cell, e.g., a cell line or microorganism, can be modified by inserting a heterologous DNA regulatory element into the genome of the cell such that the inserted regulatory element is operably linked to the endogenous enkurin gene. For example, an endogenous enkurin gene that is "transcriptionally silent," e.g., not normally expressed, or expressed only at very low levels, may be activated by inserting a regulatory element that is capable of promoting the expression of a normally expressed gene product in that cell. Techniques such as targeted homologous recombination, can be used to insert the heterologous DNA as described in, e.g., Chappel, U.S. Pat. No. 5,272,071; WO 91/06667, published in May 16, 1991.

Recombinant Expression Vectors, Host Cells and Genetically Engineered Cells

Vectors, e.g., expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include an enkurin nucleic acid in a form suitable for expression of the nucleic acid in a host cell. For example, the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., enkurin proteins, mutant forms of enkurin proteins, 5' extended TRPC2 fusion proteins, fusion proteins of 5' extended TRPC2 splice variants, and the like).

The recombinant expression vectors of the invention can be designed for expression of enkurin proteins in prokaryotic or eukaryotic cells. For example, polypeptides of the invention can be expressed in E. coli, insect cells (e.g., using baculovirus expression vectors), yeast cells or mammalian cells. Suitable host cells are discussed further in Goeddel, 1990, Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in enkurin activity assays, (e.g., direct assays or competitive assays described in detail below), or to generate antibodies specific for enkurin proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., 1990, *Gene Expression Technology: Methods in Enzymology* 185, Academic Press, San Diego, Calif. 119–128). Another strategy is to alter the nucleic acid sequence of the nucleic acid to be inserted into an expression vector so that the individual codons for each amino acid are those preferentially utilized in *E. coli* (Wada et al, 1992, *Nucleic Acids Res.* 20:2111–2118). Such alteration of nucleic acid sequences of the invention can be carried out by standard DNA synthesis techniques.

The enkurin, 5' extended TRPC2, or 5' extended TRPC2 splice variant expression vector can be a yeast expression vector, a vector for expression in insect cells, e.g., a baculovirus expression vector or a vector suitable for expression in mammalian cells. When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al., 1987, *Genes Dev.* 1:268–277), lymphoid-specific promoters (Calame and Eaton, 1988, *Adv. Immunol.* 43:235–275), in particular promoters of T cell receptors (Winoto and Baltimore, 1989, *EMBO J.* 8:729–733) and immunoglobulins (Banerji et al., 1983, *Cell* 33:729–740; Queen and Baltimore, 1983, *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al., 1985, *Science* 230:912–916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss, 1990, *Science* 249:374–379) and the α-fetoprotein promoter (Campes and Tilghman, 1989, *Genes Dev.* 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub, H. et al., 1986, Antisense RNA as a molecular tool for genetic analysis, *Reviews—Trends in Genetics* 1:1.

Another aspect the invention provides a host cell which includes a nucleic acid molecule described herein, e.g., an enkurin, 5' extended TRPC2, or 5' extended TRPC2 splice variant nucleic acid molecule within a recombinant expression vector or an enkurin, 5' extended TRPC2, or 5' extended TRPC2 splice variant nucleic acid molecule containing sequences which allow it to homologously recombine into a specific site of the host cell's genome. The terms "host cell" and "recombinant host cell" are used interchangeably herein. Such terms refer not only to a cell in a particular subject, but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an enkurin, 5' extended TRPC2, or 5' extended TRPC2 splice variant protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) an enkurin, 5' extended TRPC2, or 5' extended TRPC2 splice variant protein. Accordingly, the invention further provides methods for producing an enkurin, 5' extended TRPC2, or 5' extended TRPC2 splice variant protein using the host cells of the invention. In one embodiment, the method includes culturing the host cell of the invention (into which a recombinant expression vector encoding an enkurin protein has been introduced) in a suitable medium such that an enkurin protein is produced. In another embodiment, the method further includes isolating an enkurin, 5' extended TRPC2, or 5' extended TRPC2 splice variant protein from the medium or the host cell.

In another aspect, the invention features a cell or purified preparation of cells that include an enkurin, 5' extended TRPC2, or 5' extended TRPC2 splice variant transgene, or cells that otherwise misexpress enkurin, 5' extended TRPC2, or a 5' extended TRPC2 splice variant. The cell preparation can consist of human or non-human cells, e.g., rodent cells, e.g., mouse, hamster, or rat cells, rabbit cells, goat cells, or pig cells. In some embodiments, the cell or cells include an enkurin, 5' extended TRPC2, or 5' extended TRPC2 splice variant transgene, e.g., a heterologous form of an enkurin, 5' extended TRPC2, or 5' extended TRPC2 splice variant, e.g., a gene derived from humans (in the case of a non-human cell). The enkurin, 5' extended TRPC2, or 5' extended TRPC2 splice variant transgene can be normally expressed or misexpressed, e.g., overexpressed or underexpressed. In other embodiments, the cell or cells include a gene which misexpress an endogenous enkurin, 5' extended TRPC2, or 5' extended TRPC2 splice variant, e.g., a gene the expression of which is disrupted, e.g., a knockout. Such cells can serve as a model for studying disorders which are related to mutated or mis-expressed enkurin, 5' extended TRPC2, or 5' extended TRPC2 splice variant alleles, or for use in drug screening.

In another aspect, the invention features, a human cell, e.g., a hematopoietic stem cell, bone marrow stromal cell, muscle cell, skin cell, or other cell transformed with nucleic acid that encodes a subject enkurin, 5' extended TRPC2, or 5' extended TRPC2 splice variant polypeptide.

Also provided are cells, e.g., human cells, e.g., human hematopoietic or fibroblast cells, in which an endogenous enkurin, 5' extended TRPC2, or 5' extended TRPC2 splice variant is under the control of a regulatory sequence that does not normally control the expression of the endogenous enkurin gene. The expression characteristics of an endogenous gene within a cell, e.g., a cell line or microorganism, can be modified by inserting a heterologous DNA regulatory element into the genome of the cell such that the inserted regulatory element is operably linked to the endogenous enkurin, 5' extended TRPC2, or 5' extended TRPC2 splice variant gene. For example, an endogenous enkurin, 5' extended TRPC2, or 5' extended TRPC2 splice variant gene that is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

Transgenic Animals

The invention provides non-human transgenic animals. Such animals are useful for studying the function and/or activity of an enkurin, 5' extended TRPC2, or 5' extended TRPC2 splice variant protein and for identifying and/or evaluating modulators of enkurin, 5' extended TRPC2, or 5' extended TRPC2 splice variant activity. As used herein, a "transgenic animal" is a non-human animal, e.g., a mammal, e.g., a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which, for example, is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous enkurin, 5' extended TRPC2, or 5' extended TRPC2 splice variant gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of an enkurin protein to particular cells. A transgenic founder animal can be identified based upon the presence of an enkurin, 5' extended TRPC2, or 5' extended TRPC2 splice variant transgene in its genome and/or expression of enkurin, 5' extended TRPC2, or 5' extended TRPC2 splice variant mRNA in tissues or cells of the animals. A transgenic founder animal can then be used to breed additional animals carrying the transgene. Moreover, transgenic animals carrying a transgene encoding an enkurin, 5' extended TRPC2, or 5' extended TRPC2 splice variant protein can further be bred to other transgenic animals carrying other transgenes.

Enkurin, 5' extended TRPC2, or 5' extended TRPC2 splice variant proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, for example, below.

Preparation of Pharmaceutical Formulations

The pharmaceutical formulations of the invention can be delivered systemically or locally. Because of the tissue specificity of enkurin, 5' extended TRPC2, or 5' extended TRPC2 splice variant expression systemic delivery of a compound that specifically interacts with enkurin, 5' extended TRPC2, or 5' extended TRPC2 splice variant will have limited side effects.

The pharmaceutical formulations of the invention are prepared for delivery using methods known in the art. For example, in a female, delivery can be topically in a similar manner that topical spermicidal jellies or foams or other such topical formulation are administered. In another example, delivery can be via an intravaginal ring, spionge, gel, foam, or other liquid. Intravaginal rings are well known in the art, and such rings can be readily adapted to deliver an enkurin-modulating or 5' extended TRPC2-modulating, or 5' extended TRPC2 splice variant-modulating compound in a pharmaceutically acceptable carrier. Typically, in preparing a pharmaceutical formulation for administration via an intravaginal ring, an oil or aqueous solution, e.g., water, is used as the carrier. Examples of suitable intravaginal rings are disclosed in U.S. Pat. Nos. 4,762,717; 5,130,137; 4,012,496; 3,854,480; 4,391,797; 4,591,496; and 5,330,768, which are incorporated herein by reference. Typical intravaginal rings that can be adapted for use in the invention are made of ethylvinylacetate. The intravaginal ring includes at least one enkurin-modulating, 5' extended TRPC2-modulating, or 5' extended TRPC2 splice variant-modulating compound at a level sufficient to inhibit the AR. Compounds that modulate enkurin, 5' extended TRPC2, or 5' extended TRPC2 splice variant expression or activity are also useful for promoting or inhibiting fertility in a male, and can be administered systemically or locally. Systemic administration can be achieved parenterally (e.g., intravenous injection, subcutaneous injection, or by implantation of a sustained release formulation), orally, by inhalation, or transdermally (e.g., iontophoretic patch). Local administration to a male can be achieved by subcutaneous injection, implantation of a sustained release formulation, transdermal administration at the scrotum, or topical administration in a similar fashion as spermicidal foams and jellies are currently administered (e.g., topical cream, jelly, foam, liquid).

The dose of the compound varies depending upon the manner of administration and the condition of the animal to be treated, and ultimately will be decided by the attending health care professional or veterinarian. Such amount of compound as determined by the attending health care professional or veterinarian to promote or inhibit sperm motility is referred to herein as an "effective amount."

While it is possible for the compounds to be administered in a pure or substantially pure form, they may also be presented in pharmaceutical formulations or preparations. The formulations to be used, for both humans and animals, comprise any of the enkurin, 5' extended TRPC2, or 5' extended TRPC2 splice variant modulating compounds described herein, together with one or more pharmaceutically acceptable carriers thereof, and optionally other therapeutic ingredients.

The carrier must be physiologically as well as pharmaceutically acceptable and compatible with the active ingredient(s) of the formulation (e.g., capable of stabilizing peptides) and not deleterious to the subject to be treated. The formulation should not include oxidizing agents or other substances known to be incompatible with peptides. For example, highly oxidative conditions can lead to the formation of cysteine sulfoxide and to the oxidation of tryptophane. Consequently, it is important to carefully select the carrier.

The formulations may conveniently be presented in unit dosage form and may be prepared by any of the methods well known in the art of pharmacy. All methods include the step of bringing the active ingredient(s) into association with the carrier which constitutes one or more accessory ingredients.

In general, the formulations for tablets or powders are prepared by uniformly and intimately blending the active ingredient(s) with finely divided solid carriers, and then, if necessary, as in the case of tablets, forming the product into the desired shape and size.

Formulations suitable for parenteral (e.g., intravenous) administration, on the other hand, conveniently comprise sterile aqueous solutions of the active ingredient(s). For example, the solutions are isotonic with the blood of the subject to be treated. Such formulations may be conveniently prepared by dissolving solid active ingredient(s) in water to produce an aqueous solution, and rendering said solution sterile. The formulation may be presented in unit or multi-dose containers, for example, sealed ampoules or vials.

Formulations suitable for sustained release parenteral administrations (e.g., biodegradable polymer formulations) are also well known in the art. See U.S. Pat. Nos. 3,773,919 and 4,767,628 and PCT Publication No. WO 94/15587.

The compounds may also be administered with other compounds capable of stimulating or inhibiting fertility. Examples of spermatogenesis stimulating agents include follicle stimulating hormone (FSH), testosterone, and agonists thereof. Examples of spermatogenesis inhibitory agents include luteinizing hormone-releasing hormone, androgen inhibitors, ethane dimethanesulfonate, and flutamide.

Gene therapy techniques, such as chimeraplasty, could also make use of enkurin, 5' extended TRPC2, or 5' extended TRPC2 splice variant nucleic acid sequences. DNA/RNA hybrids that contain a correct sequence of enkurin, 5' extended TRPC2, or 5' extended TRPC2 splice variant nucleotides can be used to repair point mutations in an gene (e.g., Gura, 1999, Science 285:316).

The pharmaceutical formulations of the invention can also be contained within a transdermal patch. Numerous transdermal patches are known in the art and can readily be adapted to contain and deliver the pharmaceutical formulations of the invention. Examples of suitable transdermal patches are disclosed in U.S. Pat. Nos. 5,223,261; 3,598,123; 4,460,372; 3,598,122; 4,573,996; and 4,624,665, which are incorporated herein by reference. Typical transdermal patches have a flexible backing, a drug reservoir layer, a semipermeable membrane, and an adhesive layer coated on the exterior surface of the semipermeable membrane. Theratech patch technology, for example, can be used in the invention. If desired, the patch may contain a skin penetration enhancer (e.g., a fatty acid ester of a fatty acid such as ethyl oleate, glyceryl monolaurate, and/or isopropyl myristate).

In an alternative patch, the pharmaceutical formulation is contained within the adhesive coating, rather than in a distinct drug reservoir layer. Such a patch may contain, for example, a flexible backing (e.g., polyethylene, polypropylene, polyurethane, and the like) and a pressure-sensitive adhesive coating contiguously adhered to one surface of the backing and containing a homogenous mixture of: (i) an acrylic polymer containing a hydrophobic monomeric acrylic or methacrylic ester of an alkyl alcohol (containing 4–10 carbons), polyanhydrides, polyvinylacetate, polylactide or polyglycolide mixes; (ii) the active ingredients, each in an amount of about 0.2 to 12 percent of the total weight of the adhesive coating; and (iii) a skin penetration enhancer that includes isopropyl myristate and glyceryl monolaurate each in an amount of about 1 to 20 percent of the weight of the adhesive coating. These examples are non-limiting, and other transdermal patches can be used in conjunction with the pharmaceutical formulations of the invention.

Solid formulations for oral administration of one or more enkurin-modulating compounds can contain suitable carriers or excipients, such as corn starch, gelatin, lactose, liposomes, acacia, sucrose, microcrystalline cellulose, kaolin, mannitol, dicalcium phosphate, calcium carbonate, sodium chloride, or alginic acid. Disintegrators that can be used include, without limitation, micro-crystalline cellulose, corn starch, sodium starch glycolate and alginic acid. Tablet binders that may be used include acacia, methylcellulose, sodium carboxymethylcellulose, polyvinylpyrrolidone (Povidone), hydroxypropyl methylcellulose, sucrose, starch, and ethylcellulose. Lubricants that may be used include magnesium stearates, stearic acid, silicone fluid, talc, waxes, oils, and colloidal silica.

Liquid formulations for oral or sublingual administration of one or more enkurin-modulating, 5' extended TRPC2-modulating, or 5' extended TRPC2 splice variant-modulating compounds typically are prepared in water or other aqueous vehicles. The liquid formulations also can include solutions, emulsions, syrups, and elixirs containing, together with the active ingredients, wetting agents, sweeteners, and coloring and flavoring agents. Various liquid and powder formulations can be prepared by conventional methods for inhalation by the subject.

Injectable formulations for delivering enkurin-modulating, 5' extended TRPC2-modulating, or 5' extended TRPC2 splice variant-modulating compounds can contain various carriers such as vegetable oils, dimethylacetamide, dimethylformamide, ethyl lactate, ethyl carbonate, isopropyl myristate, ethanol, polylactide, polyglycolide, polyols, (glycerol, propylene glycol, liquid polyethylene glycol, and the like). For intravenous injections, the compounds may be administered by the drip method, whereby a pharmaceutical formulation containing the active ingredients and a pharmaceutically acceptable carrier is infused.

Pharmaceutically acceptable carries can include, for example, 5% dextrose, 0.9% saline, Ringer's solution or other suitable carriers. For intramuscular preparations, a sterile formulation containing the active ingredients can be administered in a pharmaceutical carrier such as Water-for-Injection, 0.9% saline, or 5% glucose solution.

A topical semi-solid ointment formulation for delivery of an enkurin-modulating, 5' extended TRPC2-modulating, or 5' extended TRPC2 splice variant-modulating compound typically contains a concentration of the active ingredients from about 1 to 20% (e.g., 5 to 10%) in a carrier such as a pharmaceutical cream base. Various formulations for topical use include drops, tinctures, lotions, creams, solutions, and ointments containing the active ingredient and various supports and vehicles.

The pharmaceutical formulations of the invention can be administered to the man or woman desiring treatment with an enkurin-modulating, 5' extended TRPC2-modulating, or 5' extended TRPC2 splice variant-modulating compound (e.g., for contraception) via a variety of combinations of routes of administration.

Virtually all men or women, and male or female animals mammals, can be treated with the compositions and methods of the invention, e.g., for contraception, treatment of infertility, or disorders in which enkurin, regulation of a TRPC is useful for treatment.

EXAMPLES

Example 1

Mouse TRPC2-Associated Proteins and the Identification of Enkurin

TRPC2 is a subunit of a calcium channel localized to sperm. The channel is activated by the zona pellucida protein ZP3 to induce an acrosome reaction. A yeast two-hybrid screen was used to identify TRPC2-binding partners.

The domain structure of murine TRPC2B (mTRPC2B; Genbank accession no. AF111107) is illustrated in FIG. 1. Several alternatively spliced TRPC2 transcripts have been characterized (Vannier et al., 1999, Proc. Natl. Acad. Sci. USA 96:2060–2064; Hofmann et al., 2000, Biochem. J. 351:115–122; Liman et al., 1999, Proc. Natl. Acad. Sci. USA 96:5791–5796). mTRPC2B is expressed in mouse testis (Jungnickel et al., 2001, supra).

The N-terminal region of mTRPC2 is cytoplasmic and contains: (i) a PKD1 homology domain, a stretch of 83 amino acids that is 31% identical to a C-terminal domain of PKD1 (amino acids 4176–4260 of hPKD1; (ii) three ankyrin repeats; and (iii) a hydrophobic H1 domain that is believed to associate with the membrane but is not a transmembrane domain. The bait that was used in initial two-hybrid screens was the sequence encoding the N-terminal domain up to, but not including, the H1 domain. This sequence is unique to TRPC2 as determined by BLAST searches. A mouse testis cDNA library was used as prey.

Nine positive clones containing sequences that are expressed in testis were obtained in the screen. These sequences are candidate TRPC2-binding proteins. Three of the nine positive clones corresponded to a 1.2 kb, full-length clone, which was selected for further study.

The 1.2 kb clone was given the name "enkurin." The predicted sequence of murine enkurin (m-enkurin; SEQ ID NO:1; FIG. 2) is present in the mouse genome database (accession no. AK017056) as a hypothetical protein. The predicted m-enkurin protein is a 255 amino acid, basic protein (29.5 kDa, pI9.58). It has a proline-rich N-terminal region with several potential SH3 ligands (residues 3–95, 15% proline), including p85 and intersectin SH3 ligands, and a C-terminal region that has a conserved domain homology with the coiled-coil domain of hGBP1 (human Guanylate Binding Protein 1; this region is double-underlined in FIG. 2). There are also predicted phosphorylation sites of protein kinase A (ser 67, 189), protein kinase C (thr 34, 71; ser 58,82,101), casein kinase 2 (ser 58,189), and tyrosine kinase (tyr 172,175) phosphorylation.

Enkurin expression was examined by Northern blot analysis. Expression was detected in mouse spermatogenic cells by late meiosis. Transcription continues in post-meiotic cells. Enkurin expression in other tissues was examined by probing a mouse tissue RNA array. Although enkurin expression was enriched in testis, expression was low or undetectable in other mouse tissues including brain, eye, liver, lung, kidney, skeletal muscle, smooth muscle, pancreas, thyroid, thymus, salivary gland, spleen, ovary, prostate, epididymus, and uterus. Thus, m-enkurin is a TRPC2 binding protein that is highly enriched in mouse spermatogenic cells.

As discussed below, screens with TRPC1, TRPC3, TRPC5, and TRPC6 indicated that enkurin can interact with these proteins. Since enkurin polypeptides or mimetics can interact with members of the TRPC family, enkurin polypeptides or mimetics can be used to modulate the activity of TRPCs, including those that are not expressed in sperm. Ectopic expression of enkurin can be used, for example, to increase calcium channel activity in a cell and thus modulate cellular metabolism.

Example 2

Identification and Characterization of the Human Homolog of Enkurin (h-enkurin)

h-Enkurin, the human homolog of m-enkurin, was identified by interrogating the human genomic database (SEQ ID NO:2; FIG. 2). The deduced amino acid sequence of h-enkurin (h-enkurin; SEQ ID NO:2; FIG. 2) is present (accession no. NM_145010) as a hypothetical protein. It is 88% identical (94% similar) to m-enkurin. h-Enkurin also contains a predicted proline-rich N terminal domain (16% proline, amino acids 3–95) and a C-terminal region coiled-coil region.

Northern analysis was performed to determine the tissue distribution of h-enkurin. For these experiments, a commercially available RNA blot was used that contained equal amounts of RNA in each lane, thus permitting a determination of the relative level of enkurin expression in the various tissues. These analyses show that h-enkurin is expressed at high levels in testis, at very low levels in ovaries, and at even lower or undetectable levels in several other tissues. Thus, as in the mouse (Example 1) h-enkurin is relatively enriched in the human spermatogenic lineage.

The h-enkurin is a homolog of the mouse TRPC2-binding protein that is highly homologous to m-enkurin, and, like m-enkurin, h-enkurin is highly expressed in testis. Both sequences encoding h-enkurin and h-enkurin polypeptides are useful for, for example, screening compounds for their ability to disrupt the interaction between TRPC2 and enkurin. Such compounds are candidates for contraceptive agents.

Example 3

Identification of Enkurin/mTRPC2 Interaction Sites

To identify sites of interaction between enkurin and TRPC2, deletion constructs of enkurin and of mTRPC2 were made using standard techniques and as shown in FIG. 3. These constructs were used in a yeast two-hybrid assay. Constructs lacking an interaction site do not show expression of the reporter gene.

The results of these expreiments showed that constructs lacking the coiled-coil domain were not able to cause reporter gene expression. Furthermore, TRPC2 constructs lacking the PKD 1 homology domain fail to interact with enkurin and more specifically the coiled coil domain of enkurin suggesting that the coiled-coil domain of enkurin (e.g., m-enkurin (FIG. 3, upper panel)) interacts with a region within the PKD1 homology domain of TRPC2

(amino acid residues 320 to 371 of SEQ ID NO:30) of the full length 5' extended TRPC2 transcript) and specifically with a region encoded by nucleic acid residues 336–361 of SEQ ID NO:30 of the full length 5' extended TRPC2 transcript (FIG. 3, lower panel). The candidate enkurin interaction site from TRPC2 is: LPQHAATCGESPPPQ-PASPASLSSS (a representation of SEQ ID NOs:5, 6, 7, or 8). Other regions of m-enkurin and mTRPC2 failed to interact in the assay system.

The PKD1 homology domain is unique to TRPC2 among the TRPC family. The 25 residues that contain the candidate enkurin interaction site are 28% identical to a region within the C-terminal domain of PKD1 (Vannier et al., 1999, Proc. Nat. Acad. Sci. 96:2060–2064), but have no other significant homology matches in the database. Thus, TRPC2 has a unique binding site and can have specific functions not mimicked or duplicated by other TRPC channels. One such function is direct enkurin binding.

The PKD1 homology domain on TRPC2 may have other functions in addition to enkurin binding. The related domain of PKD1 binds several regulatory proteins, including RGS7, wnt, and the cation channel, PKD241,97, suggesting other potential functions of the site on TRPC2. There are also differences between TRPC2 and PKD1 in this region. For example, the PKD1 sequence GPDQP is PPPQP in TRPC2. The function of this poly-prolyl sequence is not known, but is present in a number of signal transduction proteins, including 3BP-1, a Rac-GAP protein 14; YAP, a Yes oncogene-associated protein 85; and MEKK4, a MAP kinase kinase kinase (Gerwins et al, 1997, J. Biol. Chem. 272:8288–8295).

Enkurin can serve as an adapter, with a C-terminal domain binding TRPC2. The N-terminal, proline-rich domain of enkurin can then bind other proteins to organize a signal transduction module.

Example 4

Enkurin Antibodies

Antibodies that are specific for enkurin are useful for methods such as in screening assays and determining whether enkurin expression or localization is altered in the presence of a test compound. Such antibodies are useful both in cell-free systems and in cellular systems (e.g., sperm).

Studies and assays carried out in cell-free systems can be carried out using epitope-tagged constructs. Antibodies that specifically bind enkurin are useful, for example, for detecting endogenous enkurin in spermatogenic cells and for modulating enkurin activity.

Antibodies that specifically bind enkurin are raised using techniques known in the art (e.g., Jungnickel et al., 2001, supra). For example, two site-directed antibodies against synthetic enkurin peptides were produced as follows. Two peptides were synthesized: IPSDLKEPPQHPRY (SEQ ID NO:9) and SVPKKIRKQKLEKEMKQ (SEQ ID NO:10), corresponding to residues 14–27 at the N-terminus and 220–236 at the C-terminus, of m-enkurin respectively. Both peptides were conjugated at their N-termini to KLH using known methods and were injected into rabbits. Production bleeds were performed and the antibodies are affinity purified. These methods are known in the art and commercial services can be used to generate such antibodies (e.g., Research Genetics, Huntsville, Ala.).

Another method that is used to produce enkurin-specific antibodies is to express an m-enkurin/MBP (maltose binding protein) fusion protein. This protein is affinity purified, cleaved, and injected into rabbits for the production of a polyclonal antiserum. Reptiles such as those described herein can be used to generate monoclonal antibodies that specifically bind to an unknown polypeptide.

Example 5

Enkurin Regulation of mTRPC2 Channel Activity

The effects of enkurin on the ion channel activity of TRPC2 were examined using HEK-293 cells that were stably transfected with TRPC2. HEK cells provide a good model for the study of receptor-activated ion channels since they have very low levels of endogenous ion channel activity and thus provide a relatively uncomplicated model for the study of exogenous channels. These cells also have endogenous adenosine receptors that regulate phospholipase C (PLC), thereby providing a facile and reversible means for activating PLC-dependent ion channels, HEK cells have been used to study TRPC2 function (Jungnickel et al., supra 2001).

In experiments on the TRPC2 channel in HEK cells, ion channel activity was measured using the perforated, whole cell patch clamp. This configuration permits the determination of ion currents while simultaneously maintaining cytoplasmic integrity.

Figures 7, 8:
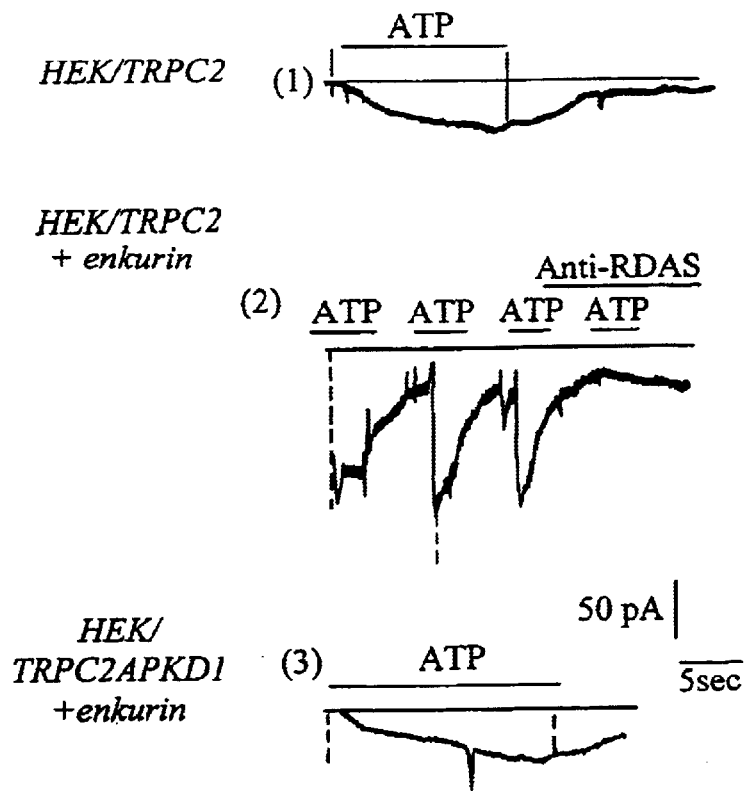
FIG. 7 is a reproduction of the results of electrophysiology experiments. Basal currents are depicted by dashed lines. Currents were evoked with ATP, with downward deflections indicating increased inward current. (A) TRPC2; (B) TRPC2+enkurin, with the addition of a TRPC2 antibody; and (C) enkurin polypeptide with the enkurin binding domain deleted+TRPC2.
FIG. 8 is a representation of the amino acid sequences of TRPC2 binding sites for enkurin in mouse (TRPC2A, SEQ ID NO:5; TRPC2-S, SEQ ID NO:6) and human (TRPC2-S, SEQ ID NO:7). Identities are shown as dashes, gaps are left blank, and conservative substitutions are shaded.

FIG. 7 shows the results of whole cell patch clamp studies on the TRPC2 channel in HEK cells. ATP (100 mM) evoked an inward current in TRPC2-expressing HEK cells (Derassi et al, 1998, Trends Cell Biol 8:84–87) that reaches peak amplitude in 20–30 seconds. However, when TRPC2 and enkurin were co-expressed (trace 2), the evoked current was 5–6 times larger (131+/–12 pA, n=5). This current activates about 25 times faster (peak amplitude in 0.5–1 seconds) and inactivates more rapidly. Total TRPC2 current, as estimated by integrating the areas beneath these traces, is increased nine +/–two-fold by enkurin. Specificity was demonstrated using anti-RDAS, an antibody against an extracellular domain of TRPC2 that blocks currents (Jungnickel, 2001, supra). Anti-RDAS blocked >95% of the ATP-evoked current in cells that had been co-transfected with TRPC2 and with enkurin (trace 2). Thus, enkurin is stimulating TRPC2 currents, not acting at some undefined endogenous channel or forming a channel itself. When enkurin was co-expressed with a deletion mutant of TRPC2 lacking the PKD1 domain (the enkurin binding site), there was no stimulation of the ATP evoked current, relative to TRPC2 alone (compare traces 3 and 1). This shows that current is enhanced as a result of enkurin/TRPC2 interaction.

These data show that enkurin is a regulator of mTRPC2 ion channel activity and so is a target for modulators of TRPC2 ion channel activity.

Examination of the functional regulation of other TRPC channels by enkurin is performed using methods such as those described above. For example, by expressing a TRPC polypeptide in HEK cells with and without co-expression of enkurin, and recording TRPC channel activity using electrophysiological methods. The experiments show whether co-expression of enkurin with TRPC channels (besides TRPC2) alters the calcium current in such cells. Compounds that alter enkurin modulation of TRPC2 activity can also be tested on cells containing other TRPC channels, thus, providing a method of identifying compounds that act preferentially on TRPC2 enkurin.

Example 6

Development of Inhibitors of Enkurin

Identification of a putative enkurin interaction site on TRPC2 provided the information for developing peptides that act as competitive antagonists. A peptide was synthesized that corresponds to the enkurin interaction site on TRPC2 (LPQHAATCGESPPPQPASPASLSSS (SEQ ID NO:8) (representative of SEQ ID NO:5, 6, or 7), designated TRPC2$_{336-361}$) and a scrambled peptide (QSAPLPSHPLPGS CPESPTQAASSA (SEQ ID NO:11) as a control. An epitope-tagged enkurin was also constructed in which the haemagglutinin-(HA-) epitope (MYPYDVPDYA; SEQ ID NO:13) was fused to the N-terminus of enkurin.

HEK/TRPC2 cells were transfected with enkurin-HA and a high speed supernatant was prepared from NP40 extracts (Jungnickel et al., 2001 supra). Anti-HA-Sepharose immunoprecipitants were collected in the presence or absence of TRPC2$_{336-361}$ peptide, resolved by SDS-PAGE and probed with anti-RDAS, a TRPC2 antibody (Jungnickel et al., 2001, supra). It was found that TRPC2 is immunoprecipitated with enkurin-HA. However, co-immunoprecipitation of TRPC2 with enkurin-HA was reduced by >90% in the presence of TRPC2$_{336-361}$ peptide. Control experiments show that this was a specific effect. First, the scrambled peptide reduced co-immunoprecipitation of TRPC2 by enkurin-HA by <25% relative to "no peptide" conditions. Finally, anti-FLAG did not precipitate TRPC2, indicating that these results are not due to non-specific antibody/Sepharose effects.

These data provide additional evidence that enkurin and TRPC2 bind to each other in a mammalian (human) cell line and, that TRPC2$_{336-361}$-derived peptides inhibit this interaction. This suggests that a peptide such as TRPC2$_{336-361}$ can be useful as an enkurin inhibitor in vivo, e.g., for modulation of AR.

In a second series of experiments, the following peptide was synthesized by Fmoc (fluoromethoxy carbonyl) chemistry and purified by reverse-phase HPLC:

RQIKIWFQNRRMKWKKL GCG MYPYDVPDYA (SEQ ID NO:14)
    Antennapedia   cys    HA

The N-terminal sequence of SEQ ID NO:14 corresponds to the third helical domain of the Drosophila antennapedia protein, which can permeate cell membranes and thereby deliver small peptides into cells. The central domain (GCG) provides a cystine for labeling and here was conjugated with ³H-iodoacetimide. The HA epitope (MYP . . . DYA) is fused to the C-terminus. Capacitated mouse sperm were incubated with this peptide (designated Ant-[³H]C-HA) for 30 minutes and then mixed with eggs in vitro. Eggs were harvested in groups of 100 at intervals, washed, and egg-associated ³H cpm were determined. FIG. 4 shows that there was a progressive transfer of ³H-peptide from sperm to eggs. The time course for this transfer roughly corresponds with that of fertilization. Fertilization is assessed by sperm head decondensation within the egg, which is visible about 30 minutes after gamete fusion. Thus, the fertilization curve lags behind gamete fusion by approximately 30 minutes and curves are then in reasonable alignment. This suggests that Ant-C-HA entered sperm and was transferred to eggs during gamete fusion. Thus, antennapedia fusions can serve to direct peptides of interest, such as TRPC2$_{336-361}$ into sperm. Such a fusion inhibitor could have the sequence:

(SEQ ID NO:38)
RQIKIWFQNRRMKWKKL LPQHAATCGESPPPQPASPASLSSS.
    Antennapedia        TRPC2$_{336-361}$ Thus, a TRPC2-derived peptide sequence that inhibits enkurin binding, has been demonstrated and methods for introducing an inhbitory peptide such as antennapedia peptide fused to TRPC2$_{336-361}$ peptide, into intact sperm are also demonstrated. These studies support a method of modulating enkurin expression or activity. An enkurin modulator can be formulated as a contraceptive, e.g., as a topical contraceptive, e.g., a contraceptive foam or gel, by using antennapedia peptide fused to TRPC2$_{336-361}$. To increase the half-life of such an enkurin inhibiting composition, synthetic peptides or peptidomimetics can be used. Such methods are known in the art. One method is to construct a peptoid or peptidomimetic analog of the inhibitory peptide or design a synthetic peptide (Simon et al., 1992, Proc. Natl. Acad. Sci. USA 89:9367–9371, Goodman et al., 2001, Biopolymers 60(3):229–45).

Example 7

Localization of TRPC2 Expression in Mouse and Human

Previously, the tissue distribution, activation mechanism and function of TRPC2 were uncertain. Three classes of TRPC2 transcripts have been described (FIG. 5).

Figures 5A, 5B:
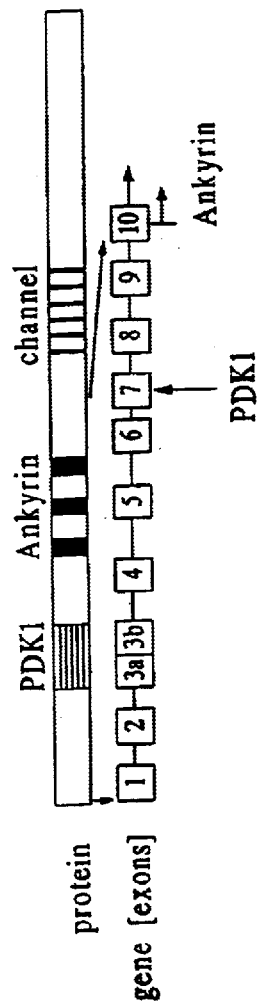
FIGS. 5A to 5C are drawings showing TRPC2 proteins and their derivation from alternatively spliced or alternatively initiated transcripts.
Figure 5C:
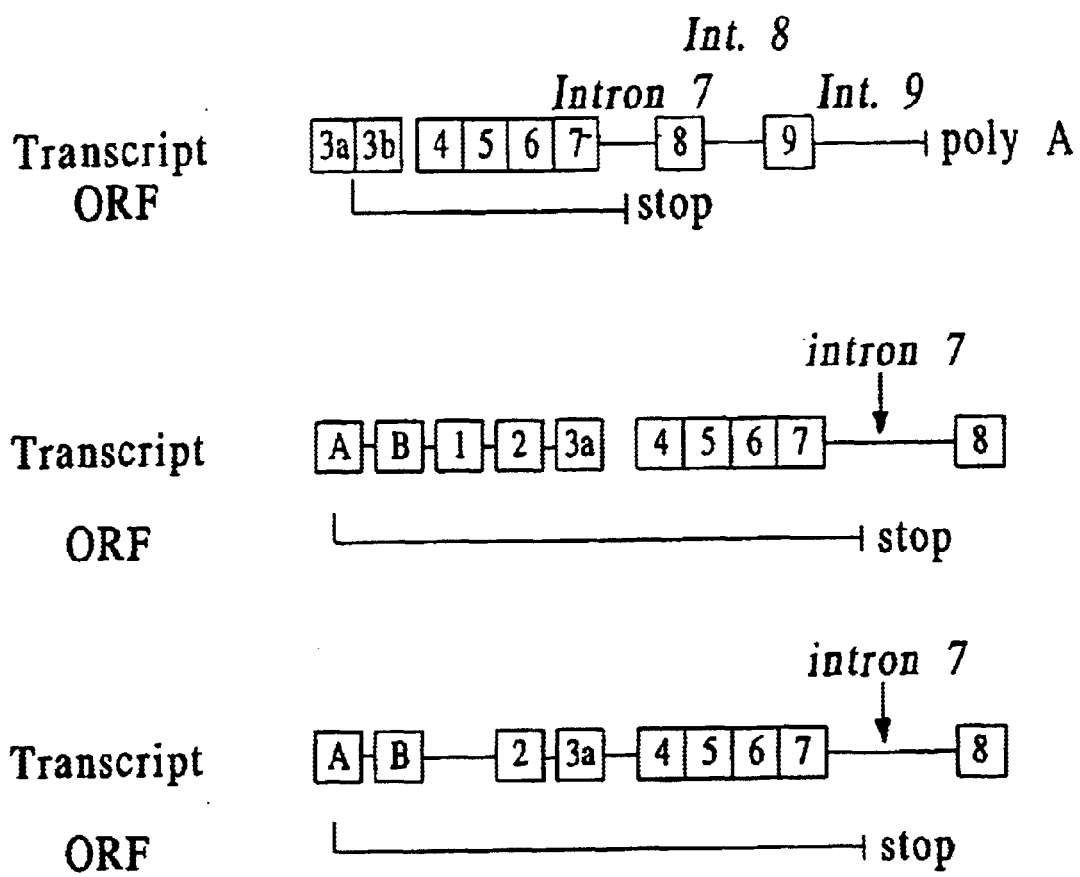

(i) Transcripts encoding proteins with long N-terminal domains were cloned from rodent testis (FIG. 5). Translation of these sequences begins either at exon 1 (mTRPC2A) or exon 3 (mTRPC2B). These transcripts form functional ion channels when overexpressed in cell lines (Vannier et al., 1999, supra).

(ii) Shorter cDNAs encoding N-terminal truncated proteins (e.g., rat rTRPC2, mouse mTRPC2b) were cloned from the vomeronasal organ (VNO) epithelium, a tissue specialized for pheromone reception. VNO transcripts start translation in exon 8. A related cDNA (mTRPC2a) has a different translation start site in exon 8, leading to a conceptually translated protein four residues shorter than the VNO-class transcripts. These transcripts encode complete channel domains, yet fail to produce functional channels in expression systems (Hofmann et al., 2000, supra; Liman et al., 1999, supra).

(iii) Human TRPC2 has several stop codons that begin in the channel domain, and so cannot form functional channels: it has thus been designated a pseudogene (Vannier et al., 1999, supra). A similar situation occurs in bovine (Wissenbach et al., 1998, FEBS Lett. 429:61–66).

The enkurin receptor/PKD1 homology domain (exon 7) is present in all transcripts that form functional ion channels. In contrast, transcripts that lack this region fail to form channels.

Interrogation of the mouse genomic database, revealed an IMAGE clone sequence that was described as "similar to TRPC2" (accession no. AAH03841; FIG. 5C; designated TRPC2-S). This clone was obtained from a mouse mammary tumor that had metastasized to the lung. This sequence starts with exon 3a of TRPC2, and includes exons 4–9. Introns 4–6 are spliced out as predicted. However, the clone then includes introns 7–8 and portions of intron 9.

Ribonuclease protection assays (RPA) were used to examine the transcription of TRPC2-S. A probe was designed spanning regions of TRPC2 exons 8 and 9 that protects a 264 base region of TRPC2-S, which has both exon 8–9; a 170 base region of exon 9 in the VNO transcript, TRPC2b; and a 94 base region of exon 8 in TRPC2A/TRPC2B transcripts (FIG. 5).

RPAs were carried out on 10 ug of total RNA isolated from testis and other tissues of immature mice. In these experiments, low levels of a 94- and 264-base protected fragment (indicative of TRPC2S and TRPC2A/B transcripts, respectively) were shown to be present at low levels in testis RNA from day 10 animals. Levels of both types of transcripts do not rise until after day 14: that is, until late spermatocytes and spermatids first appear. These results suggest that expression increases in late meiosis or in the haploid, post-meiotic period. Low levels of TRPC2-S transcripts, but not of TRPC2A/B transcripts were observed in brain, liver, heart, skeletal muscle, lung, and kidney. In contrast, a 170 base protected fragment that would have indicated TRPC2b transcription was not detected.

These data suggest that both TRPC2A/B and TRPC2-S transcripts of the TRPC2 gene are synthesized during mouse spermatogenesis and that the short TRPC2-S transcript may be widely expressed at low levels in mouse organs and tissues.

The predicted translation of mTRPC2-S yields a 22.9 kDa protein (SEQ ID NO:3; FIG. 6). The human ortholog is SEQ ID NO:4. Splicing into the predicted translation product is shown in FIG. 5 and in FIG. 6. Translation starts in exon 3b, includes exons 4–7, and terminates at a stop codon within what had been considered intron 7 (exons and intron 7 are overlined).

Several stop codons are present in all reading frames of cloned human TRPC2 sequences, beginning in the region encoding the extracellular loop linking transmembrane helices 3–4 and extending 3' from this position (Vannier et al., 1999, Proc. Natl. Acad. Sci. USA 96:2060–2064; Wes et al., 1995, Proc. Natl. Acad. Sci. USA 92:9652–9656). Specifically, interruption of the channel domain of TRPC2 (that is, the region encoding transmembrane helices and connecting loops by stop codons means that human TRPC2 cannot form functional channels. Similarly, cloned TRPC2 from bovine spermatogenic cells has a translational start site within the transmembrane domain and hence should lack the complete channel region (Wissenbach et al., 1998, FEBS Lett. 429:61–66). TRPC2-S completely lacks the transmembrane domain of TRPC2 (FIG. 5) and so cannot form an ion channel. Thus, TRPC2-S encodes a cytosolic isoform of TRPC2 that lacks a transmembrane/channel domain. The relatively high level of TRPC2-S expression suggests that it is a target for compounds that modulate sperm-related function.

Example 8

TRPC2-S is a Candidate Enkurin Receptor

There are thus at least two enkurin receptors in the mouse.

TRPC2 channel transcripts that contain the region encoded by exon 7 form one class of receptors. Hence, testis forms of TRPC2 (TRPC2A, TRPC2B) contain the binding site, but the VNO form (TRPC2b) does not.

The non-channel (TRPC2-S) transcript also encodes the enkurin binding site and serves as a receptor. As discussed herein, the enkurin-interaction domain appears to be unique to TRPC2 gene transcripts containing exon 7, as determined by BLAST sequence searches and by conserved domain searches. Hence, the simplest model is one in which only selected isoforms of TRPC2, including the non-channel TRPC2-S, are enkurin receptors.

A candidate human homolog to mouse TRPC2-S was obtained by interrogating the human genomic and EST databases. Two human ESTs were obtained (FIG. 6): SEQ ID NO:15 corresponds to mouse TRPC-2 residues 2–61 and SEQ ID NO:4 corresponds to mouse TRPC-2 residues 127–210. Mouse TRPC2-S are 58% identical (66% similar) and 77% identical (87% similar) to human genomic sequences, respectively. The second of these regions falls within genomic sequences that were previously classified as introns in TRPC2 channel transcripts. This degree of conservation is surprising for intervening sequences, suggesting that this region is functional. One example (of several) of a function might be that this is coding sequence in a heretofore undetected alternatively spliced transcript. The amino acid sequences encoded by these sites are useful, e.g., for generation of antibodies that specifically bind to TRPC2-S or as target sites for compounds that modulate TRPC2-S activity.

The predicted protein encoded by human TRPC2-S contains a consensus N-myristoylation site, which can indicate membrane localization. There are also strongly predicted phosphorylation sites for protein kinases A, C, CaM kinase II, and casein kinase I in the sequence, but mainly clustered in the domain that is encoded by exons 3b-4. Many of these sites are retained in the mouse sequence and additional sites are also present in the gap region encoded by exons 5–6 in the mouse for which there is presently no homologous human sequence.

An important structural feature that emerged from this analysis is that the PKD1 homology domain, which is encoded by exon 7, is retained in the C-terminal region of hTRPC2-S. In fact, the region of human TRPC2-S that is most highly conserved from mouse includes the PKD1-homology domain.

Example 9

Interaction of TRPC2-S with Other TRPC Proteins

To determine whether TRPC2-S binds to other TRPC proteins, HEK cells were transfected with HA-tagged TRCP2-S and with full-length TRPC plasmids. TRPC2-S was precipitated with anti-HA and blots were probed with anti-TRPC antibodies. TRPC2-S formed complexes with TRPC1, -2, -3, -5, and -6, but not with TRPC4. Note that the TRPC2 antibody used here (anti-RDAS) does not detect TRPC2-S.

These data suggest that TRPC2-S contains a domain for interacting with other TRPC proteins. Accordingly, TRPC2-S is useful, e.g., as a target for modulating TRPC activity.

Example 10

Development of TRPC2-S Antibodies

All available TRPC2 antibodies are directed against the channel domain or the C terminal tail 49,55 and so do not detect TRPC2-S proteins. TRPC2-S antibodies are prepared against peptides corresponding to residues 137–152 of the mouse TRPC2-S sequence with exon 1 spliced out (as seen in the first structure of FIG. 5C)(GFFSIETLPQHAATCG; GFF sequence; SEQ ID NO:16) and residues 189–208 (PICQLRFSAREVEEHASICG; PIC sequence; SEQ ID NO:17) of the human sequence of TRPC2-S with exon 1 spliced out (as seen in the first structure of FIG. 5C). These sequences are TRPC2-specific in BLAST searches. Both antibodies recognize mouse and human TRPC2-S. These species are 88% identical in the 137–152 and 81% identical in the 189–208 region. The GFF sequence is derived from exon 7 sequences (FIG. 6) and so is also present in the TRPC2A and TRPC2B (FIG. 5). However, TRPC2-S and the long channel proteins can be differentiated by mass (22–23 kDa and >100 kDa, respectively). In contrast, the PIC sequence is derived from TRPC2 domains that had not previously been found in any cloned cDNA and hence were considered to be intronic. This antibody does not react with any of the known TRPC2 channel proteins but specifically reacts with TRPC2-S.

MBP-fusion proteins were expressed that contain either the N-terminus or C-terminus of mTRPC2. The isolated, cleaved proteins were injected into rabbits. N-terminal antibodies are expected to react with all TRPC2 isoforms, whereas C-terminal antibodies interact with all isoforms except TRPC2-S. Antibody production can be performed by commercial entities, e.g., Research Genetics (Huntsville Ala.). Antigens were injected into rabbits. Production bleeds for antipeptide antibodies are performed and affinity purified antibodies are prepared. Monoclonal antibodies can also be prepared using methods known in the art.

As described herein, antibodies that specifically bind to TRPC2-S are useful (e.g., to localize TRPC2-S and to identify expression patterns).

Example 11

Functional Assays

Candidate compounds identified as affecting enkurin binding or activity can be subjected to additional testing in sperm. For example, sperm are treated for an appropriate amount of time (e.g., 5 minutes, 15 minutes, and 30 minutes) with a candidate compound. The sperm are then incubated with recombinant human ZP3 (rhZP3), e.g., 100 mg/ml for 20 minutes. Cells are then fixed and stained with FITC-conjugated ConA to assess the AR (Gallouzi et al., 2001, Science 294:1895–1901; Jungnickel et al, 2001, supra). Controls include: (i) buffer-treated sperm as a negative control for both rhZP3 and candidate compound; (ii) rhZP2 treatment to control for rhZP3; (iii) in the case of a candidate compound that is an antibody, a preimmune serum- and unrelated antibody-treatment to control for antibody effects; and (iv) ionomycin treatment, as a positive control to assure that sperm can undergo the AR if intracellular $Ca^{2+}$ levels are elevated. Such testing further identifies compounds that are useful, for example, as contraceptive compounds.

Example 12

$Ca^{2+}$ Imaging Assays of ZP3 Signaling

A candidate compound that has been identified as a modulator of TRPC2-S or enkurin activity can be further tested. The effect of a candidate compound on $Ca^{2+}$ levels, e.g., in human sperm can be measured in the presence of ZP3. For example, cells are loaded with a calcium-sensitive dye such as Fluo-3 and relative $Ca^{2+}$ levels are determined by image processing-enhanced fluorescence microscopy. Sperm are then treated with rhZP3 in the presence or absence of candidate compounds and $Ca^{2+}$ responses are monitored. Such methods are known in the art (Arnoult et al., 1996, Proc. Nat. Acad. Sci. USA 93:13004–13009; Arnoult et al., 1999, Proc. Natl. Acad. Sci. USA 96:6757–6762; Arnoult et al., 1996, J. Cell Biol. 134:637–645; Clark et al., 1993, J. Biol. Chem. 268:5309–5316; Florman et al., 1994, Dev. Biol. 165:152–164; Florman et al., 1992, Dev. Biol., 152:304–314; Florman et al., 1989, Dev. Biol. 135:133–146; Jungnickel et al, 2001, supra; O'Toole et al., 2000, Mol. Biol. Cell 11:1571–1584; Kirkman-Brown et al., 2000, Dev. Biol. 222:326–335. Compounds that inhibit ZP3 signalling are compounds that are useful, e.g., for inhibiting the AR. Compounds that increase the AR can also be useful, e.g., in contraceptive compounds to stimulate a premature AR reaction, thus rendering sperm ineffective for fertilization.

Example 13

Identification of Enkurin Binding Proteins

The TRPC2-binding domain of enkurin was mapped to its C-terminal region (FIG. 3). Other enkurin binding proteins are identified in two-hybrid interaction screens. Such binding proteins may include regulatory proteins (e.g., kinases and phosphatases). The experiments are performed using either full-length or an enkurin polypeptide as bait. The interaction of all candidate binding proteins is confirmed by expression of epitope-tagged binding protein- and enkurin-constructs in HEK cells, followed by pull-down experiments.

Interaction sites between enkurin and candidate binding proteins are mapped in yeast using two-hybrid approaches, as has been done for enkurin/TRPC2 interactions (FIG. 3). Results are confirmed in deletion experiments. Constructs with ablated interaction domains should no longer bind each other in yeast. If interactions are not lost after ablation, then this may indicates the presence of secondary binding sites that are identified in subsequent two-hybrid screens. Candidate compounds that modulate enkurin expression or activity can be tested in such a system. For example, the lack of expression of a reporter gene in the presence of a compound can be tested in a two-hybrid system in which enkurin and a protein that interacts with enkurin are expressed. Such methods are known in the art (e.g., Vidal et al. U.S. Pat. Nos. 5,965,368 and 5,955,280).

To assess enkurin interaction with TRPC proteins in a two-hybrid system, plasmids containing N-terminal domains of TRPC1–7 are used as prey for interactions with human enkurin. Direct binding of enkurin to various TRPC proteins is confirmed by pull-down studies in HEK cells and by functional studies. Interactions identified by such means provide additional targets for candidate compounds that modulate enkurin activitiy.

Other methods can be used to identify enkurin binding proteins. For example, enkurin enhances TRPC2 currents in HEK cells (FIG. 7). This indicates that any enkurin-binding protein required for this effect is expressed endogenously in HEK cells. Thus epitope-tagged enkurin is expressed in these cells, and the binding proteins are co-immunoprecipitated. The bound proteins are identified by mass spectrometry or by direct amino acid microsequencing. Proteins identified in these experiments are useful for screening compounds that modulate enkurin expression or activity as described herein.

Example 14

Functional Assays of Enkurin and Enkurin Binding Proteins/Regulators

Functional Assays in Heterologous Expression Systems

Enkurin enhances TRPC2 channel activity in HEK cells as assayed by patch clamping (FIG. 7). This suggests that factors (other than enkurin) required to modulate channel function are present in HEK cells. However, HEK cells do not express endogenous enkurin. Thus, a "loss of function" assay can be used in which modified enkurins are tested for their ability to enhance TRPC2 current. Alternatively, an unmodified enkurin can be expressed and the assay is employed in the presence and absence of a candidate compound to determine the ability of the compound to modulate enkurin expression or activity. The assay is also suitable for assessing the efficacy of an enkurin anti-sense nucleic acid (e.g., that is co-expressed in the cell).

In the assay, HEK cells are used that constitutively express TRPC2. Such cell lines can be produced using methods known in the art. The line should express reproducible levels of TRPC2 current. In a line that we developed, enkurin increased the peak amplitude of ATP-evoked TRPC2 currents by >5–6 fold and the activation and inactivation rates by 25 fold. In addition, this signal can be "zero-ed" using anti-RDAS, the TRPC2 blocking antibody (FIG. 7). Given this magnitude of current enhancement by enkurin in such a cell line, even subtle effects of enkurin mutants, candidate compounds, or antisense molecules are detectable.

Function is assessed by determining basal currents and ATP-evoked currents by the perforated whole cell patch clamp method. The advantages of the electrophysiological assay include reproducibility and sensitivity (pAmps and low milliseconds are readily measured). The assay is such that domains essential for enkurin function will be detected by a loss of current enhancement. Such domains include regions of enkurin essential for TRPC2 binding and may additionally include regulatory domains not directly involved in channel binding. This information can be used to design more specifically targeted compounds for modulating enkurin expression or activity. As discussed above, the assay is also useful for testing candidate compounds, including antisense enkurin nucleic acids.

Functional Assays in Sperm

Enkurin activity in sperm during ZP3 signaling can be used in assays to evaluate candidate compounds for their ability to modulate enkurin activity. The assay is based on the observation that small peptides derived from the exon 7 domain of TRPC2 act as competitive inhibitors of TRPC2/enkurin binding in HEK cells.

Experiments were performed using nucleic acids $TRPC2_{336-361}$ as the peptide derived from the exon 7 domain of TRPC2 (the sequence of this peptide is shown in FIG. 8; mouse TRPC2A; SEQ ID NO:5) and immunoprecipitation was used to examine the association of enkurin and TRPC2 in the presence of and absence of the TRPC2 peptide. Co-expression of the peptide inhibited TRPC2/enkurin binding in vivo. Expression of a scrambled peptide had little inhibitory effect.

$TRPC2_{336-361}$ is one example of a class of peptides with binding sites for enkurin. These peptides are expected to be competitive inhibitors of enkurin binding to similar domains in sperm. The major experimental obstacle to a test of this binding hypothesis is that peptides cannot be introduced by microinjection, as sperm are too small (10–20 fL total cell water; 40), or by transfection, as the cells are transcriptionally and translationally inactive. However, membrane permeant peptides can be designed and produced using methods known in the art (Derossi et al., 1998, Trends Cell Biol. 8:84–87). As discussed supra, fusion peptides attached to the C-terminus of the third helical domain of antennapedia efficiently penetrate cell membranes. Experiments have shown that antennapedia-hemagluttinin fusion peptides can be loaded into sperm and transferred to eggs at fertilization (FIG. 4). For example, the following peptides are synthesized:

(N)-RQIKIWFQNRRMKWKKL PQHAATCGETS PPHPASPSSSSSS MYPYDVPDYA-(C) (SEQ ID NO: 18) and (N)-RQIKIWFQNRRMKWKKL PQHAATCGETS PPHPASPSSSSSS -(C) (SEQ ID NO:39). This peptide consists of an N-terminal membrane penetration sequence from antennapedia (RQI . . . KKL); a central sequence (SEQ ID NO:7 lacking the first L) that is the human homolog of mouse $TRPC2_{336-361}$—that is, the enkurin binding sequence from TRPC2 (PQH . . . SSS; FIGS. 7 and 4); and a C-terminal hemagglutinin epitope (MYP . . . DYA). The hemagglutinin epitope is used to recover peptide or quantify transfer into sperm. A therapeutic compound (e.g., spermicide) would only optionally have such a component. A mouse peptide can also be synthesized using the murine TRPC2-S sequence (SEQ ID NO:6; FIG. 8). Note that the peptide shown above is based on the present knowledge enkurin mapping studies. Similar peptides can be designed based on information from studies further defining the TRPC2 binding site to a smaller region, as described herein.

The peptides are synthesized using Fmoc chemistry, purified by reversed-phase HPLC, and analyzed by mass spectrometry. It is also possible to use bacterially-synthesized recombinant peptide that is purified by HA-affinity chromatography. To increase the half-life, peptidomimetic analogs of enkurin-inhibiting peptides can be produced (Simon et al., 1992, Proc. Natl. Acad. Sci. USA 89:9367–9371, Goodman, et al., 2001, Biopolymers 60(3):229–45).

Sperm are loaded with peptide, washed by dilution, and then incubated with either mZP3 or rhZP3 for mouse and human experiments, respectively. Studies are performed to determine optimal conditions for sperm loading and for initiation of ZP3-induced ARs. Assays are conducted under conditions where alterations in sperm response to zonae is evident. Dose-response curves for the ZP3-induced AR typically exhibit Michaelis-Menton type relationship to ZP3 concentration 9,30 and thus an inhibition of the AR is not apparent if assays are run under conditions of zona-saturation. Thus, conditions must be used in which the number of ARs is linearly related to zona concentration. Controls can include antennapedia-HA peptides that lack $TRPC2_{336-361}$, antennapedia-scrambled TRPC2 peptide-HA sequences, and $TRPC2_{336-361}$-HA peptides that lack the antennapedia translocation sequence.

Permeant peptides can be designed to address the role of other enkurin binding proteins in ZP3 signaling. In addition, if specific protein kinase/phosphatase sites are implicated in enkurin action by mutagenesis experiments, then two types of experiments can test for the role of those enzymes in the ZP3-evoked AR: (i) specific membrane-permeable kinase/phosphatase inhibitors will be examined for their ability to block the AR; and (ii) the permeant peptide strategy can be adapted to ferry pseudosubstrate peptide inhibitors of these kinases/phosphatases into sperm. Enkurin antibodies are used to confirm that these treatments alter the phosphorylation state of sperm enkurin. Such treatments are useful for modulating enkurin expression or activity, e.g., for contraception.

Example 16

TRPC1 Inhibitors

Figure 10:
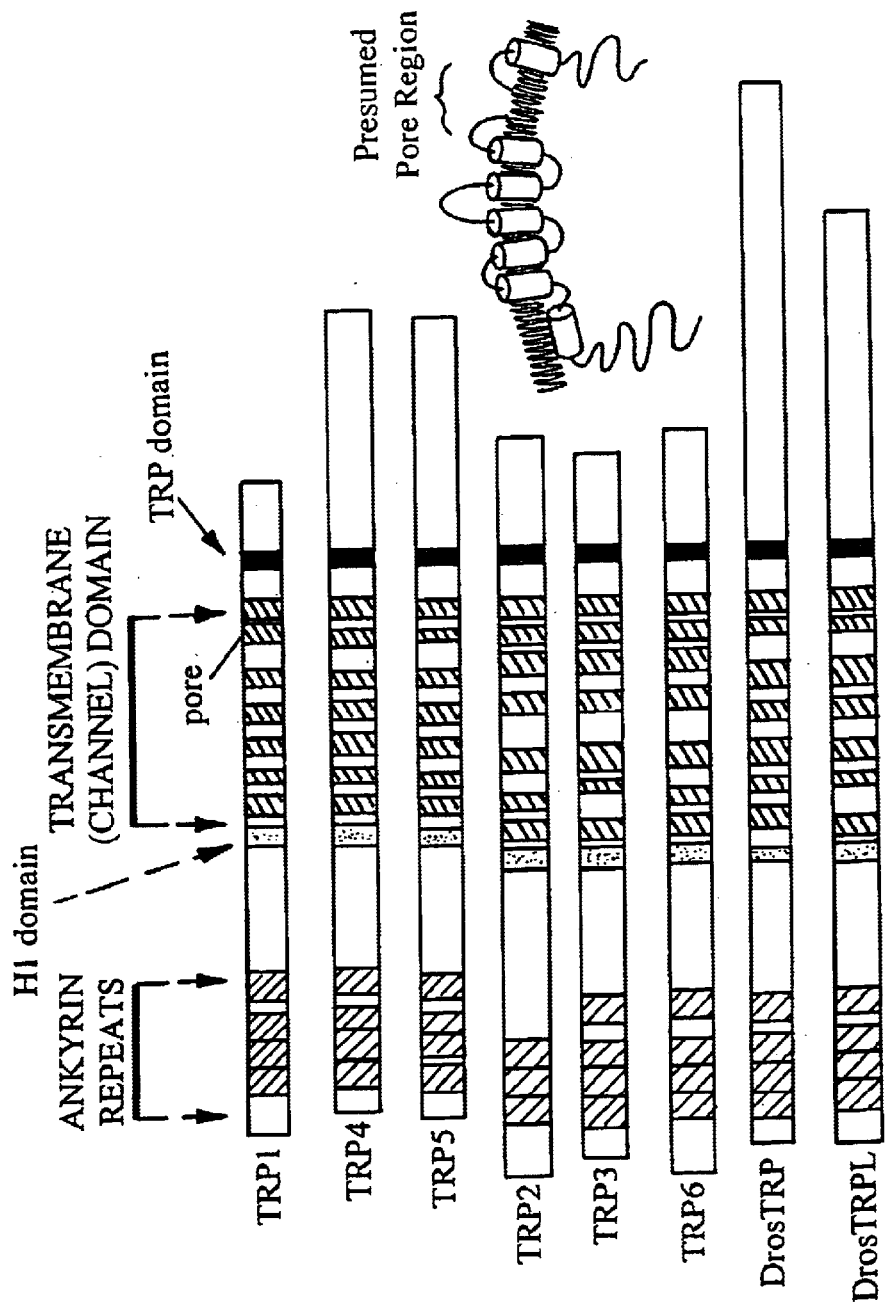
FIG. 10 is a schematic representation of the domain structure of TRPC proteins.

One method of modulating AR is through the use of agents that bind to subunits of $Ca^{2+}$ channels. To demonstrate that channels can be modulated in this manner, anti-KVAA, an affinity-purified antibody, was generated against a TRPC 1-specific peptide sequence (KVAA peptide, KVVAHNKFHDFADRKDWDAFH; SEQ ID NO:19). The KVAA peptide forms the second extracellular loop of TRPC1 and bridges transmembrane helices 3–4 (FIG. 10). Using immunofluorescence it was demonstrated that anti-KVVA labels the anterior head of mouse sperm. In addition, it detects an approximately 89 kDa band on immunoblots, close to the 87 kDa deduced molecular mass for an unglycosylated, unphosphorylated TRPC 1, based on the predicted translation of the cDNA sequence (Wes et al, 1995, Proc. Nat. Acad. Sci. USA 92:9652–9656).

To determine whether this extracellular domain antibody inhibits TRPC1 function, HEK cells were transfected with plasmids containing full-length hTRPC1 sequence. HEK cells have endogenous adenosine receptors coupled to PLC that can be used to activate heterologously expressed TRPC channels (Montell, 2001, supra).

Figure 11:
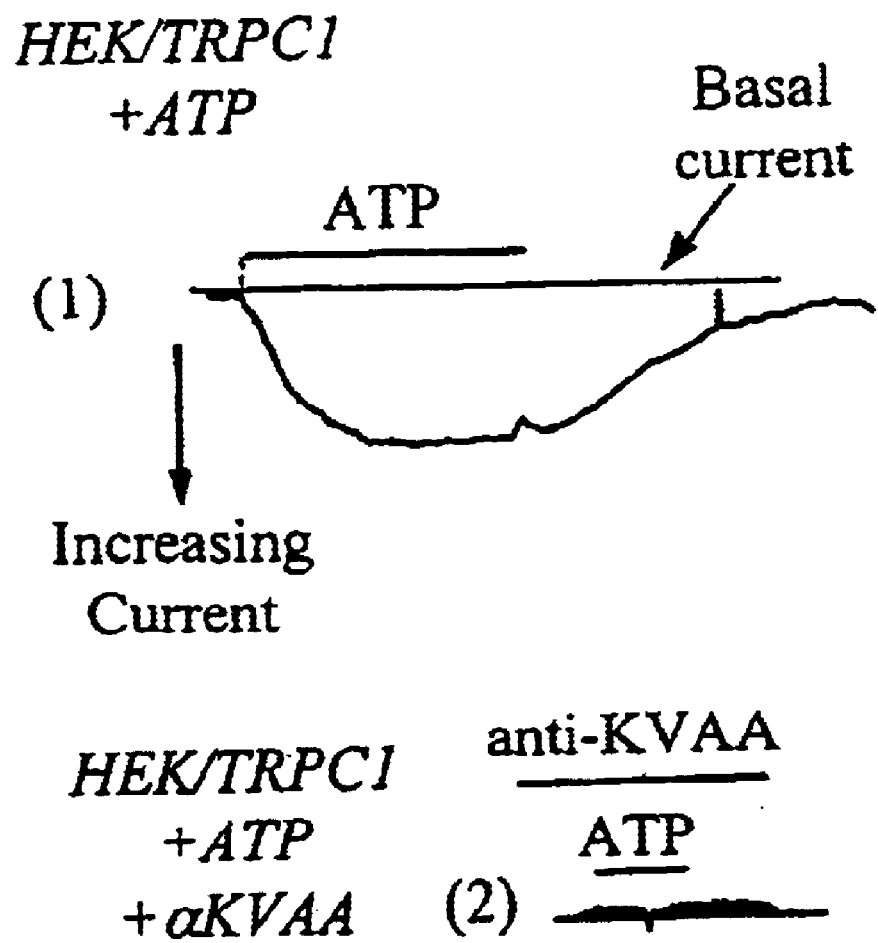
FIG. 11 is a reproduction of the results of electrophysiology experiments. Basal currents are depicted by dashed lines and inward current is shown by a downward deflection following ATP. TRPC currents are shown in the absence (1) or presence (2) of an antibody that binds to an extracellular domain of TRPC1 (anti-KVAA).

The perforated, whole cell-patch clamp method was used to measure ATP-evoked currents in the transfected cells. ATP (100 mM) triggered a rapidly-activating, inward current (~30 pAmps; FIG. 11, trace 1). Addition of anti-KVVA to the bath medium inhibited the ATP-evoked current by >95% (trace 2). This inhibition was specific and was >95% neutralized by KVVA peptide. In contrast, the anti RDAS antibody raised against an extracellular domain of TRPC2 (Jungnickel et al., 2001, Nature Cell Biol. 5:499–502) had only minor effects on this TRPC1 current (<10% inhibition). Thus, anti-KVVA is a function-blocking antibody against an extracellular domain of TRPC1. Since this inhibitor is directed against an extracellular domain of TRPC1, it will inhibit the evoked current and is useful, e.g., for preventing the $Ca^{2+}$ current that is part of the triggering mechanism for AR.

Example 17

Identification of Novel Sequence 5' of the TRPC2 Locus

Figure 20:
FIG. 20 shows an agarose gel separating RT-PCR product of the new 5' coding sequence of mouse TRPC2 from testis. The first lane contains reverse transcriptase enzyme while the second lane serves as control without reverse transcriptase. The third lane is a DNA ladder showing the size of RT-PCR product fragments. "A" is the transcript with coding exon 1 and "B" is transcript lacking coding exon 3.

RT-PCR of testis nucleic acid using the sense primer 5'-CGTCCGATGGCTCCTGTGAA-3' (SEQ ID NO:36) and the antisense primer 5'-GGCTGGCAAAACTTCCCC-3' (SEQ ID NO:37) yielded two TRPC2 products of a length that suggests that TRPC2 transcript is actually longer than originally described. FIG. 20 shows the results of RT-PCR of testis nucleic acid with the first lane showing the TRPC2 product, the second lane showing the negative control in which reverse transcriptase enzyme was not added to the reaction mix, and the third lane is a DNA ladder for reference as to the size of the product. The band designated by "A" is transcript with coding exon 1 while the band designated by "B" is transcript lacking coding exon 1. Sequencing at the 5' end of the transcript revealed that the true start site is actually 92 amino acids (FIG. 12B; SEQ ID NO:22) upstream from the originally reported start site (Genebank accession no. AF111108). Additionally, it revealed that there is a species of TRPC2 that is alternatively spliced at exon 1 Thus, all reported TRPC2 transcripts and their splice variants are transcribed from exon A and exon B and are 5' extended by a length depending upon whether or not exon 1 is spliced out or not.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A method of identifying a candidate compound that modulates the expression or activity of an enkurin polypeptide, comprising SEQ ID No. 1 or SEQ ID No. 2 the method comprising
   (a) obtaining a test sample comprising a cell that can express an enkurin polypeptide comprising SEQ ID No. 1 or SEQ ID No. 2;
   (b) contacting the test sample with a test compound;
   (c) determining a level of expression or activity of the enkurin polypeptide in the test sample of (b);
   wherein the test compound is a candidate compound for modulating enkurin expression or activity if the level of expression or activity in the test sample contacted with the test compound is different from a predetermined value.

2. The method of claim 1, wherein enkurin activity is modulated.

3. The method of claim 1, wherein enkurin nucleic acid expression is modulated.

4. The method of claim 1, wherein enkurin polypeptide expression is modulated.

5. The method of claim 1, wherein the test compound is a fusion protein.

6. The method of claim 1, wherein enkurin expression or activity is decreased.

7. The method of claim 1, wherein enkurin expression or activity is increased.

8. The method of claim 1, wherein determining the level of enkurin expression or activity comprises exposing the test sample to a compound that binds to the enkurin polypeptide and detecting levels of the compound.

9. The method of claim 8, wherein the compound that binds to the enkurin polypeptide is an antibody.

10. The method of claim 1, wherein the enkurin polypeptide comprises SEQ ID NO:1.

11. The method of claim 1, wherein the enkurin polypeptide comprises SEQ ID No: 2.

12. The method of claim 1, further comprising
    (d) assaying $Ca^{2+}$ influx in the presence of the test compound; and
    (e) determining the amount of $Ca^{2+}$ influx in the presence of the test compound compared to a reference compound such that a difference in the amount of $Ca^{2+}$ influx indicates that the test compound is a candidate compound for modulating enkurin expression or activity.

13. A purified polypeptide consists of SEQ ID NO:1.

14. A purified polypeptide consists of SEQ ID No: 2.

15. A purified polypeptide comprises SEQ ID No: 1.

16. A purified polypeptide comprises SEQ ID No: 2.

* * * * *